(12) United States Patent
Das et al.

(10) Patent No.: US 7,642,257 B2
(45) Date of Patent: Jan. 5, 2010

(54) PHENYL-ANILINE SUBSTITUTED BICYCLIC COMPOUNDS USEFUL AS KINASE INHIBITORS

(75) Inventors: Jagabandhu Das, Mercerville, NJ (US); John Hynes, Washington Crossing, PA (US); Katerina Leftheris, Skillman, NJ (US); Shuqun Lin, Newtown, PA (US); Stephen T. Wrobleski, Whitehouse Station, NJ (US); Hong Wu, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/047,550

(22) Filed: Mar. 13, 2008

(65) Prior Publication Data

US 2008/0167304 A1 Jul. 10, 2008

Related U.S. Application Data

(62) Division of application No. 10/970,420, filed on Oct. 21, 2004, now Pat. No. 7,419,978.

(60) Provisional application No. 60/513,285, filed on Oct. 22, 2003.

(51) Int. Cl.
C07D 487/04 (2006.01)
A61K 31/4985 (2006.01)
A61P 19/02 (2006.01)

(52) U.S. Cl. .................... 514/248; 544/349; 544/350
(58) Field of Classification Search ............. 544/349, 544/350; 514/248
See application file for complete search history.

(56) References Cited

U.S. PATENT DOCUMENTS

| | | | |
|---|---|---|---|
| 4,200,750 A | 4/1980 | Warner, Jr. et al. |
| 5,658,903 A | 8/1997 | Adams et al. |
| 5,932,576 A | 8/1999 | Anantanarayan et al. |
| 5,945,418 A | 8/1999 | Bemis et al. |
| 5,977,103 A | 11/1999 | Adams et al. |
| 6,087,496 A | 7/2000 | Anantanarayan et al. |
| 6,130,235 A | 10/2000 | Mavunkel et al. |
| 6,147,080 A | 11/2000 | Bemis et al. |
| 6,251,914 B1 | 6/2001 | Adams et al. |
| 6,277,989 B1 | 8/2001 | Chakravarty et al. |
| 6,492,383 B1 | 12/2002 | Munchhof et al. |
| 6,670,357 B2 | 12/2003 | Leftheris et al. |
| 2003/0224184 A1 | 12/2003 | Hermes et al. |
| 2004/0023992 A1 | 2/2004 | Das et al. |
| 2004/0082582 A1 | 4/2004 | Dyckman et al. |

FOREIGN PATENT DOCUMENTS

| EP | 0 447 891 | 4/1994 |
|---|---|---|
| FR | 2 662 163 | 11/1991 |
| WO | WO 95/19774 | 7/1995 |
| WO | WO 96/40142 | 12/1996 |
| WO | WO 97/13771 | 4/1997 |
| WO | WO 99/24440 | 5/1999 |
| WO | WO 00/12074 | 3/2000 |
| WO | WO 00/12497 | 3/2000 |
| WO | WO 00/56738 | 9/2000 |
| WO | WO 01/14378 | 3/2001 |
| WO | WO 01/27089 | 4/2001 |
| WO | WO 01/34605 | 5/2001 |
| WO | WO 02/40486 | 5/2002 |

OTHER PUBLICATIONS

Anderson, W.K. et al., "Design, Synthesis, Antineoplastic Activity, and Chemical Properties of Bis(carbamate) Derivatives of 4,5-Bis(hydroxymethyl)imidazole", J. Med. Chem., vol. 32, No. 1, pp. 119-127 (1989).
Bayon, J.C. et al., "Dinuclear Rhodium and Iridium Complexes of Dicarboxyimidazolates; Crystal Structure of [NB$_{U4}$][(cod)Rh(dcbi)Rh(cod)]+Pr$^1$OH", J. Chem. Soc. Dalton Trans., pp. 3003-3007 (1987).
Brown, D.J. et al., "Isomerisationss Akin to the Dimroth Rearrangement. Part II. The Equilbria of 4-Mercapto-1,2,3,5,7-penta-azaindenes with 4-Amino-1-thia-2,3,5,7-tetra-azaindenes", J. Chem. Soc. (C), pp. 1856-1860 (1967).
Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).
Bundgaard, H., ed., Design of Prodrugs, Elsevier Science Publishers B.V., publ. (1985) (table of contents).
Bundgaard, H., "Means to Enhance Penetration: Prodrugs as a means to improve the delivery of peptide drugs", Advanced Drug Delivery Reviews, vol, 8, pp. 1-38 (1992).
Butters, M., "Large Scale Synthesis of 4-Ethylpyrimidine", J. Heterocyclic Chem., vol. 29, pp. 1369-1370 (1992).
Cohnen, E. et al, "A Simple Synthesis of Pyrroles", Synthesis, pp. 566-568 (1987).
Henry, J.R. et al., "p38 mitogen-activated protein kinase as a target for drug discovery", Drugs of the Future, vol. 24, No. 12, pp. 1345-1354 (1999).
Moreland, L.W. et al., "Etanercept Therapy in Rheumatoid Arthritis: A Randomized, Controlled Trial", Ann. Intern. Med., vol. 130, No. 6, pp. 478-486 (1999).

(Continued)

*Primary Examiner*—Venkataraman Balasubramanian
(74) *Attorney, Agent, or Firm*—Laurelee A. Duncan

(57) ABSTRACT

Compounds having the formula (I),

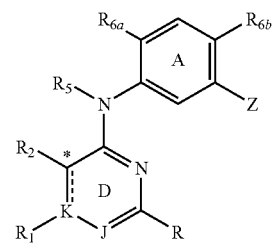

and pharmaceutically acceptable salts, prodrugs, and solvates thereof, are useful as kinase inhibitors, wherein R, $R_1$, $R_2$, $R_5$, $R_{6a}$, $R_{6b}$, J, K, X and Z are as described in the specification.

13 Claims, No Drawings

OTHER PUBLICATIONS

Raingeaud, J. et 81., "MKK3- and MKK6-Regulated Gene Expression Is Mediated by the p38 Mitogen-Activated Protein Kinase Signal Transduction Pathway", Molecular and Cellular Biology, vol. 16, No. 3, pp. 1247-1255 (1996).

Rankin, E.C.C. et al., "The Therapeutic Effects of an Engineered Human Anti-Tumour Necrosis Factor Alpha Antibody (CDP571) in Rheumatoid Arthritis", British Journal of Rheumatology, vol. 34, No. 4, pp. 334-342 (1995).

Salituro, F.G. at al., "Inhibitors of p38 MAP Kinase: Therapeutic Intervention in Cytokine-Mediated Diseases", Current Medicinal Chemistry, vol. 6, No. 9, pp. 807-823 (1999).

Widder, K.J. et al., eds., Section III: "Prodrugs", Methods in Enzymology, vol. 112, Academic Press, Inc., publ., pp. 309-396 (1985).

Graninger et al. Curr. Opin. Rheumatol. 13(3): 209-213, 2001.

Nagarkatti et al. J. Mol. Cell Cardiol. 30(8): 1651-1664, 1998.

Brunet et al., Esaays Biochem. 32: 1-16, 1997.

Herlaar et al., Mol. Med. Today 5(10) 439-447, 1999.

Wolft Manfred E., Burger's Medicinal Chem., 5ed, Part. J, John Wiley and Sons, 1995, pp. 975-977.

Banker, G.S. etal., Modern Pharmaceutices, 3ed., Marcel Dekker, NY 1996 pp. 451-596.

West, Anthony R., Solid State Chemistry and its Applications, Wiley, NY 1988, pp. 358-365.

Vippagunta et al., Advanced Drug Delivery Reviews 48: 3-26, 2001.

PHENYL-ANILINE SUBSTITUTED BICYCLIC COMPOUNDS USEFUL AS KINASE INHIBITORS

CROSS-REFERENCE TO RELATED APPLICATION

This application is a Divisional of U.S. Ser. No. 10/970,420, filed Oct. 21, 2004, now U.S. Pat. No. 7,419,978, which claims priority from Provisional Application Ser. No. 60/513,285, filed Oct. 22, 2003, which is herein incorporated by reference in its entirety.

FIELD OF THE INVENTION

This invention relates to phenyl-aniline substituted bicyclic compounds, more particularly, to phenyl-aniline substituted bicyclic compounds useful for treating p38 kinase-associated conditions. The invention further pertains to pharmaceutical compositions containing at least one compound according to the invention useful for treating p38 kinase-associated conditions and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.* 6:807-823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334-342 (1995)], and soluble TNF-α receptor-Fc fusion protein (Etanercept) [Moreland et al., *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in International applications WO 00/56738 and WO 01/27089 to Astra Zeneca; U.S. Pats. Nos. 6,277,989 and 6,130,235 to Scios, Inc; U.S. Pats. Nos. 6,147,080 and 5,945,418 to Vertex Pharmaceuticals Inc; U.S. Pats. Nos. 6,251,914, 5,977,103 and 5,658,903 to SmithKline Beecham Corp.; U.S. Pats. Nos. 5,932,576 and 6,087,496 to G. D. Searle & Co.; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain phenyl-aniline substituted bicyclic compounds, particularly, phenyl-aniline substituted bicyclic compounds useful as kinase inhibitors, particularly kinases p38α and β. Bicyclic compounds useful as tyrosine kinase inhibitors are disclosed in U.S. patent application Ser. No. 09/573,829, filed May 18, 2000, assigned to the present assignee. Methods of treating p38 kinase-associated conditions as well as certain bicyclic compounds useful for that purpose are described in U.S. patent application Ser. No. 10/036,293, assigned to the present assignee and having common inventors herewith, which claims the benefit of U.S. Provisional Application No. 60/249,877, filed Nov. 17, 2000, and U.S. Provisional Application No. 60/310,561, filed Aug. 7, 2001. Methods of making certain bicyclic compounds are described in U.S. patent application Ser. No. 10/289,101, filed Nov. 6, 2002. Certain bicyclic compounds substituted with an acidic group reportedly having sPLA$_2$-inhibitory activity are disclosed in WO 01/14378 A1 to Shionogi & Co., Ltd, published Mar. 1, 2001 in Japanese. Bicyclic compounds having hyperproliferative and other activities are disclosed in U.S. Pat. No. 6,492,383, WO 99/24440, and WO 96/40142 to Pfizer; EP 447891 to BASFAG; WO 95/19774 to Warner-Lambert Co.; and WO 97/13771 to Glaxo Group Ltd., UK.

Each of the patent applications, patents, and publications referred to herein is incorporated herein by reference.

SUMMARY OF THE INVENTION

The instant invention pertains to compounds of formula (I),

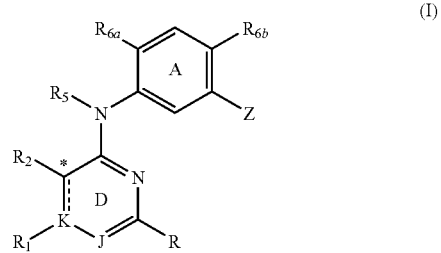

(I)

their enantiomers, diastereomers, and pharmaceutically-acceptable salts, prodrugs, and solvates thereof, wherein:

J is nitrogen or —CR$_8$;

K is nitrogen or carbon, wherein when K is nitrogen, the bond between K and carbon atom C* is a single bond, and when K is carbon, the bond between K and carbon atom C* is a double bond;

Z is selected from —NHR$_{11}$, —C(=O)NR$_{11}$R$_{12}$, —NR$_{11}$C(O)$_2$R$_{12}$, —NR$_{11}$C(=O)R$_{13}$, —NR$_{11}$C(=O)NR$_{12}$R$_{13}$, —NR$_{11}$SO$_2$R$_{14}$, —SO$_2$NR$_{12}$, —C(=O)R$_{12}$, —OC(=O)R$_{15}$, —C(=O)NR$_{11}$C(=O)R$_{13}$, —C(=O)NR$_{11}$C(=O)NR$_{12}$R$_{13}$, and optionally-substituted heteroaryl;

R$_5$ is hydrogen or C$_{1-4}$alkyl;

R$_{6a}$ and R$_{6b}$ are independently selected from hydrogen, C$_{1-4}$alkyl, hydroxy, methoxy, halogen, cyano, amino, —NH($C_{1-4}$alkyl), —N($C_{1-4}$alkyl)$_2$, —$CF_3$, —$OCF_3$, and $C_{1-4}$alkyl substituted with one or two of hydroxy, methoxy, halogen, cyano, amino, —NH($C_{1-4}$alkyl), —N($C_{1-4}$alkyl)$_2$—$CF_3$, and/or —$OCF_3$;

R and $R_8$ are independently selected from hydrogen, alkyl, substituted alkyl, hydroxy, alkoxy, halogen, cyano, amino, alkylamino, haloalkoxy, cycloalkyl, aryl, heterocyclo, and heteroaryl;

$R_1$ and $R_2$ are taken together to form a ring fused to ring D via bond K ----- *, wherein (a) when K is carbon, $R_1$ and $R_2$ (considered together with K, the C* atom, and the bond joining K and C*), form a fused ring selected from one of:

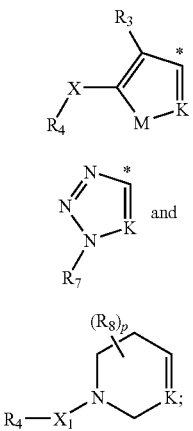

wherein M is —N($R_7$)— or sulfur;

and (b) when K is nitrogen, $R_1$ and $R_2$ (considered together with K, the C* atom, and the bond joining K and C*), form a fused ring selected from one of:

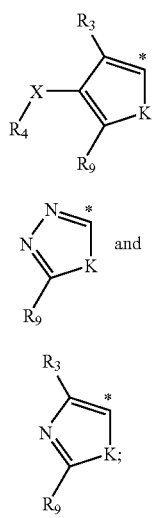

provided, however, that when J and K are both nitrogen, $R_1$ and $R_2$ do not form ring ($T_1$); and provided further that when J is N, K is carbon, and $R_1$ and $R_2$ form ring ($S_1$), then Z is —C(=O)$NR_{11}R_{12}$;

X is selected from —O—, —OC(=O)—, —S—, —S(=O)—, —$SO_2$—, —C(=O)—, —$CO_2$—, —$NR_{15}$—, —$NR_{15}$C(=O)—, —$NR_{15}$C(=O)$NR_{15a}$—, —$NR_{15}CO_2$—, —$NR_{15}SO_2$—, —$NR_{15}SO_2NR_{15a}$—, —$SO_2NR_{15}$—, —C(=O)$NR_{15}$—, halogen, nitro, and cyano, or X is absent;

$X_1$ is selected from —C(=O)—, —$CO_2$—, —$NR_{15}$—, —$NR_{15}$C(=O)—, —$NR_{15}$C(=O)$NR_{15a}$—, —$NR_{15}CO_2$—, —$NR_{15}SO_2$—, —$NR_{15}SO_2NR_{15a}$—, —$SO_2NR_{15}$—, —C(=O)$NR_{15}$—, and nitro, or $X_1$ is absent;

$R_3$ is hydrogen, methyl, perfluoromethyl, methoxy, halogen, cyano, $NH_2$, or NH($CH_3$);

$R_4$ is selected from:
(a) hydrogen, provided that $R_4$ is not hydrogen if either X is —S(=O)—, —$SO_2$—, —$NR_{15}CO_2$—, or —$NR_{15}SO_2$—, or $X_1$ is —$NR_{15}CO_2$—, or —$NR_{15}SO_2$—;
(b) alkyl, alkenyl, and alkynyl optionally independently substituted with keto and/or one to four $R_{17}$;
(c) aryl and heteroaryl either of which may be optionally independently substituted with one to three $R_{16}$; and
(d) heterocyclo and cycloalkyl either of which may be optionally independently substituted with keto and/or one to three $R_{16}$; or
(e) $R_4$ is absent if X is halogen, nitro, or cyano or if $X_1$ is nitro;

$R_7$ is selected from alkyl, substituted alkyl, aryl, and heteroaryl;

$R_9$ is selected from hydrogen, alkyl, substituted alkyl, halogen, cyano, aryl, heteroaryl, —$SR_{10}$, and —$S(O)_2R_{10}$, wherein $R_{10}$ is alkyl or substituted alkyl;

$R_{11}$ is hydrogen, alkyl, or substituted alkyl;

$R_{12}$, $R_{13}$ and $R_{14}$ are independently selected from hydrogen, alkyl, substituted alkyl, alkenyl, substituted alkenyl, hydroxy, alkoxy, aryl, cycloalkyl, heteroaryl, and heterocyclo, except $R_{14}$ is not hydrogen;

$R_{15}$ and $R_{15a}$ are independently selected from hydrogen, alkyl, substituted alkyl, aryl, cycloalkyl, heterocyclo, and heteroaryl;

$R_{16}$ is selected from alkyl, $R_{17}$, and $C_{1-4}$alkyl substituted with keto (=O) and/or one to three $R_{17}$;

$R_{17}$ is selected from
(a) halogen, haloalkyl, haloalkoxy, nitro, cyano, —$SR_{23}$, —$OR_{23}$, —$NR_{23}R_{24}$, —$NR_{23}SO_2R_{25}$, —$SO_2R_{25}$, —$SO_2NR_{23}R_{24}$, —$CO_2R_{23}$, —C(=O)$R_{23}$, —C(=O)$NR_{23}R_{24}$, —OC(=O)$R_{23}$, —OC(=O)$NR_{23}R_{24}$, —$NR_{23}$C(=O)$R_{24}$, —$NR_{23}CO_2R_{24}$;
(b) aryl or heteroaryl either of which may be optionally substituted with one to three $R_{26}$; or
(c) cycloalkyl or heterocyclo optionally substituted with keto(=O) and/or one to three $R_{26}$;

$R_{23}$, $R_{24}$ and $R_{25}$ are each independently selected from hydrogen, alkyl, alkenyl, substituted alkyl, substituted alkenyl, aryl, cycloalkyl, heteroaryl, and heterocyclo, except $R_{25}$ is not hydrogen;

$R_{26}$ is at each occurrence independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, $C_{1-4}$alkoxy, $C_{1-4}$alkylthio, phenyl, five to six membered heterocyclo, (phenyl)$C_{1-4}$alkyl, phenoxy, and (phenyl)$C_{1-4}$alkoxy; and p is 0, 1, 2 or 3.

The invention further pertains to pharmaceutical compositions containing compounds of formula (I), and to methods of treating conditions associated with the activity of p38 kinase (α and β), comprising administering to a mammal a pharmaceutically-acceptable amount of a compound of formula (I).

DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 12 carbon atoms, preferably 1 to 6 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms. The term "$C_{1-6}$alkoxy" includes methoxy, ethoxy, propyloxy, methoxypentane, ethoxybutane, and so forth.

The term "substituted alkyl" refers to an alkyl group substituted by one to four substituents selected from halogen, hydroxy, alkoxy, keto (=O), alkanoyl, aryloxy, alkanoyloxy, $NR_aR_b$, alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, —$SO_2NR_aR_b$, nitro, cyano, —$CO_2H$, —$CONR_aR_b$, alkoxycarbonyl, aryl, guanidino and heteroaryls or heterocyclos (such as indolyl, imidazolyl, furyl, thienyl, thiazolyl, pyrrolidyl, pyridyl, pyrimidyl and the like), wherein $R_a$ and $R_b$ are selected from hydrogen, alkyl, aryl, aralkyl, cycloalkyl, cycloalkylalkyl, heteroaryl, heteroarylalkyl, heterocycle, and heterocyclealkyl. The substituent on the alkyl optionally in turn may be further substituted, in which case it will be with substituted one or more of $C_{1-4}$alkyl, $C_{2-4}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and/or benzyloxy.

The term "alkenyl" refers to straight or branched chain hydrocarbon groups of 2 to 20 carbon atoms, preferably 2 to 15 carbon atoms, and most preferably 2 to 8 carbon atoms, having at least one double bond, and depending on the number of carbon atoms, up to four double bonds.

The term "substituted alkenyl" refers to an alkenyl group substituted by one to two substituents selected from those recited above for substituted alkyl groups.

The term "alkynyl" refers to straight or branched chain hydrocarbon groups of 2 to 20 carbon atoms, preferably 2 to 15 carbon atoms, and most preferably 2 to 8 carbon atoms, having at least one triple bond, and depending on the number of carbon atoms, up to four triple bonds.

The term "substituted alkynyl" refers to an alkynyl group substituted by one to two substituents selected from those recited above for alkyl groups.

When the term alkyl is used in connection with another group, as in heterocycloalkyl or cycloalkylalkyl, this means the identified (first named) group is bonded directly through an alkyl group which may be branched or straight chain (e.g., cyclopropyl$C_{1-4}$alkyl means a cyclopropyl group bonded through a straight or branched chain alkyl group having one to four carbon atoms.). In the case of substituents, as in "substituted cycloalkylalkyl," the alkyl portion of the group, besides being branched or straight chain, may be substituted as recited above for substituted alkyl groups and/or the first named group (e.g., cycloalkyl) may be substituted as recited herein for that group.

The term "alkoxy" as used herein means an alkyl group as defined above wherein one or more carbon atoms of the hydrocarbon straight or branched chain is replaced by an oxygen atom. Thus, it includes groups such as —OR, wherein R is alkyl, —$(CH_2)_n$—$OCH_3$, —$(CH_2)_{(n-1)}$—$OCH_2CH_3$, wherein n is an integer of 1 to 11, and so forth.

The term "halogen" or "halo" refers to fluorine, chlorine, bromine and iodine.

The term "aryl" refers to monocyclic or bicyclic aromatic substituted or unsubstituted hydrocarbon groups having 6 to 12 carbon atoms in the ring portion, such as phenyl, naphthyl, and biphenyl groups. Aryl groups may optionally include one to three additional rings (either cycloalkyl, heterocyclo or heteroaryl) fused thereto. Examples include:

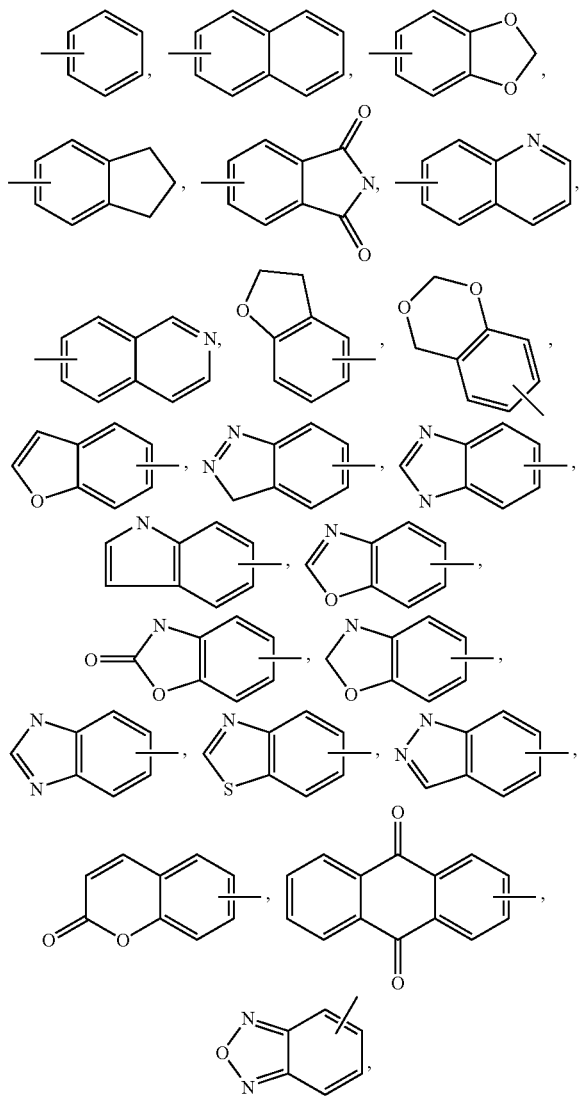

and the like. Each ring of the aryl may be optionally substituted with one to three $R_c$, groups, wherein $R_c$, at each occurrence is selected from alkyl, substituted alkyl, halogen, trifluoromethoxy, trifluoromethyl, —SR, —OR, —NRR', —$NRSO_2R'$, —$SO_2R$, —$SO_2NRR'$, —$CO_2R'$, —C(=O)R', —C(=O)NRR', —OC(=O)R', —OC(=O)NRR', —NRC(=O)R', —NRCO$_2$R', phenyl, C$_{3-7}$ cycloalkyl, and five-to-six membered heterocyclo or heteroaryl, wherein each R and R' is selected from hydrogen, alkyl, substituted alkyl, alkenyl, substituted alkenyl, phenyl, C$_{3-7}$cycloalkyl, and five-to-six membered heterocyclo or heteroaryl, except in the case of a sulfonyl group, then R is not going to be hydrogen. Each substituent R$_c$ optionally in turn may be further substituted by one or more (preferably 0 to 2) R$_d$ groups, wherein R$_d$ is selected from C$_{1-6}$alkyl, C$_{2-6}$alkenyl, halogen, haloalkyl, haloalkoxy, cyano, nitro, amino, C$_{1-4}$alkylamino, aminoC$_{1-4}$alkyl, hydroxy, hydroxyC$_{1-4}$alkyl, alkoxy, alkylthio, phenyl, benzyl, phenylethyl, phenyloxy, and benzyloxy.

The term "aralkyl" refers to an aryl group bonded directly through an alkyl group, such as benzyl, wherein the alkyl group may be branched or straight chain. In the case of a "substituted aralkyl," the alkyl portion of the group besides being branched or straight chain, may be substituted as recited above for substituted alkyl groups and/or the aryl portion may be substituted as recited herein for aryl. Thus, the term "optionally substituted benzyl" refers to the group

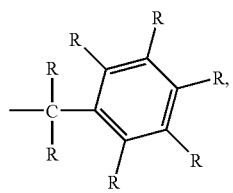

wherein each R group may be hydrogen or may also be selected from R$_c$, as defined above, in turn optionally substituted with one or more R$_d$. At least two of these "R" groups should be hydrogen and preferably at least five of the "R" groups is hydrogen. A preferred benzyl group involves the alkyl-portion being branched to define

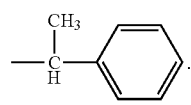

The term "heteroaryl" refers to a substituted or unsubstituted aromatic group for example, which is a 4 to 7 membered monocyclic, 7 to 11 membered bicyclic, or 10 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. It may optionally be substituted as valance allows with one to three (preferably 0 to 2) R$_c$ groups, as defined above for aryl, which in turn may be substituted with one or more (preferably 0 to 2) R$_d$ groups, also as recited above. Additionally, a heteroaryl group may be an aromatic, heterocyclic group as defined above wherein one or two carbon atoms of the ring, as valence allows, is replaced with a carbonyl group, wherein the heteroaryl ring then may be partially unsaturated with the carbonyl group imparting aromaticity to the ring, e.g., as in a group 2,4-dihydro-[1,2,4]triazol-3-one.

Exemplary monocyclic heteroaryl groups include pyrrolyl, pyrazolyl, pyrazolinyl, imidazolyl, oxazolyl, isoxazolyl, thiazolyl (i.e., 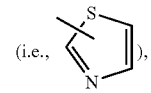), thiadiazolyl, isothiazolyl, furanyl, thienyl, oxadiazolyl, pyridyl, pyrazinyl, pyrimidinyl, pyridazinyl, triazinyl and the like. Additionally, heteroaryl groups include groups such as 2,4-dihydro-[1,2,4]triazol-3-one (i.e., 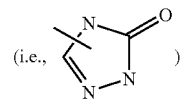 )

and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "cycloalkyl" refers to a saturated or partially unsaturated non-aromatic cyclic hydrocarbon ring system, preferably containing 1 to 3 rings and 3 to 7 carbon atoms per ring, which may be substituted or unsubstituted and/or which may be fused with a C$_3$-C$_7$ carbocylic ring, a heterocyclic ring, or which may have a bridge of 3 to 4 carbon atoms. The cycloalkyl groups including any available carbon or nitrogen atoms on any fused or bridged rings optionally may have 0 to 3 (preferably 0-2) substituents selected from R$_c$, groups, as recited above, and/or from keto (where appropriate) which in turn may be substituted with one to three R$_d$ groups, also as recited above. Thus, when it is stated that a carbon-carbon bridge may be optionally substituted, it is meant that the carbon atoms in the bridged ring optionally may be substituted with an R$_c$, group, which preferably is selected from C$_{1-4}$alkyl, C$_{2-4}$alkenyl, halogen, haloalkyl, haloalkoxy, cyano, amino, C$_{1-4}$alkylamino, aminoC$_{1-4}$alkyl, hydroxy, hydroxyC$_{1-4}$alkyl, and C$_{1-4}$alkoxy. Exemplary cycloalkyl groups include cyclopropyl, cyclobutyl, cyclopentyl, cyclohexyl, cycloheptyl, bicycloheptane, cycloctyl, cyclodecyl, cyclododecyl, and adamantyl.

The terms "heterocycle", "heterocyclic" and "heterocyclo" each refer to a fully saturated or partially unsaturated non-aromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. The heterocyclic group may be attached at any nitrogen or carbon atom. The heterocyclo groups optionally may have 0 to 3 (preferably 0-2) substituents selected from keto (=O), and/or one or more $R_c$, groups, as recited above, which in turn may be substituted with one to three $R_d$ groups, also as recited above.

Exemplary monocyclic heterocyclic groups include pyrrolidinyl, tetrahydrofuryl, piperidinyl, piperazinyl, tetrahydropyranyl, morpholinyl, thiamorpholinyl, and the like.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., oxadiazolyl), the reference is intended to include rings having, as valence allows, 0 to 3, preferably 0-2, substituents, selected from those recited above for the aryl, cycloalkyl, heterocyclo and/or heteroaryl groups, as appropriate. Thus, for example, an "optionally-substituted oxadiazolyl" means an oxadiazolyl ring that is unsubstituted or substituted with one group selected from the $R_c$, groups, as defined above for aryl, which in turn may be substituted with one or more (preferably 0 to 2) $R_d$ groups, also as recited above.

Additionally, when reference is made to a specific heteroaryl or heterocyclo group, the reference is intended to include those systems having the maximum number of non-cumulative double bonds or less than the maximum number of double bonds. Thus, for example, the term "isoquinoline" refers to isoquinoline and tetrahydroisoquinoline.

Additionally, it should be understood that one skilled in the field may make appropriate selections for the substituents for the aryl, cycloalkyl, heterocyclo, and heteroaryl groups to provide stable compounds and compounds useful as pharmaceutically-acceptable compounds and/or intermediate compounds useful in making pharmaceutically-acceptable compounds. Thus, for example, in compounds of formula (I), when B is a cyclopropyl ring, preferably the ring has no more than two substituents, and preferably said substituents do not comprise nitro ($NO_2$), more than one cyano group, or three halogen groups. Similarly, when m is 3, preferably $R_6$, the substituents on the phenyl ring A, are not all nitro, and so forth.

The term "heteroatoms" shall include oxygen, sulfur and nitrogen.

The term "haloalkyl" means an alkyl having one or more halo substituents.

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, aryl, cycloalkyl, and so forth, are as follows: alkanoyl is —C(=O)$R^e$, aryloxy is —OAr, alkanoyloxy is —OC(=O)$R^e$, amino is —$NH_2$, alkylamino is —$NHR^e$ or —N($R^e$)$_2$, arylamino is —NHAr or —$NR^e$Ar, aralkylamino is —NH—$R^f$—Ar, alkanoylamino is —NH—C(=O)$R^e$, aroylamino is —NH—C(=O)Ar, aralkanoylamino is —NH—C(=O)$R^f$—Ar, thiol is —SH, alkylthio is —$SR^e$, arylthio is —SAr, aralkylthio is —S—$R^f$—Ar, alkylthiono is —S(=O)$R^e$, arylthiono is —S(=O)Ar, aralkylthiono is —S(=O)$R^f$—Ar, alkylsulfonyl is —$SO_{(q)}R^e$, arylsulfonyl is —$SO_{(q)}$Ar, arylsulfonylamine is —$NHSO_{(q)}$Ar, alkylsulfonylamine is —$NHSO_2R^e$, aralkylsulfonyl is —$SO_{(q)}R^f$Ar, sulfonamido is —$SO_2NH_2$, substituted sulfonamide is —$SO_2NHR^e$ or —$SO_2N(R^e)_2$, nitro is —$NO_2$, carboxy is —$CO_2H$, carbamyl is —$CONH_2$, substituted carbamyl is —C(=O)$NHR^g$ or —C(=O)$NR^gR^h$, alkoxycarbonyl is —C(=O)$OR^e$, carboxyalkyl is —$R^f$—$CO_2H$, sulfonic acid is —$SO_3H$, arylsulfonylamine is —$NHSO_{(q)}$Ar, guanidino is

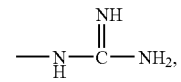

and ureido is

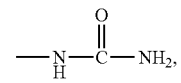

wherein $R^e$ is alkyl or substituted alkyl as defined above, $R^f$ is alkylene or substituted alkylene as defined above, $R^g$ and $R^h$ are selected from alkyl, substituted alkyl, aryl, aralkyl, cycloalkyl, heterocyclo, and hetaryl; Ar is an aryl as defined above, and q is 2 or 3.

Throughout the specification, groups and substituents thereof may be chosen by one skilled in the field to provide stable moieties and compounds.

The compounds of the present invention may form salts which are also within the scope of this invention. Pharmaceutically acceptable (i.e. non-toxic, physiologically acceptable) salts are preferred, although other salts are also useful, e.g. in isolating or purifying the compounds of this invention.

The compounds of the present invention may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the present invention may also have prodrug forms. Any compound that will be converted in vivo to provide the bioactive agent (i.e., the compound for formula (I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

It should further be understood that solvates (e.g., hydrates) of the compounds of Formula (I) are also with the scope of the present invention. Methods of solvation are generally known in the art.

Preferred Compounds

While the scope of the invention is defined in the Summary of Invention and claims, and equivalents thereof, certain embodiments are preferred. In particular, preferred compound are those having the formula (I),

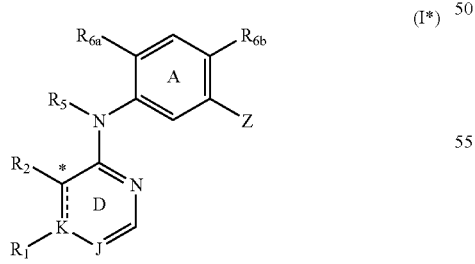
(I*)

their enantiomers, diastereomers, and pharmaceutically-acceptable salts, prodrugs, and solvates thereof, wherein:

J, K, $R_1$ and $R_2$ are selected such that ring D and the ring fused thereto as defined by $R_1$ and $R_2$ form a bicyclic group selected from one of:

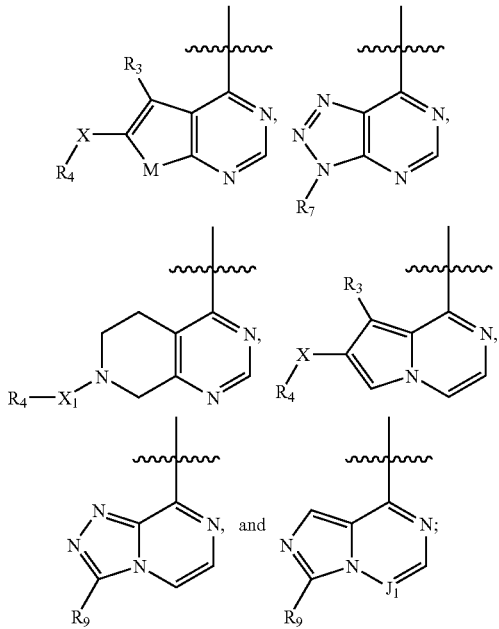

wherein M is —N($R_7$)— or —S—;

$J_1$ is nitrogen or CH;

X is selected from —C(=O)—, —C(=O)—O—, —S(O)$_2$—, —S(O)$_2$NR$_{14}$—, and —C(=O)NR$_{14}$—; and $X_1$ is selected from —C(=O)— and —C(=O)NR$_{14}$—, wherein $R_{14}$ is hydrogen or alkyl;

Z is selected from —NHR$_{11}$, —C(=O)NR$_{11}$R$_{12}$, —NR$_{11}$C(O)$_2$R$_{12}$, —NR$_{11}$SO$_2$R$_{14}$, —SO$_2$NR$_{12}$, —C(=O)R$_{12}$, —OC(=O)R$_{15}$, —C(=O)NR$_{11}$C(=O)R$_{13}$, —C(=O)NR$_{11}$C(=O)NR$_{12}$R$_{13}$, and optionally-substituted heteroaryl;

$R_3$ is hydrogen, methyl, perfluoromethyl, methoxy, halogen, cyano, NH$_2$, or NH(CH$_3$);

$R_4$ is selected from:
(a) hydrogen, provided that $R_4$ is not hydrogen if X is —S(=O)—, —SO$_2$—, —NR$_{15}$CO$_2$—, or —NR$_{15}$SO$_2$—;
(b) alkyl, alkenyl, and alkynyl optionally independently substituted with keto and/or one to four $R_{17}$;
(c) aryl and heteroaryl either of which may be optionally independently substituted with one to three $R_{16}$; and
(d) heterocyclo and cycloalkyl either of which may be optionally independently substituted with keto and/or one to three $R_{16}$; or
(e) $R_4$ is absent if X is halogen, nitro, or cyano;

$R_5$ is hydrogen or $C_{1-4}$alkyl;

$R_{6a}$ and $R_{6b}$ are independently selected from hydrogen, $C_{1-4}$alkyl, hydroxy, methoxy, halogen, cyano, amino, —NH(C$_{1-4}$alkyl), —N(C$_{1-4}$alkyl)$_2$, —CF$_3$, —OCF$_3$, and $C_{1-4}$alkyl substituted with one or two of hydroxy, methoxy, halogen, cyano, amino, —NH(C$_{1-4}$alkyl), —N(C$_{1-4}$alkyl)$_2$-CF$_3$, and/or —OCF$_3$;

$R_7$ is selected from alkyl, substituted alkyl, aryl, and heteroaryl;

$R_9$ is selected from alkyl, substituted alkyl, halogen, cyano, aryl, heteroaryl, —SR$_{10}$, and —S(O)$_2$R$_{10}$, wherein $R_{10}$ is alkyl or substituted alkyl;

$R_{11}$ is hydrogen, alkyl, or substituted alkyl;

$R_{12}$, $R_{13}$ and $R_{14}$ are independently selected from hydrogen, alkyl, substituted alkyl, alkenyl, substituted alkenyl, hydroxy, alkoxy, aryl, cycloalkyl, heteroaryl, and heterocyclo, except $R_{14}$ is not hydrogen;

$R_{15}$ and $R_{15a}$ are independently selected from hydrogen, alkyl, substituted alkyl, aryl, cycloalkyl, heterocyclo, and heteroaryl;

$R_{16}$ is selected from alkyl, $R_{17}$, and $C_{1-4}$alkyl substituted with keto (=O) and/or one to three $R_{17}$;

$R_{17}$ is selected from
(a) halogen, haloalkyl, haloalkoxy, nitro, cyano, —$SR_{23}$, —$OR_{23}$, —$NR_{23}R_{24}$, —$NR_{23}SO_2R_{25}$, —$SO_2R_{25}$, —$SO_2NR_{23}R_{24}$, —$CO_2R_{23}$, —$C(=O)R_{23}$, —$C(=O)NR_{23}R_{24}$, —$OC(=O)R_{23}$, —$OC(=O)NR_{23}R_{24}$, —$NR_{23}C(=O)R_{24}$, —$NR_{23}CO_2R_{24}$;
(b) aryl or heteroaryl either of which may be optionally substituted with one to three $R_{26}$; or
(c) cycloalkyl or heterocyclo optionally substituted with keto(=O) and/or one to three $R_{26}$;

$R_{23}$, $R_{24}$ and $R_{25}$ are each independently selected from hydrogen, alkyl, alkenyl, substituted alkyl, substituted alkenyl, aryl, cycloalkyl, heteroaryl, and heterocyclo, except $R_{25}$ is not hydrogen; and $R_{26}$ is at each occurrence independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, $C_{1-4}$alkoxy, $C_{1-4}$alkylthio, phenyl, five to six membered heterocyclo, (phenyl)$C_{1-4}$alkyl, phenoxy, and (phenyl)$C_{1-4}$alkoxy.

Preferably, in compounds of formula I, as described immediately above, when J is N, K is carbon, and $R_1$ and $R_2$ form a thieno or pyrrolo ring (as in $S_1$ herein), then Z is not —$NHR_{11}$, —$NR_{11}C(O)_2R_{12}$, —$NR_{11}C(=O)R_{13}$, or —$NR_{11}C(=O)NR_{12}R_{13}$. More preferably, in such cases Z is —$C(=O)NR_{11}R_{12}$. Even more preferably, in such cases, Z is —$C(=O)NR_{11}R_{12}$ and X is $C(=O)$— or —$C(=O)NR_{14}$—, wherein $R_{14}$ is hydrogen or alkyl.

Preferably, in compounds of formula I, as described immediately above, when J is N, K is carbon, and $R_1$ and $R_2$ form a triazolo ring (as in $S_2$ herein), then Z is not —$NHR_{11}$, —$NR_{11}C(O)_2R_{12}$, —$NR_{11}C(=O)R_{13}$, or —$NR_{11}C(=O)NR_{12}R_{13}$. More preferably, in such cases $R_7$ is phenyl and Z is —$C(=O)NR_{11}R_{12}$.

According to another aspect of the invention, preferred compounds are those having the formula (I*), as immediately defined above, wherein:
$R_3$ is hydrogen, methyl, —$CF_3$, or —$OCF_3$;
$R_5$ is hydrogen;
X is —$C(=O)$—, —$NR_{14}C(=O)$—, or —$C(=O)NR_{14}$—, and $X_1$ is —$C(=O)$— or —$C(=O)NR_{14}$—, wherein $R_{14}$ is hydrogen or $C_{1-4}$alkyl;
Z is as defined above;
$R_4$ is hydrogen, $C_{2-6}$alkyl, $C_{1-4}$alkyl optionally substituted with one to three $R_{17}$, aryl or heteroaryl optionally substituted with one to three $R_{16}$, or cycloalkyl or heterocycle optionally-substituted with keto (=O) and/or one to three $R_{16}$;
$R_{6a}$ is methyl;
$R_{6b}$ is hydrogen;
and the remaining groups, i.e., $R_7$, $R_9$, $R_{11}$, $R_{12}$, $R_{13}$, $R_{14}$, $R_{15}$, $R_{16}$, $R_{17}$, $R_{23}$, $R_{24}$, $R_{25}$, and $R_{26}$, are defined as immediately above.

In compounds of formula (I), preferably $R_3$ is methyl, —$CF_3$, or —$OCF_3$, more preferably methyl; X preferably is —$C(=O)$— or —$C(=O)NH$—; and Z is preferably —$C(=O)NR_{11}R_{12}$, wherein $R_{11}$, is hydrogen or $C_{1-4}$alkyl, and $R_{12}$ is selected from $C_{1-4}$alkyl, $C_{1-4}$alkoxy, and cyclopropyl, more preferably cyclopropyl.

Preferably when X is —$C(=O)NH$—, $R_4$ is $C_{2-6}$alkyl or substituted $C_{1-4}$alkyl, more preferably $C_{1-4}$alkyl or optionally-substituted benzyl. When X is —$C(=O)$—, preferably $R_4$ is an optionally-substituted aryl or heteroaryl.

When $R_4$ is a heterocyclo, advantageously it is selected from diazepinyl, morpholinyl, piperidinyl, and pyrrolidinyl, said heterocycle being optionally substituted with one to two of $C_{1-4}$alkyl, hydroxy, $C_{1-4}$alkoxy, phenyl, and/or benzyl. When X is —$C(=O)$— and $R_4$ is aryl or heteroaryl, preferably $R_4$ is phenyl, pyridinyl, pyrimidinyl, or pyrazinyl, optionally-substituted with $C_{1-4}$alkyl, halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}$alkyl), $N(C_{1-4}$alkyl)$_2$, cyclopentyl, cyclohexyl, or five or six membered heteroaryl or heterocycle.

According to another aspect of the invention, a subset of preferred compounds are those having the formula I (S1),

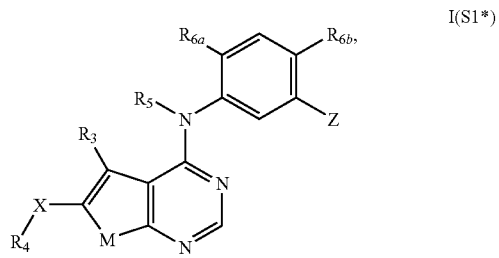

I(S1*)

or pharmaceutically-acceptable salts, prodrugs, or solvates thereof, wherein the groups X, $R_3$, $R_4$, $R_5$, $R_{6a}$, $R_{6b}$, and Z are defined as above, more preferably wherein these groups are selected from preferred selections for such groups recited herein. For example, within this subset of preferred compounds, more preferred are those having the formulae I (S1*) or I (S1**):

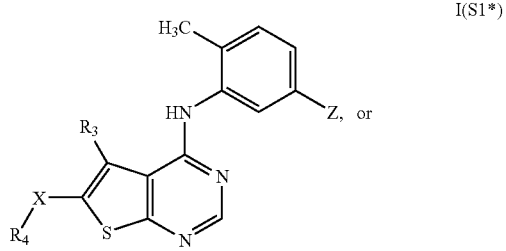

I(S1*)

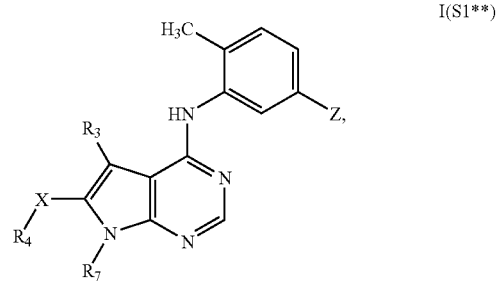

I(S1**)

wherein X is —$C(=O)$—O— or —$C(=O)NH$— (attached to the thieno group via the carbonyl), or is absent; $R_3$ is methyl, —$CF_3$, or —$OCF_3$; $R_4$ is selected from hydrogen, C$_{1-6}$alkyl, C$_{1-6}$alkoxy, C$_{3-7}$cycloalkyl, heterocyclo (more preferably N-morpholinyl), and C$_{1-4}$alkyl substituted with optionally substituted phenyl or pyridyl; R$_7$ is phenyl or pyridyl (more preferably phenyl); and Z is —C(=O)NR$_{11}$R$_{12}$, wherein R$_{11}$ is hydrogen or C$_{1-4}$alkyl, and R$_{12}$ is selected from C$_{1-4}$alkyl, C$_{1-4}$alkoxy, and cyclopropyl (more preferably cyclopropyl).

According to another aspect of the invention, a subset of preferred compounds are those having the formula I (S2),

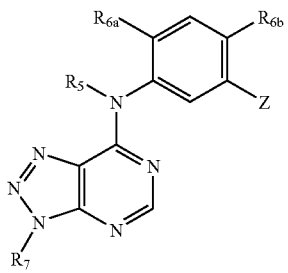

I(S2)

or pharmaceutically-acceptable salts, prodrugs, or solvates thereof, wherein the groups R$_5$, R$_7$, R$_{6a}$, R$_{6b}$, and Z are defined as above, more preferably wherein these groups are selected from the preferred selections for such groups recited herein. For example, within this subset of preferred compounds, particularly preferred are those having the formula I (S2*):

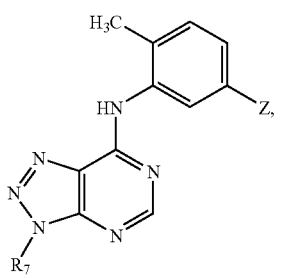

I(S2*)

or pharmaceutically-acceptable salts, prodrugs, or solvates thereof, wherein R$_7$ is optionally-substituted phenyl or pyridyl (more preferably phenyl); and Z is —C(=O)NR$_{11}$R$_{12}$, wherein R$_{11}$, is hydrogen or C$_{1-4}$alkyl and R$_{12}$ is C$_{1-4}$alkyl, C$_{1-4}$alkoxy, or cyclopropyl (more preferably cyclopropyl).

According to another aspect of the invention, a subset of preferred compounds are those having the formula I (S3),

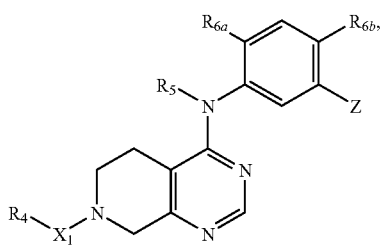

I(S3)

or pharmaceutically-acceptable salts, prodrugs, or solvates thereof, wherein the groups X$_1$, R$_4$, R$_5$, R$_{6a}$, R$_{6b}$, and Z are defined as above, more preferably wherein these groups are selected from preferred selections for such groups recited herein. For example, within this subset of preferred compounds, particularly preferred are those having the formulae I (S3*):

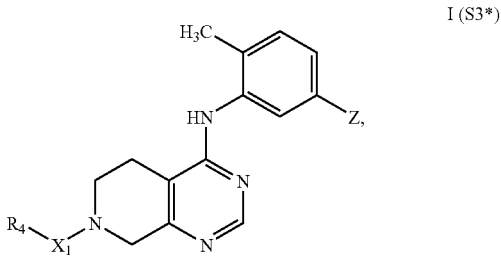

I(S3*)

or pharmaceutically-acceptable salts, prodrugs, or solvate thereofs, wherein: X$_1$ is selected from —C(=O)— and —C(=O)NR$_{14}$—, wherein R$_{14}$ is hydrogen or alkyl (more preferably H or C$_{1-4}$alkyl); R$_4$ is selected from (a) C$_{1-6}$alkyl optionally substituted with aryl, heteroaryl or heterocyclo (more preferably phenyl or morpholinyl), said rings (e.g., phenyl or morpholinyl) in turn optionally substituted with one to two R$_{26}$, and (b) heteroaryl or heterocyclo (more preferably imidazolyl, pyrazolyl, pyridyl, phenyl, or morpholinyl), in turn optionally substituted with one to three of R$_{16}$; Z is —C(=O)NR$_{11}$R$_{12}$, wherein R$_{11}$, is hydrogen or C$_{1-4}$alkyl, and R$_{12}$ is C$_{1-4}$alkyl, C$_{1-4}$alkoxy, or cyclopropyl (more preferably cyclopropyl); and R$_{16}$ and R$_{26}$ at each occurrence are independently selected from C$_{1-4}$alkyl, halogen, cyano, C$_{1-4}$alkoxy, —CF$_3$, and/or —OCF$_3$.

According to another aspect of the invention, a subset of preferred compounds are those having the formula I (T1),

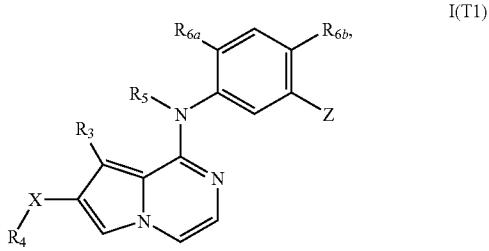

I(T1)

or pharmaceutically-acceptable salts, prodrugs, or solvates thereof, wherein the groups X, R$_3$, R$_4$, R$_5$, R$_{6a}$, R$_{6b}$, and Z are defined as above, more preferably wherein these groups are selected from the preferred selections for such groups recited herein. For example, within this subset of preferred compounds, particularly preferred are those having the formulae I (T1*):

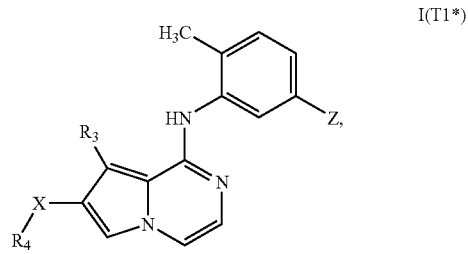

I(T1*)

or pharmaceutically-acceptable salts, prodrugs, or solvate thereofs, wherein R$_3$ is hydrogen, methyl, CF$_3$, or —OCF$_3$; X is —C(=O)NR$_{14}$— (attached to the pyrrolyl group via the carbonyl), wherein R$_{14}$ is hydrogen or alkyl (more preferably H or C$_{1-4}$alkyl); R$_4$ is selected from C$_{1-6}$alkyl, benzyl, C$_{1-6}$alkoxy, C$_{3-7}$cycloalkyl, and heterocyclo (more preferably N-morpholinyl); and Z is selected from —NHR$_{11}$, —C(=O)NR$_{11}$R$_{12}$, —NR$_{11}$C(O)$_2$R$_{12}$, —NR$_{11}$(C=O)R$_{13}$, and —NR$_{11}$(C=O)NR$_{12}$, wherein R$_{11}$ is hydrogen or C$_{1-4}$alkyl; R$_{12}$ is C$_{1-4}$alkyl, C$_{1-4}$alkoxy, cyclopropyl, or halo (C$_{1-4}$alkyl); and R$_{13}$ is selected from phenyl and pyridyl in turn optionally substituted by one to three R$_{26}$, wherein R$_{26}$ is selected from halogen, cyano, and morpholinyl. More preferably in such cases Z is —C(=O)NR$_{11}$R$_{12}$, wherein R$_{11}$ is hydrogen or C$_{1-4}$alkyl, and R$_{12}$ is C$_{1-4}$alkyl, C$_{1-4}$alkoxy, or cyclopropyl (more preferably cyclopropyl).

According to another aspect of the invention, a subset of preferred compounds are those having the formula I (T2),

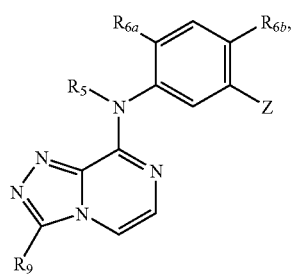

I (T2)

or pharmaceutically-acceptable salts, prodrugs, or solvates thereof, wherein the groups R$_5$, R$_{6a}$, R$_{6b}$, R$_9$, and Z are defined as above, more preferably wherein these groups are selected from preferred selections for such groups recited herein. For example, within this subset of preferred compounds, particularly preferred are those having the formulae I (T2*):

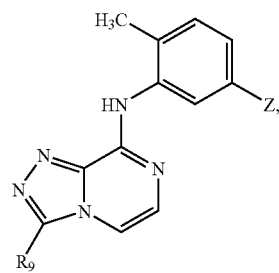

I (T2*)

or a pharmaceutically-acceptable salt, prodrug, or solvate thereof, wherein R$_9$ is alkyl, substituted alkyl, aryl or heteroaryl (more preferably C$_{1-6}$alkyl or phenyl); and Z is —C(=O)NR$_{11}$R$_{12}$, wherein R$_{11}$ is hydrogen or C$_{1-4}$alkyl and R$_{12}$ is C$_{1-4}$alkyl, C$_{1-4}$alkoxy, cyclopropyl, or a heteroaryl selected from pyrazolyl, oxazolyl, and isoxazolyl in turn optionally substituted with C$_{1-4}$alkyl. More preferably Z is C(=O)NR$_{11}$R$_{12}$, wherein R$_{11}$ is hydrogen and R$_{12}$ is cyclopropyl.

According to another aspect of the invention, a subset of preferred compounds are those having the formula I (T3),

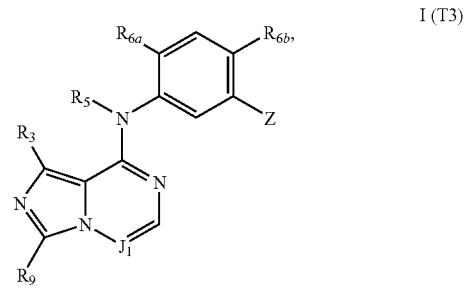

I (T3)

or pharmaceutically-acceptable salts, prodrugs, or solvates thereof, wherein the groups X, R$_4$, R$_5$, R$_{6a}$, R$_{6b}$, J$_1$, and Z are defined as above, more preferably wherein these groups are selected from preferred selections for such groups recited herein. For example, within this subset of preferred compounds, particularly preferred are those having the formulae I (T3*):

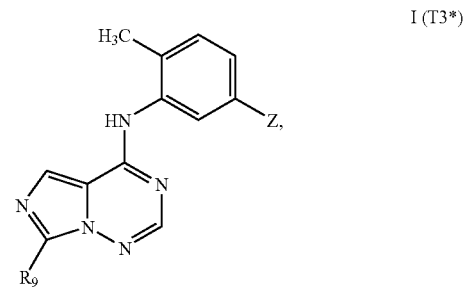

I (T3*)

or pharmaceutically-acceptable salts, prodrugs, or solvates thereof, wherein R$_9$ is selected from halogen, C$_{1-6}$alkyl, phenyl, —SR$_{10}$, and —S(O)$_2$R$_{10}$, wherein R$_{10}$ is C$_{1-4}$alkyl; Z is —C(=O)NR$_{11}$R$_{12}$ or oxadiazolyl optionally substituted with C$_{1-4}$alkyl, wherein R$_{11}$ is hydrogen or C$_{1-4}$alkyl, and R$_{12}$ is C$_{1-4}$alkyl, cyclopropyl, or a heteroaryl (more preferably a heteroaryl selected from pyrazolyl, oxazolyl, and isoxazolyl), in turn optionally substituted with halogen, cyano, or C$_{1-4}$alkyl (more preferably methyl). More preferably in such cases, R$_9$ is phenyl and Z is C(=O)NR$_{11}$R$_{12}$, wherein R$_{11}$ is hydrogen and R$_{12}$ is cyclopropyl.

Utility

The compounds of the invention are selective inhibitors of p38 kinase activity, and in particular, isoforms p38α and p38β. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an IC$_{50}$ value for inhibiting p-38α/β kinase means that the compound has such effectiveness for inhibiting at least one of, or both of, p38α and p38β kinases.

In view of their activity as inhibitors of p-38α/β kinase, compounds of Formula (I) are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The present invention thus provides methods for treating such conditions, comprising administering to a subject in need thereof an effective amount of at least one compound of Formula (I) or a salt thereof. The methods of treating p38 kinase-associated conditions may comprise administering compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g. excipients, binders, preservatives, stabilizers, flavors, etc.) according to techniques such as those well known in the art of pharmaceutical formulation.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®) Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of formula (I), including the compounds described in the examples hereof, have been tested in one or more of the assays described below and have shown activity as inhibitors of p38α/β and enzymes and TNF-α.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5\times10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 µl prepared from three 20 µl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 µl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 11 µM; [γ-$^{33}$P]ATP, 3 nM; MBP (Sigma, #M1891), 2 µg/well; p38, 10 nM; and DMSO, 0.3%.

TNF-α Production by LPS-Stimulated Mice

Mice (Balb/c female, 6-8 weeks of age, Harlan Labs; n=8/treatment group) were injected intraperitoneally with 50 ug/kg lipopolysaccharide (LPS; *E coli* strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

Abbreviations

For ease of reference, the following abbreviations are employed herein, including the methods of preparation and Examples that follow:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
DCM=dichloromethane
DCE=1,2-dichloroethane
DMF=dimethyl formamide
DMSO=dimethyl sulfoxide
TEA=triethylamine
TFA=trifluoroacetic acid
THF=tetrahydrofuran
HATU=O-(7-Azabenzotriazol-1-yl-N,N,N',N'-tetramethyluronim hexafluorophosphate
$POCl_3$=phosphorous oxychloride
EDC or EDCI=1-(3-Dimethylaminopropyl)-3-ethylcarbodiimide hydrochloride
DIPEA=diisopropylethylamine
HATU=O-(7-azabenzotriazol-1-yl)-N,N,N',N'-tetramethyluronium hexafluorphosphate
HOAt=1-hydroxy-7-azabenzotriazole
HOBt or HOBT=1-hydroxybenzotriazole hydrate
m-CPBA=m-chloroperbenzoic acid
NaOH=sodium hydroxide
Pd=palladium
Pd/C=palladium on carbon
min=minute(s)
L=liter
mL=milliliter
µL=microliter
g=gram(s)
mg=milligram(s)
mol=moles
mmol=millimole(s)
meq=milliequivalent
R. B.=round bottom
RT or rt.=room temperature
ret. t. =HPLC retention time (minutes)
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point

Methods of Preparation

Compounds of formula I may generally be prepared according to the schemes and the knowledge of one skilled in the art, and/or the methods described in U.S. patent application Ser. Nos. 10/036,293, 09/573,829, and/or 10/420,399, incorporated herein by reference.

Methods of Preparation

Compounds of formula I may generally be prepared according to the following schemes and the knowledge of one skilled in the art, and/or the methods described in U.S. patent application Ser. Nos. 10/036,293 and/or 09/573,829, incorporated herein by reference. In the schemes, the groups B, $R_3$—$R_6$, and m correspond to variable groups as described herein for compounds of Formula (I) (e.g., group B corresponds to $R_{12}$, $R_a$ corresponds to X—$R_4$, Q is a bicyclic core group as set forth in the claims, m is 0, 1 or 2, and so forth).

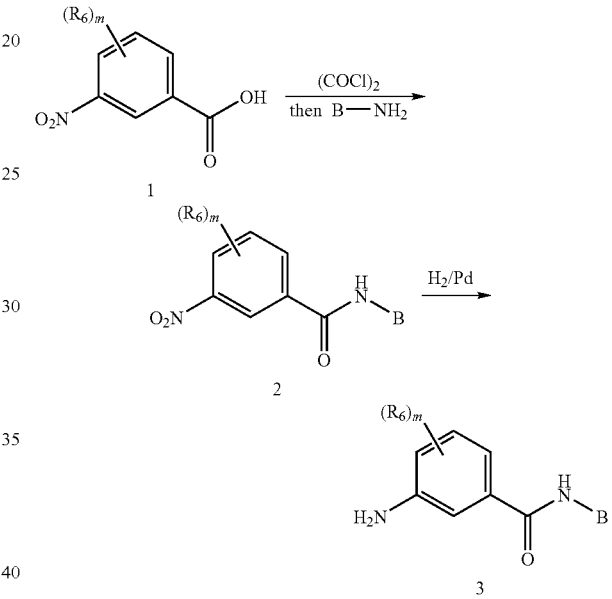

Scheme 1

Commercially-available compound (1) can be reacted with oxalyl chloride with heating and then concentrated in vacuo and reacted with an amine B—$NH_2$ in the presence of a base, such as diisopropylamine, in an organic solvent, such as DCM to yield compound (2). Compound (2) can be reacted with hydrogen in the presence of a catalyst, such as Pd, in an alcoholic solvent, such as EtOH, at rt to afford compound (3). Compound (3) can then be used as in Scheme 2 to produce compounds (7) of Scheme 2.

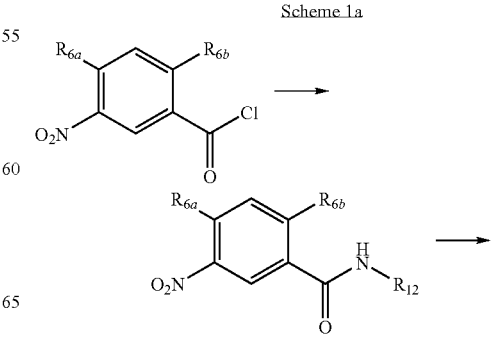

Scheme 1a

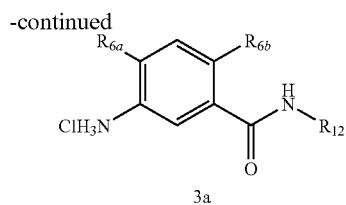

Compound 3a can be prepared as outlined in Scheme 1a by reacting a 3-nitro-benzoyl chloride and an amine $NH_2R_2$ in a solvent, such as dichloromethane, to give a nitro intermediate. This nitro intermediate can be reacted under reducing conditions, such as hydrogen gas and a catalyst, in a solvent to produce an aniline intermediate. This aniline intermediate can be reacted with hydrogen chloride to produce compound 7 as a hydrochloride salt.

Scheme 1b

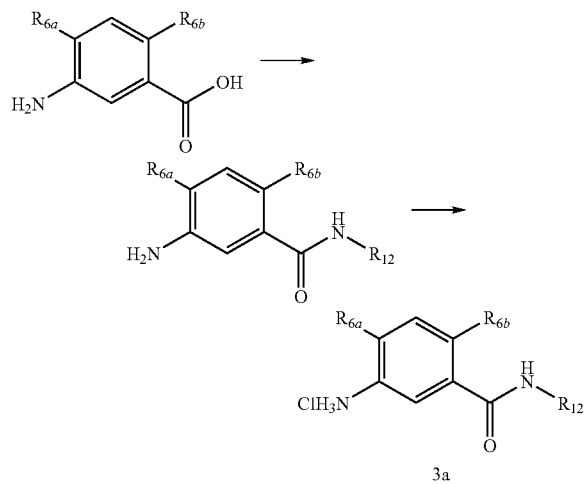

Alternatively to Schemes 1 and 1a, Compound 3a can be prepared as outlined in Scheme 1b, by reacting a 3-aminobenzoic acid and an amine $NH_2R_2$ with a coupling agent, such as EDCI/HOBt, in a suitable solvent and reacting that aniline intermediate with HCl to produce compound 3a as a hydrochloride salt.

Scheme 2

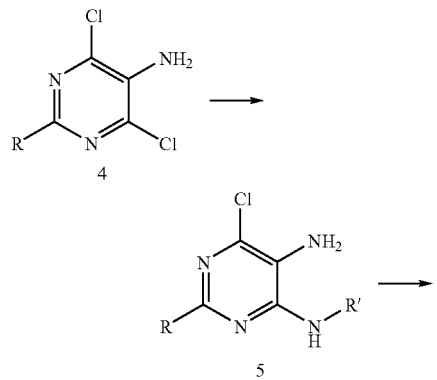

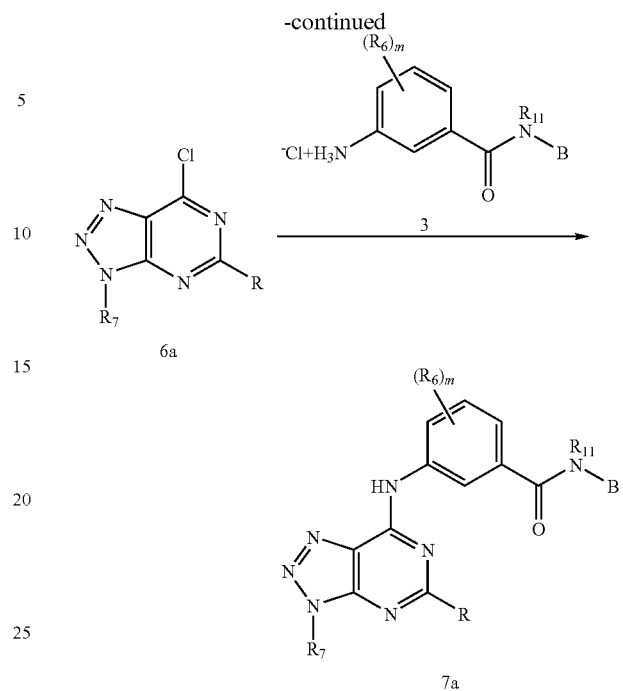

Triazolopyrimidine (6a) prepared according to the procedure described in the literature (*J. Chem. Soc.*(C), [1967] at p. 1856) can be reacted with compound (3) at elevated temperature to produce compound (7a). Compound (3) can be prepared by 1) reacting commercially-available 4-amino-3-methylbenzoic acid and N-(tert-butoxycarbonyl) anhydride in THF to produce a Boc-protected aniline intermediate; 2) reacting the aniline intermediate with -(3-dimethylaminopropyl)-3-ethylcarbodiimide hydrochloride, HOBt, and DMF, followed by addition of methoxyamine hydrochloride and DIPEA to produce a BOC-protected N-methoxyamide intermediate; and 3) reacting that methoxyamide intermediate in a solution of HCl in dioxane to produce compound (3) as a hydrochloride salt. Alternatively, compound (3) can be prepared as shown in Scheme 1.

Scheme 3

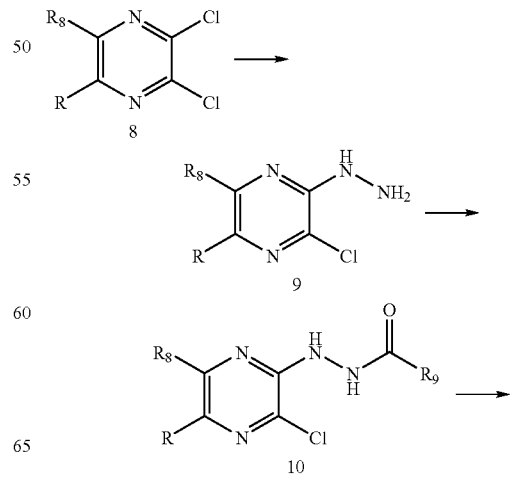

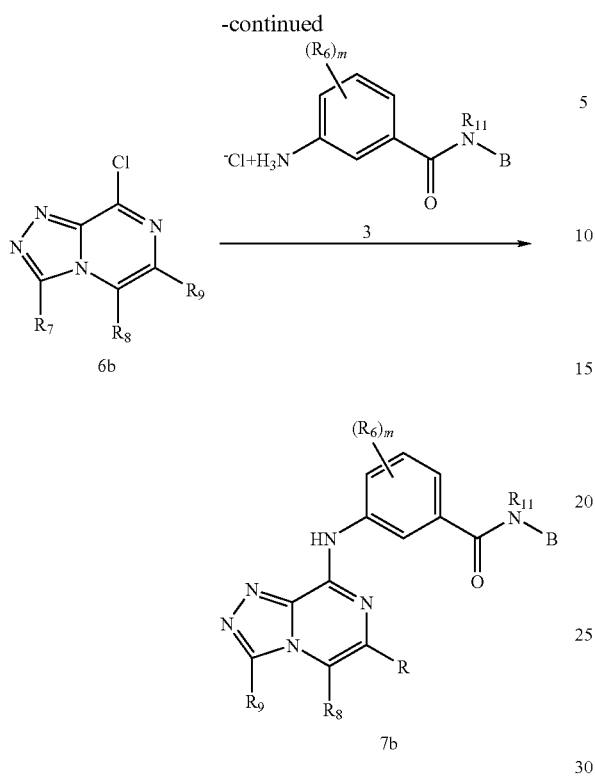

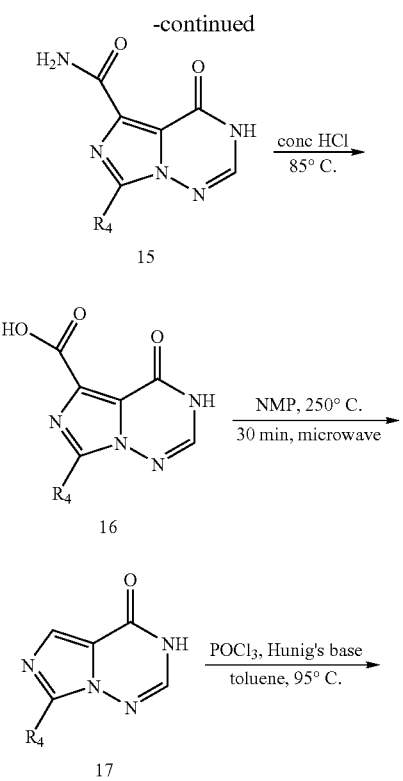

Triazolopyrazine 6b prepared according to the procedure described in the literature (French Patent FR2662163 [1991]) can be reacted with compound (3) at elevated temperature to produce compound (7b). Preparation of compound (7b) can be carried out under microwave conditions using identical conditions.

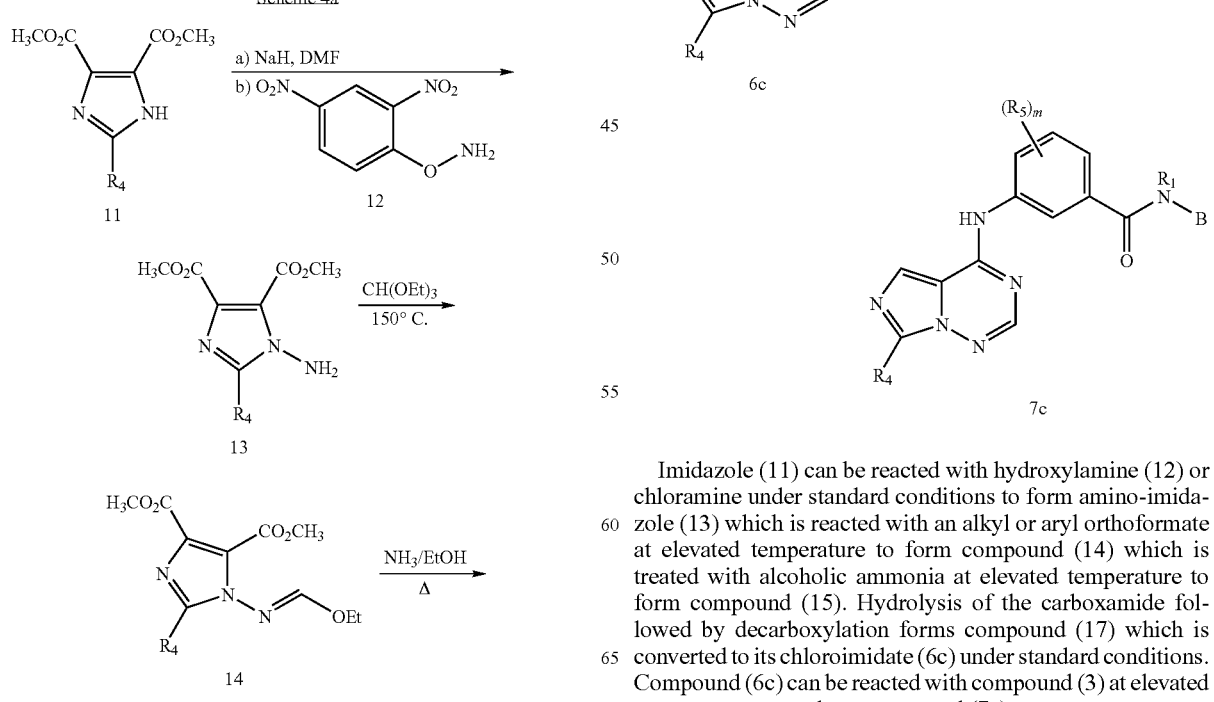

Imidazole (11) can be reacted with hydroxylamine (12) or chloramine under standard conditions to form amino-imidazole (13) which is reacted with an alkyl or aryl orthoformate at elevated temperature to form compound (14) which is treated with alcoholic ammonia at elevated temperature to form compound (15). Hydrolysis of the carboxamide followed by decarboxylation forms compound (17) which is converted to its chloroimidate (6c) under standard conditions. Compound (6c) can be reacted with compound (3) at elevated temperature to produce compound (7c).

Scheme 4b

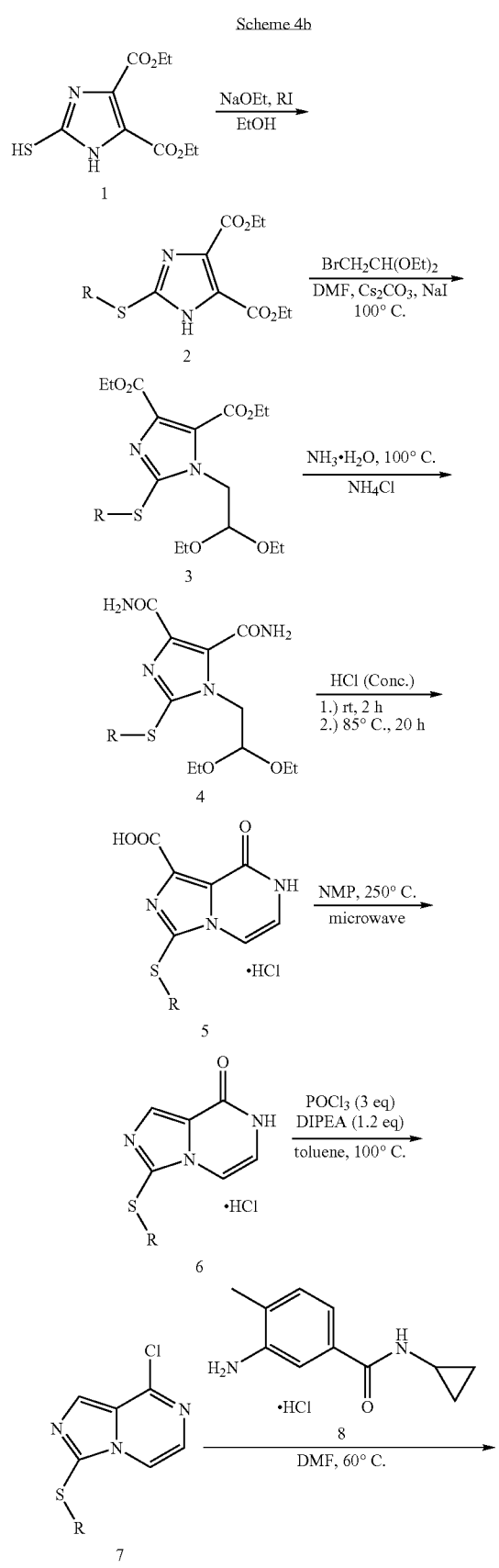

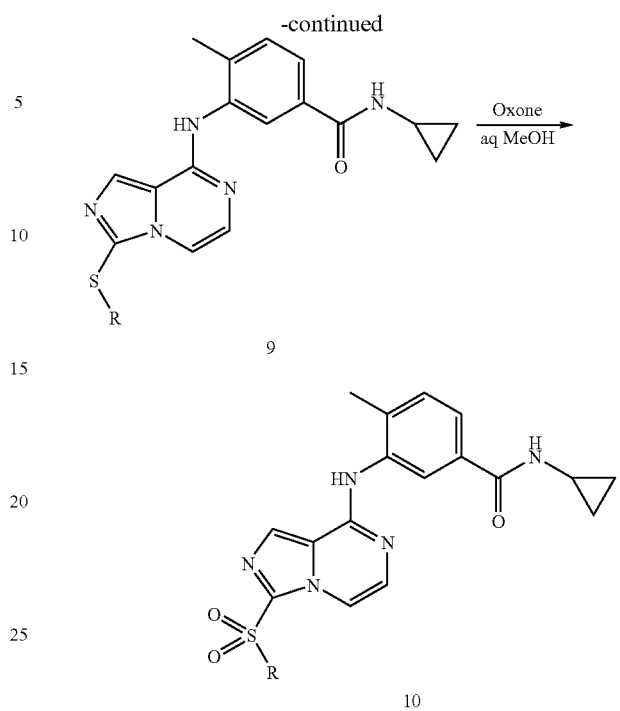

Compound (10) can be prepared from compound (1) as depicted in Scheme 4b. Compound (1) can be prepared according to Anderson, W. K.; Bhattacharjee, D.; Houston, D. M. *J. Med. Chem.* 1989, 32(1), p119. Compound (2) can be prepared from compound (1) be reacting with a halide in the presence of a base, such as sodium ethoxide, in a solvent, such as ethanol. Compound (2) can be reacted with a halide in the presence of a base, such as cesium carbonate, in a solvent, such as dimethylformamide, to afford compound (3). Compound (4) can be prepared from compound (3) by reacting with aqueous ammonia in the presence of ammonium chloride. Compound (5) can be prepared from compound (4) by hydrolysis in the presence of an acid, such as hydrochloric acid. Compound (5) can be heated in a solvent, such as NMP, to afford compound (6). Compound (7) can be prepared from compound (6) by reacting with phosphorus oxychloride in the presence of a base, such as diisopropylethylamine, in a solvent, such as toluene, to afford compound (7). Compound (7) can be reacted with compound (8) in the presence of a solvent, such as dimethylformamide, to afford compound (9). Finally, compound (9) can be reacted with an oxidant, such as Oxone, in the presence of a solvent, such as aqueous methanol, to afford compound (10).

Scheme 5

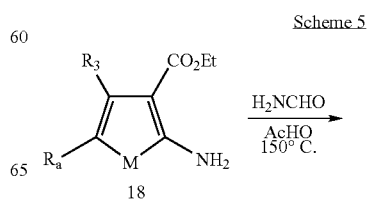

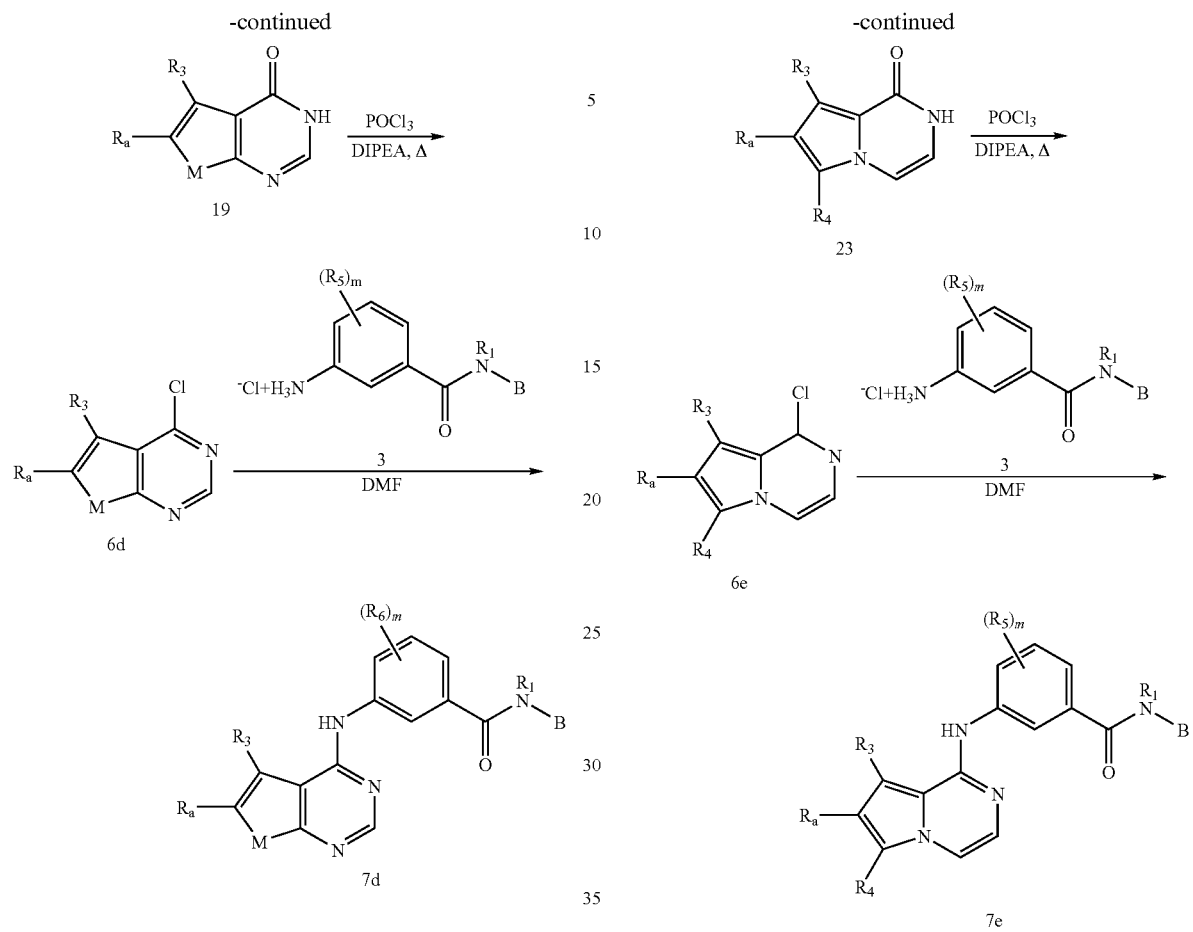

Compound (18) can be reacted with formamide at elevated temperature to form compound (19) which is converted to the chloro-imidate (6d) under standard conditions. Compound (6d) can be reacted with compound (3) at elevated temperature to produce compound (7d).

Pyrrole (20) can be treated with bromoacetaldehyde acetal (21) to form compound (22) which is treated with an acid in a non-protic solvent at elevated temperature to form compound (23) which is converted to its chloro-imidate (6e) under standard conditions. Compound (6e) can be reacted with compound (3) at elevated temperature to produce compound (7e).

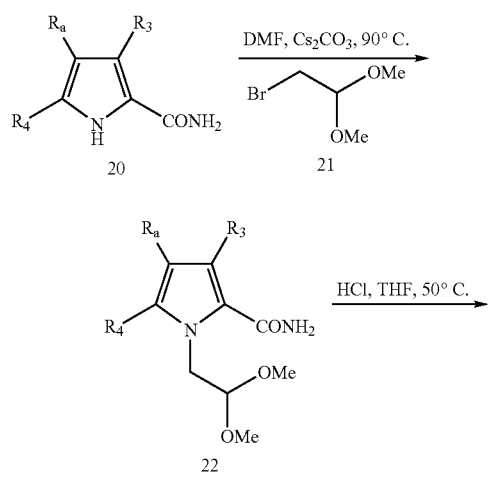

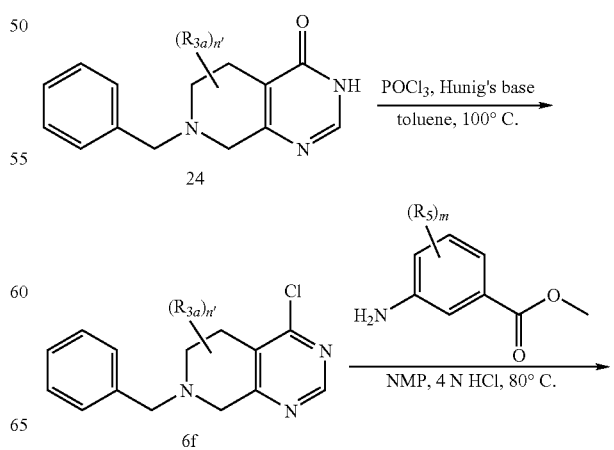

-continued

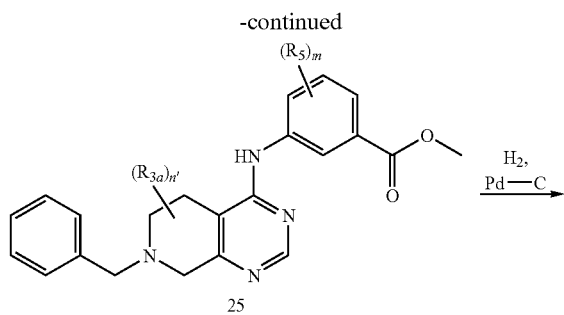
25

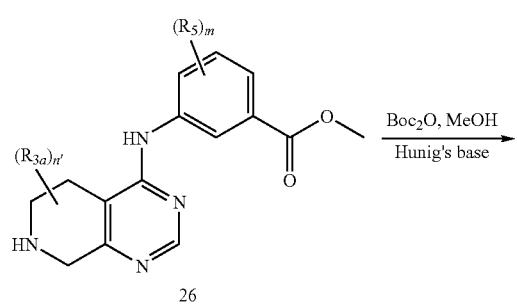
26

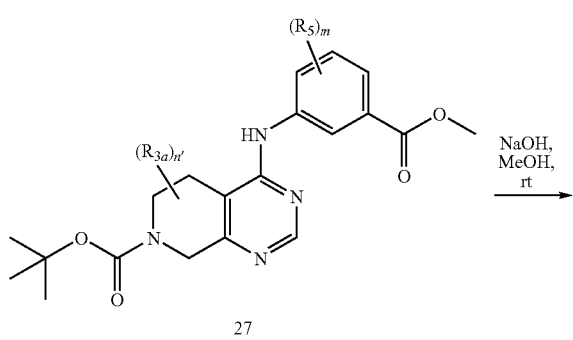
27

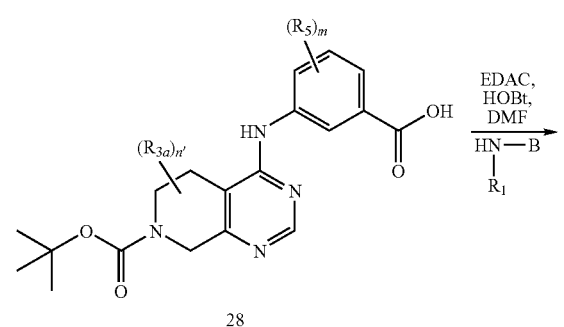
28

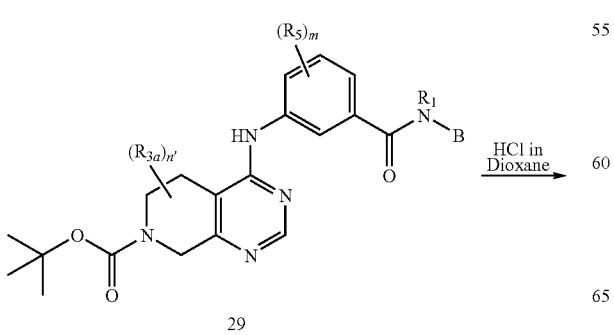
29

-continued

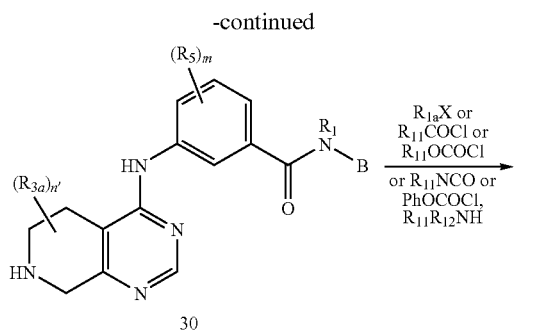
30

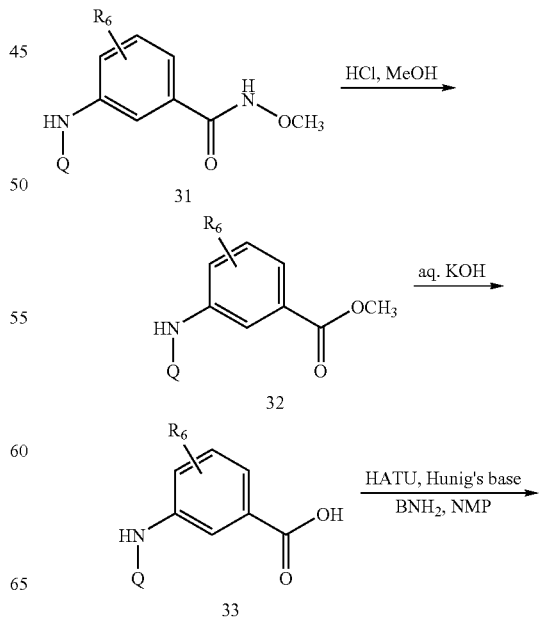

Compound 24 prepared according to the procedure described in the literature (*J. Het. Chem.* [1992] at p. 1369) can be converted to compound (6f) which can be reacted with an aniline under standard conditions to form compound (25). Debenzylation followed by protection of the aminogroup as its tert-butylcarbamate and hydrolysis of the ester under usual conditions forms compound (28) which can be condensed with an amine $R_1NHB$ to form compound (29). Compound (29) can be reacted with an acid to form compound (30) which can be treated with a halide ($R_{1a}X$), or acid chloride, or a carbamoyl chloride, or a isocyanate, or with phenyl chloroformate followed by an amine to form compound (7f).

-continued

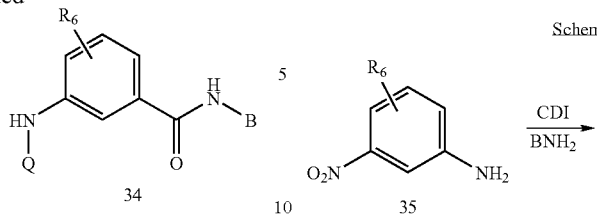
34

A substituted hydroxamate (31) can be reacted with acid, such as HCl, in anhydrous MeOH, to afford compound (32). Compound (32) can be reacted with an aq. base such KOH with heating to form compound (33). Compound (33) is reacted with an amine B—NH$_2$ in the presence of a coupling reagent, such as HATU, and a base such as diisopropylamine, in an organic solvent, such as N-methylpyrrolidinone to afford compounds (34). Hydroxamate (31) can be prepared as outlined in Scheme 1 and/or as shown in U.S. patent application Ser. No. 10/036,293.

Scheme 9

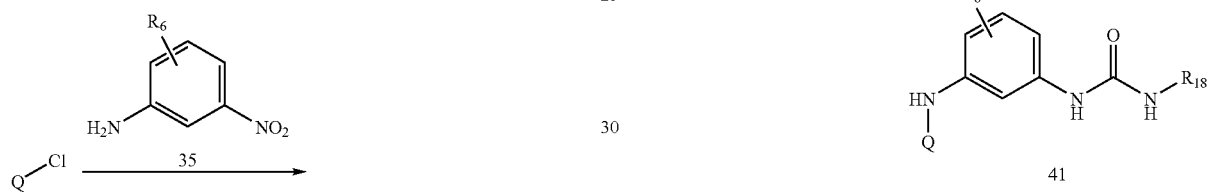

Chloroheterocycles (6a-f) (see Schemes 2-7) can be reacted with an aniline (35) in anhydrous DMF at rt to afford compound (36). Reaction of compound (36) can be reacted with hydrogen in the presence of a catalyst, such as Pd/C, in an organic solvent, such as MeOH to afford compound (37). Reaction of compound (37) with an isocyanate in an organic solvent, such as DCE affords compound (38). Methods of making compounds (6a-f) wherein R$_6$ is other than hydrogen are well known in the field.

Scheme 10

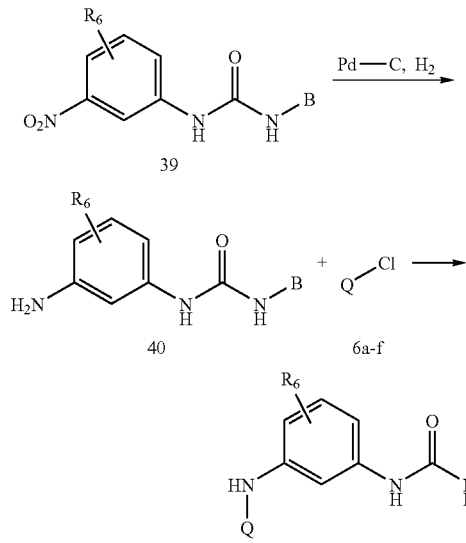

Commercially-available compound (35), can be reacted with carbonyl diimidazole and an amine B—NH$_2$ in an organic solvent, such as DCE, to yield compound (39). Reaction of compound (39) with hydrogen in the presence of a catalyst, such as Pd, in an alcoholic solvent such as EtOH affords compound (40). Reaction of (40) with chloride (6a-f) in an organic solvent, such as DMF, affords compound (41).

Scheme 11

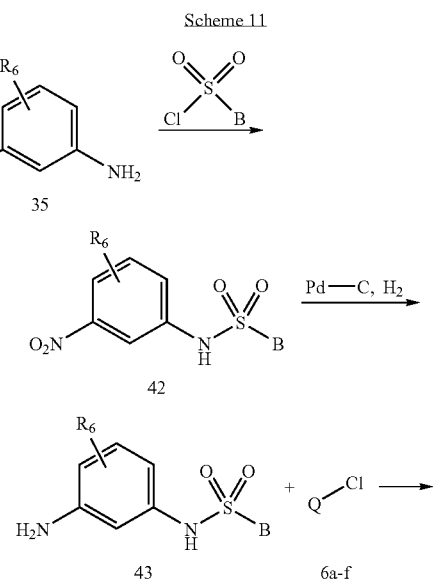

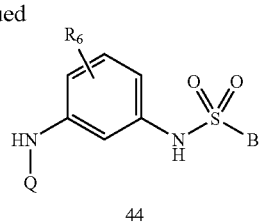

Commercially-available compound (35) can be reacted with a sulfonyl chloride in the presence of a base, such as TEA, in an organic solvent, such as DCM to yield compound (42). Reaction of compound (42) with hydrogen in the presence of a catalyst, such as Pd in a solvent, such as MeOH, yields compound (43). Reaction of compound (43) with chloride (6a-f) in an organic solvent, such as DMF, at rt affords compound (44).

In addition, other compounds of formula I may be prepared using procedures generally known to those skilled in the art and/or set forth in the various patent applications and publications cited herein, which are incorporated herein by reference. As an illustration, the following examples provide additional methods for the preparation of the compounds of this invention.

EXAMPLES

The invention will now be described with referenced to the Examples, which are exemplary and non-limiting in nature.

Example 1

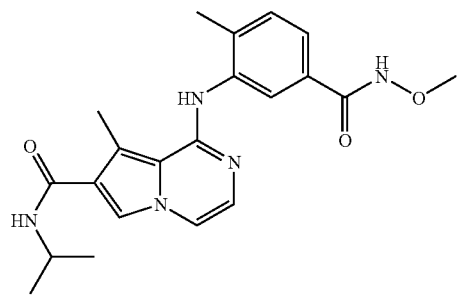

1A

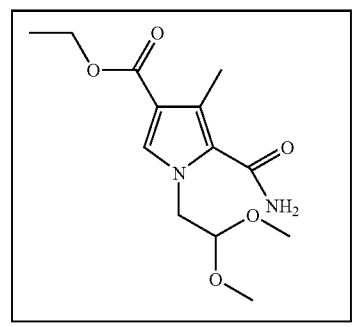

To a solution of 5-carbamoyl-4-methyl-1H-pyrrole-3-carboxylic acid ethyl ester (5.3 g, 27 mmol), and bromoacetaldehyde dimethyl acetal (1:1 equiv) (*Synthesis*, 1987, 566) in DMF (1.0 M) was added Cs$_2$CO$_3$ (10.8 g, 33 mmol) at rt. The reaction mixture was stirred and heated at 120° C. for 3 days. The reaction mixture was cooled, and water added (25 mL) to precipitate the product. The solids were collected by filtration and washed with water to furnish 1A as a yellow solid (3.3 g, 43%).

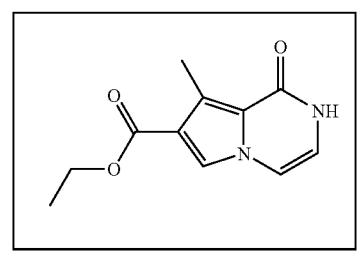

1B

To a suspension of 1A (3.2 g, 11.3 mmol) in THF (20 mL) was added concentrated HCl (1 mL). The mixture was heated at 50° C. for 4 h. The reaction mixture was cooled and the solvent was removed on a rotary evaporator. The yellow solid was dried in vacuo to afford 1B (2.6 g, 100%).

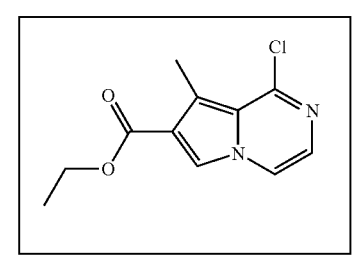

1C

To a solution of 1B (320 mg, 1.45 mmol) in toluene (6 mL) was added DIPEA (201 μL, 1.16 mmol, 0.8 equiv) and POCl$_3$ (162 μL, 1.74 mmol, 1.2 equiv) and the reaction mixture heated at 120-125° C. (oil bath temp) for 20 h. The reaction mixture was cooled and poured into ice cold sat. NaHCO$_3$-water-EtOAc (20 mL-20 mL-100 mL) and stirred rapidly to assure quenching of the excess POCl$_3$. The layers were separated (filtered through Celite if a suspension formed) and the organic layer was washed again with sat. NaHCO$_3$. The organic layer was dried over Na$_2$SO$_4$, filtered and concentrated in vacuo to afford 1C as a tan yellow solid (300 mg, 86%).

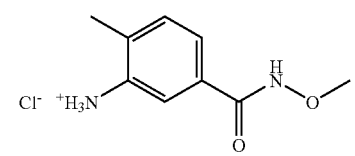

1D

A mixture of commercially-available 4-amino-3-methylbenzoic acid (100 g, 0.66 mol) and di-tertbutyl dicarbonate (150 g, 0.68 mol) in THF (1000 mL) was slowly heated to 50° C. overnight. The resulting mixture was cooled to rt and the solvent was removed on a rotary evaporator. The resulting solids were triturated with hexanes and dried in vacuo to afford 151 g (91%) of the crude BOC-protected aniline intermediate as a light pink solid. To the above, light-pink solid was added 1-(3-dimethylaminopropyl)-3-ethylcarbodiimide hydrochloride (127 g, 0.66 mol), HOBt (90 g, 0.66 mol), and DMF (1000 ml), and the resulting mixture was stirred at rt for 30 minutes followed by addition of methoxyamine hydrochloride (55 g, 0.66 mol) in one portion. After stirring for 10 min, the mixture was cooled using an ice bath. Diisopropylethylamine (250 ml, 1.4 mol) was added at such a rate so as to maintain the internal reaction temperature below 25° C. After the addition was complete, the ice bath was removed and the reaction was stirred overnight at rt. The reaction mixture was partitioned between 0.5 L of water and 1.5 L of EtOAc and the resulting layers were separated. The aqueous portion was extracted with additional EtOAc (400 mL×3), and the combined organic extracts were washed with water (300 mL×3), cold 0.5 N aqueous HCl (400 mL×2), and water (500 mL). The product was then extracted with cold 0.5 N aqueous NaOH (300 mL×3) and the combined basic aqueous extracts were neutralized to pH=8 by a slow addition of cold 0.5 N aqueous HCl. The resulting solid which precipitated was collected by filtration and washed with cold water. The wet solid was decolorized in hot EtOH with active charcoal to give 106 g of white solid as the BOC-protected N-methoxyamide intermediate.

To a slurry of the above solid (91 g, 0.32 mol) in 1,4-dioxane (400 mL) at rt was added a 4M solution of HCl in dioxane (400 mL), and the resulting mixture was stirred at rt overnight. Diethyl ether (1000 mL) was added and the precipitated solid was collected by filtration and triturated with a hot EtOH/H$_2$O mixture (4:1 v/v). Drying the resulting solid in vacuo afforded 53 g of the pure hydrochloride salt (ID) as a white solid. $^1$H NMR (d$^6$-DMSO): δ 9.5-9.9 (br. s, 1H), 7.75 (s, 1H), 7.55 (d, 1H), 7.36 (d, 1H), 3.70 (s, 3H), 2.38 (s, 3H).

1E

To a solution of the compound ID (384 mg, 1.77 mmol) in DMF (4 mL) was added DIPEA (279 mL, 1.77 mmol, 0.95 equiv) and compound IC (432 mg, 1.69 mmol). The reaction vessel was heated to 60° C. (oil bath temp) for 16 h. The mixture was then cooled and added water (25 mL). The solids were stirred for 1 h, then filtered and washed with water (2×10 mL). The wet yellow solid was directly used in the next step.

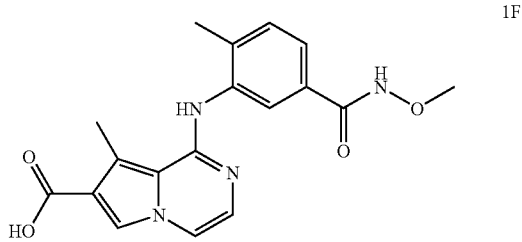

1F

Compound 1E was added to 1N NaOH (5 mL) and the reaction mixture heated at 55° C. for 2 h, then cooled and neutralized with 1N HCl to pH=5. The solids were filtered and washed with water (2×2 mL), and dried in vacuo to afford IF as a yellow solid (426 mg, 71%, two steps).

Step G, Example 1

To a solution of compound 1F (28 mg, 0.079 mmol) in 0.5 ml DMF was added HOBt (11 mg, 0.085 mmol) and EDCI (16 mg, 0.085 mmol). The reaction mixture was stirred at rt for 1 h. To the mixture was added DIPEA (15 μL, 0.085 mmol) and isopropylamine (8 μL, 0.1 mmol), and the mixture was stirred at rt for 3 h. The mixture was diluted to 2.5 mL with MeOH—H$_2$O (90-10), filtered and purified by preparative HPLC to afford a white solid (29 mg, 92%), HPLC rt 2.14 min: LRMS 396.4 (M+H).

Examples 2-12

The following compounds in Table 1 have been synthesized following the procedures described in Example 1, utilizing the appropriate starting materials.

TABLE 1

| Ex# | Structure | HPLC RT | MS (M + H) |
|---|---|---|---|
| 2 | 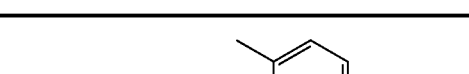 | 2.00 | 382.30 |

TABLE 1-continued

| Ex# | Structure | HPLC RT | MS (M + H) |
|---|---|---|---|
| 3 | 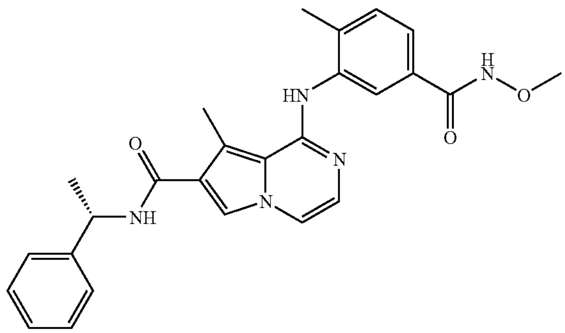 | 2.74 | 458.30 |
| 4 | 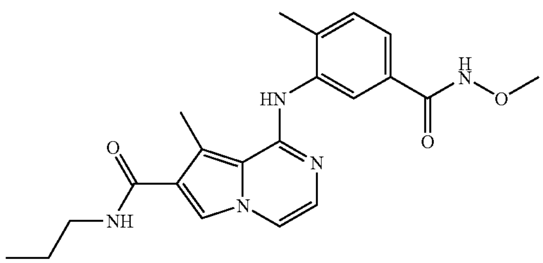 | 2.24 | 396.30 |
| 5 | 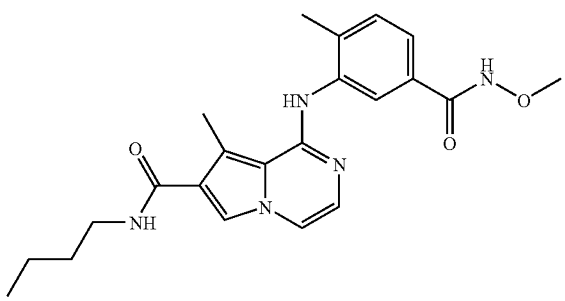 | 2.48 | 410.30 |
| 6 | 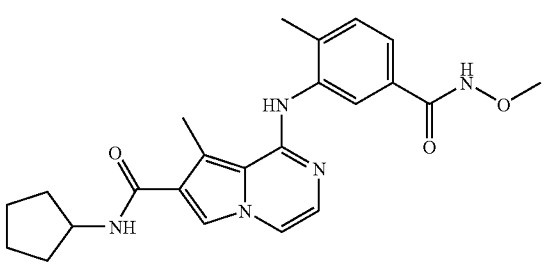 | 2.48 | 422.20 |
| 7 | 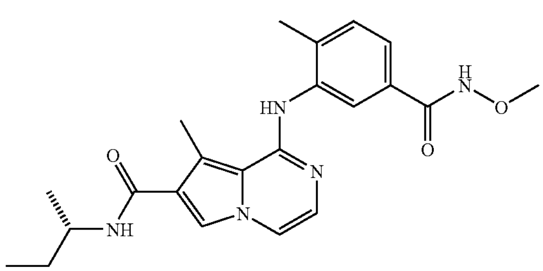 | 2.33 | 410.40 |

TABLE 1-continued

| Ex# | Structure | HPLC RT | MS (M + H) |
|---|---|---|---|
| 8 | 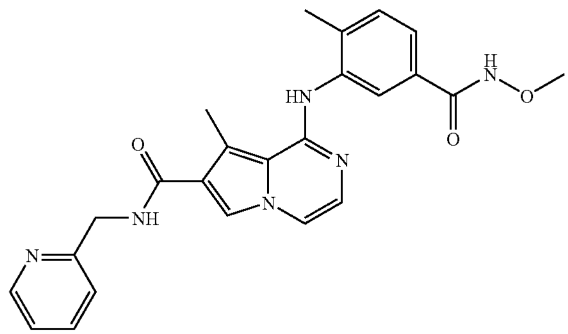 | 1.54 | 445.40 |
| 9 | 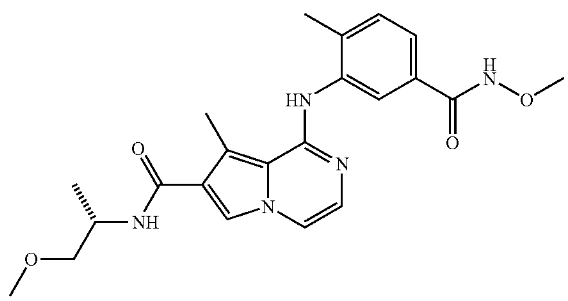 | 2.09 | 426.30 |
| 10 | 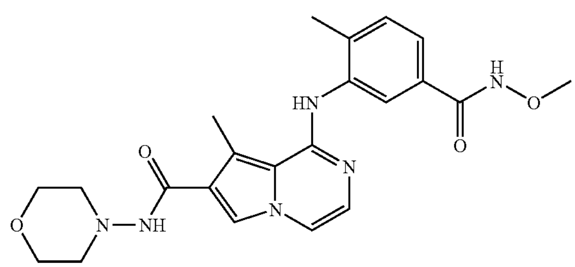 | 1.82 | 439.20 |
| 11 | 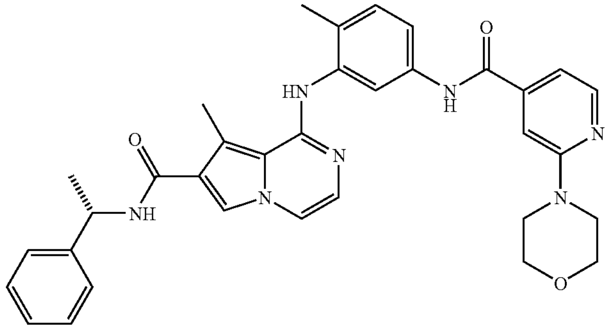 | 2.81 | 590.30 |

TABLE 1-continued

| Ex# | Structure | HPLC RT | MS (M + H) |
|---|---|---|---|
| 12 | 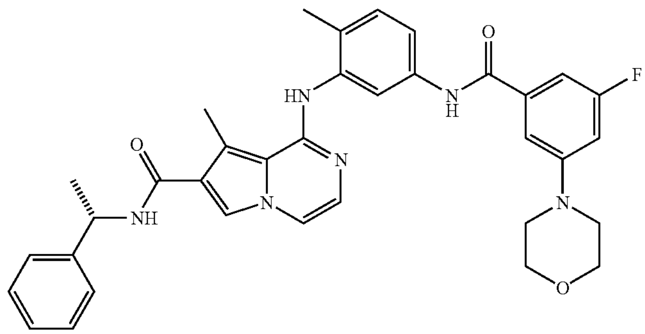 | 3.41 | 607.20 |

Example 13

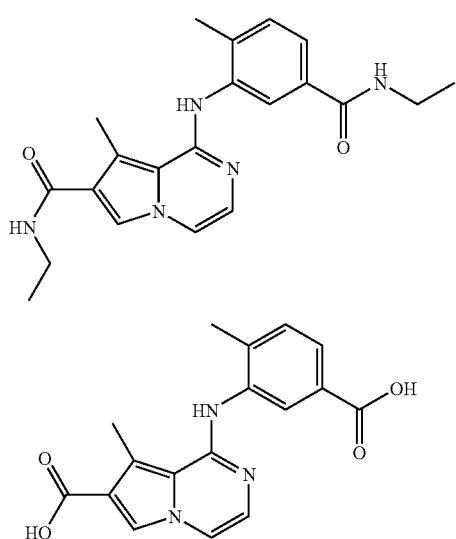

To a solution of 3-amino-4-methyl-benzoic acid methyl ester (107 mg, 0.65 mmol) in DMF (2 mL) was added solid compound 1C (148 mg, 0.62 mmol). The reaction vessel was heated to 60° C. (oil bath temp) for 16 h. The mixture was then cooled and 25 mL water was added. The solids were stirred for 1 h, then filtered and washed with water (2×10 mL). The wet yellow solid was dissolved in 2 N NaOH (2 mL), THF (2 mL) and MeOH (2 mL). The reaction mixture was heated at 60° C. for 4 h. The mixture was cooled and neutralized with 2N HCl to pH=4. The solids were filtered, washed with water (2×5 mL) and dried in vacuo to afford the diacid as a yellow solid (167 mg, 82% two steps).

Step B, Example 13

To a solution of compound 13A (17 mg, 0.0525) in 0.5 mL DMF was added HOBt (16 mg, 0.116 mmol), EDCI (22 mg, 0.116 mmol) and DIPEA (20 µL, 0.116 mmol). The mixture was stirred at rt for 1 h. To the reaction mixture was added ethylamine hydrochloride (9 mg, 0.11 mmol). The reaction mixture was stirred at rt for 3 h. An off white solid was obtained after purification by Preparative HPLC (6 mg, 30%), HPLC rt 2.08 min, LRMS 380.4 (M+H).

Example 14

The following compound in Table 2 was synthesized following the procedures described in Example 13, utilizing the appropriate starting materials.

TABLE 2

| Ex # | Structure | HPLC RT | MS (M + H) |
|---|---|---|---|
| 14 | 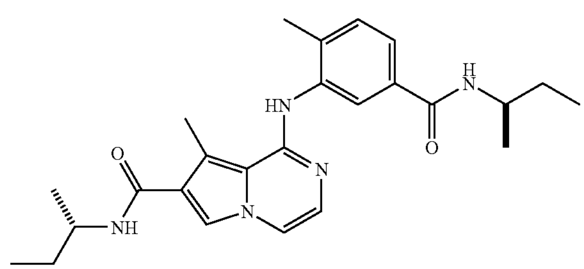 | 2.82 | 436.6 |

Example 15

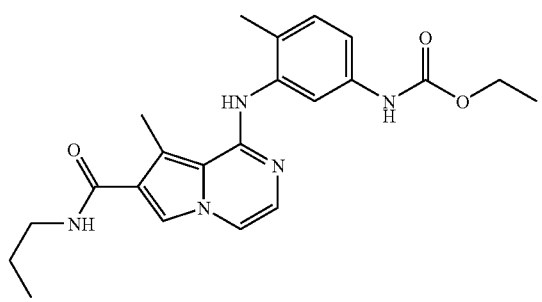

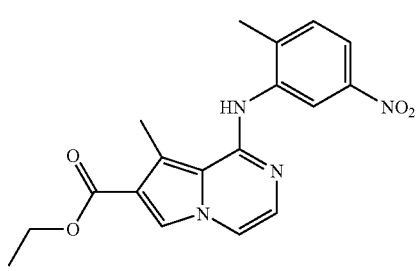

15A

To a solution of 2-methyl-5-nitro-phenylamine (430 mg, 2.84 mmol) in DMF (5 mL) was added solid compound 1C (680 mg, 2.84 mmol) and a drop of conc. HCl. The reaction mixture was heated to 60° C. for 16 h. The mixture was then cooled and water was added (25 mL). The solids were stirred for 3 h, filtered, washed with water (2×10 mL), and dried in vacuo to afford 15A as a beige solid (651 mg, 64%).

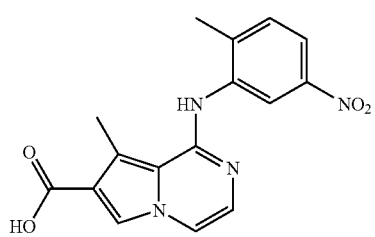

15B

A solution of 15A (560 g, 1.58 mmol) in 10 ml 1N NaOH, 10 ml THF and 5 ml MeOH was heated at 65° C. for 4 h. The mixture was cooled and neutralized with 1N HCl to pH=6, and the solvent evaporated. To the solids were added 10 ml water and the mixture was stirred for 2 h. The solid was filtered and dried in vacuo to afford a yellow solid (362 mg, 70%).

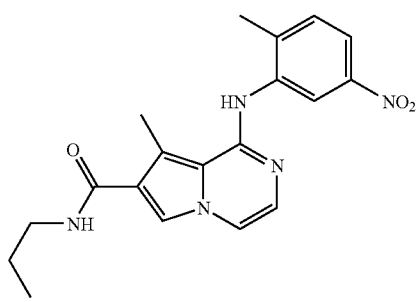

15C

To a solution of 15B (140 mg, 0.43 mmol) in 3 mL DMF was added benzotriazole-1-yl-oxy-tris-(dimethylamino)-phosphonium hexafluorophosphate (199 mg, 0.47 mmol) and DIPEA (165 μL, 0.95 mmol). The mixture was stirred at rt for 0.5 h. The reaction mixture was added n-propylamine (40 μL, 0.45 mmol) and stirred at rt for 4 h. The mixture was then added water (30 mL) and stirred for 2 h. The solid was filtered and washed with water.

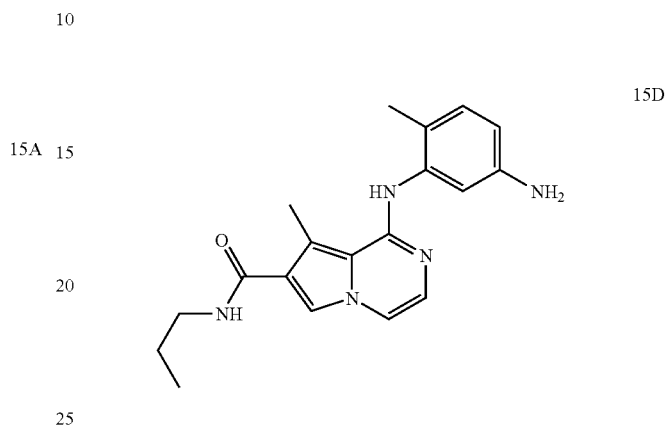

15D

To a suspension of 15C in EtOH (5 mL) and EtOAc (10 mL) was added 5% Pd/C (5 mol %). The reaction mixture was evacuated and backfilled with H$_2$ three times and stirred for 2 h. The mixture was filtered and concentrated to give a yellow solid as 15D (140 mg, 96% two steps).

Step E, Example 15

To a suspension of 15D (25 mg, 0.074 mmol) in 2 mL CH$_2$Cl$_2$ at 0° C. was added ethyl chloroformate (7.8 μl, 0.082 mmol) and triethylamine (11 μL, 0.082 mmol). The reaction mixture was stirred 0° C. for 1 h and warmed to rt for 6 h. The solvent was evaporated and the residue purified by preparative HPLC to give a yellow solid (13 mg, 43%) HPLC rt 2.64 min, LRMS 410.3 (M+H).

Example 16

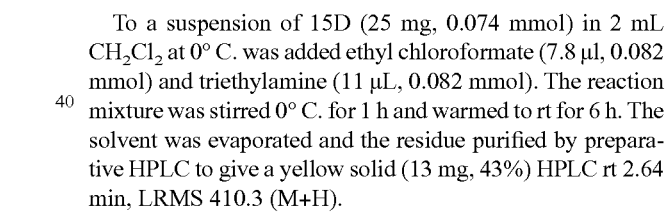

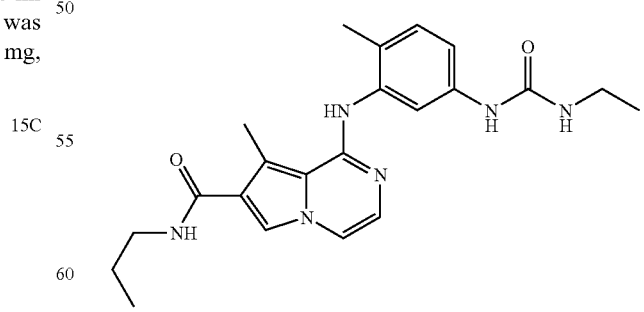

To a suspension of 15D (25 mg, 0.074 mmol) in CH$_2$Cl$_2$ (2 mL) at 0° C. was added ethyl isocyanate (6.5 μl, 0.082 mmol).

The reaction mixture was stirred for 1 h and warmed to rt for 6 h. The solvent was evaporated and the residue was purified by preparative HPLC to give a yellow solid (25 mg, 83%), HPLC rt 2.44 min, LRMS 409.3 (M+H).

Example 17

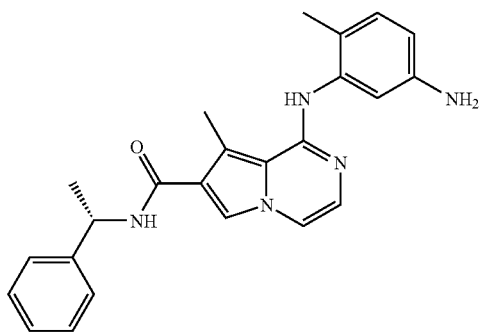

Example 17 was prepared utilizing the same procedure as 15D using the appropriate starting materials.

Example 18

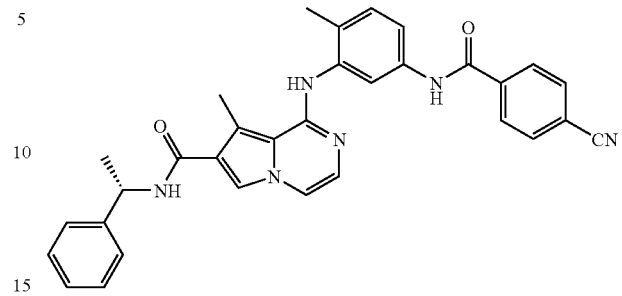

To a suspension of Example 17 (15 mg, 0.0375 mmol) in $CH_2Cl_2$ (2 mL) at 0° C. was added 4-cyanobenzoyl chloride (6.6 mg, 0.04 mmol) and DIPEA (7 μL, 0.04 mmol). The reaction mixture was stirred at 0° C. for 1 h and warmed to rt for 6 h. The solvent was evaporated and the residue was purified by preparative HPLC to give a yellow solid (8 mg, 40%), HPLC rt 3.17 min, LRMS 529.3 (M+H).

Examples 19-24

The following compounds in Table 3 were synthesized following the procedures described for Examples 15-18 utilizing the appropriate starting materials.

TABLE 3

| Ex # | Structure | HPLC RT | MS (M + H) |
|---|---|---|---|
| 19 | 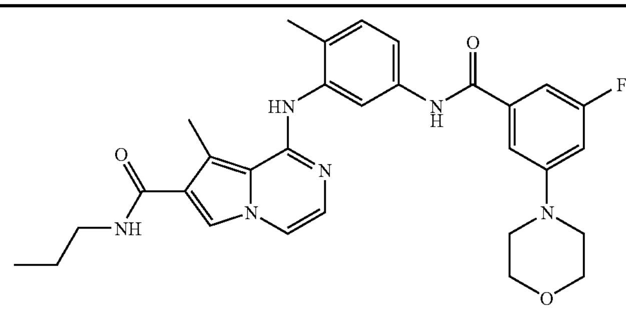 | 3.16 | 545.40 |
| 20 | 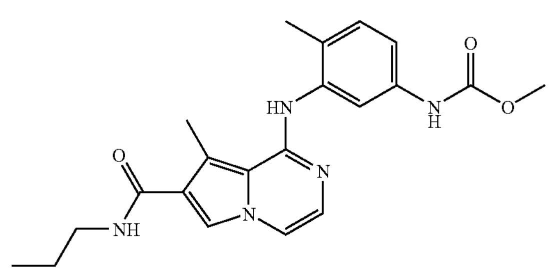 | 2.53 | 396.20 |
| 21 | 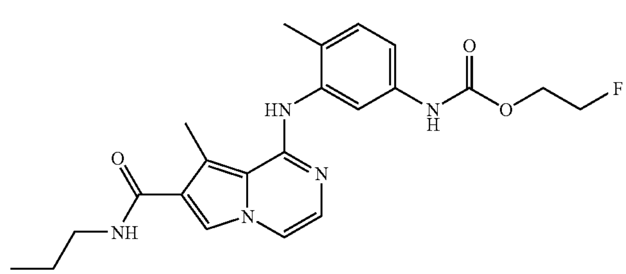 | 2.59 | 428.30 |

TABLE 3-continued

| Ex # | Structure | HPLC RT | MS (M + H) |
|---|---|---|---|
| 22 | 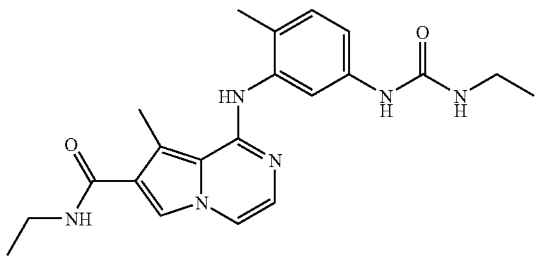 | 3.50 | 395.20 |
| 23 | 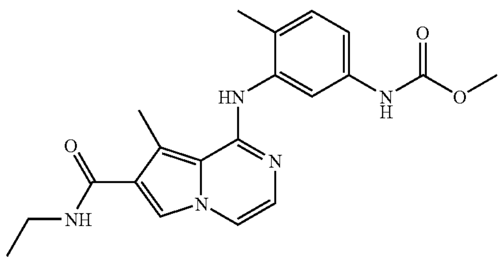 | 2.24 | 382.30 |
| 24 | 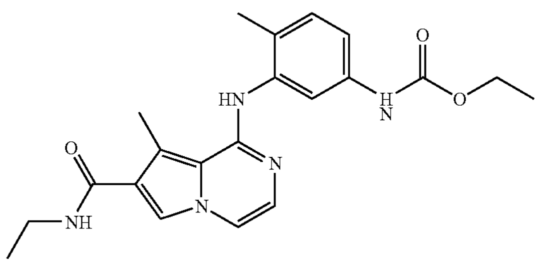 | 2.46 | 396.30 |

Example 25

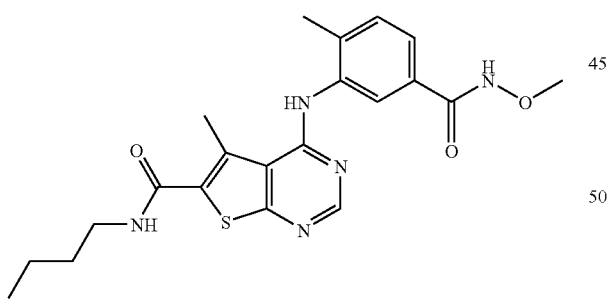

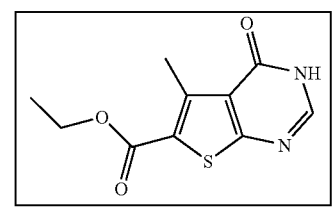
25A

To a solution of diethyl 5-amino-3-methyl-2,4-thiophene-dicarboxylate in formamide (16 mL) was added acetic acid (0.5 mL). The mixture was heated at 150° C. for 40 h, cooled to 70° C. and water was added (90 mL). The suspension was cooled to rt with stirring. The solids were filtered, washed with water (3×10 ml) and dried in air to give a yellow solid (1.61 g, 92%).

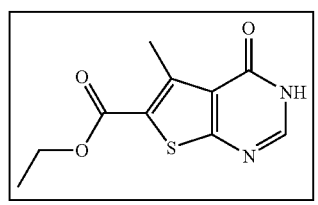
25B

To a solution of 25A (425 mg, 1.783 mmol) in toluene (8 mL) was added DIPEA (248 µL, 1.426 mmol, 0.8 equiv) and POCl₃ (199 µL, 2.14 mmol, 1.2 equiv). The reaction mixture was heated at 120-125° C. (oil bath temp) for 3 h. The reaction mixture was cooled and poured into ice cold sat. NaHCO₃-water-EtOAc (20 mL-20 mL-50 mL) and stirred rapidly to assure quenching of the excess POCl₃. The layers were separated and the organic layer was washed again with sat. NaHCO₃. The organic layer was dried over Na₂SO₄, filtered and concentrated in vacuo to afford 25B as a yellow solid (432 mg, 94%).

25C

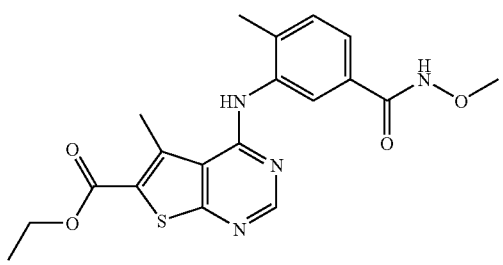

To a solution of 3-amino-N-methoxy-4-methyl-benzamide hydrochloride (384 mg, 1.77 mmol) in DMF (4 mL) was added DIPEA (279 µL, 1.61 mmol, 0.95 equiv) and compound 25B (432 mg, 1.69 mmol). The reaction was heated for 16 hours at 60° C. The mixture was cooled to rt, water was added (25 mL) and the mixture was stirred for 1 h. The solids were filtered, washed with water (3×10 mL) and dried on the filter.

25D

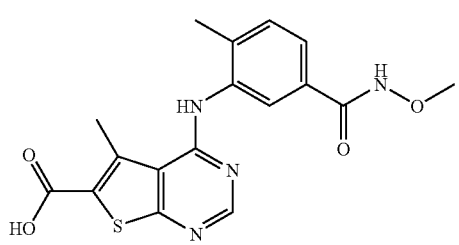

To a solution of NaOH (1N, 5 mL) was added 25C and the reaction mixture was heated at 60° C. for 2 hours then cooled to rt. The mixture was neutralized to pH=6 with conc. HCl and stirred for 1 h. The solids were filtered, washed with cold water (3×5 mL) and dried in vacuo to afford as a yellow solid 25D (426 mg, 68% two steps).

Step E, Example 25

To a solution of 25D (28 mg, 0.079 mmol) in DMF (0.5 mL) was added HOBt (11 mg, 0.085 mmol), and EDCI (16 mg, 0.085 mmol). The reaction mixture was stirred at rt for 1 h, then to this was added DIPEA (15 µL, 0.085 mmol) and n-butylamine (10 µL, 0.1 mmol). The reaction mixture was further stirred at rt for 3 h. The mixture was diluted to 2.5 mL with MeOH—H₂O (90-10), filtered and subjected to Preparative HPLC to afford a white solid (28 mg, 83%), HPLC RT 3.29 min, LRMS 428.5 (M+H).

Examples 26-40

The following compounds in Table 4 have been synthesized utilizing the procedures described in Example 25, and the appropriate starting materials.

TABLE 4

| Ex # | Structure | HPLC RT | MS (M + H) |
|---|---|---|---|
| 26 | 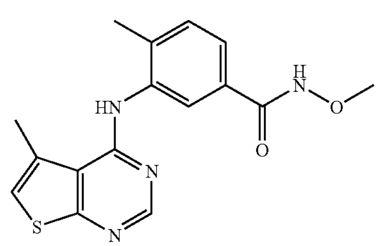 | 2.66 | 329.2 |
| 27 | 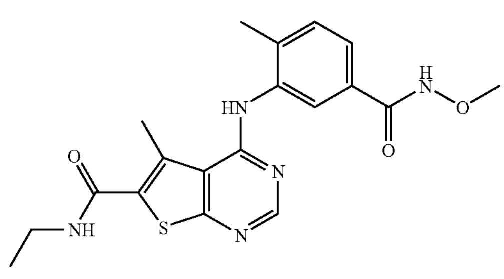 | 2.82 | 400.2 |

TABLE 4-continued

| Ex # | Structure | HPLC RT | MS (M + H) |
|---|---|---|---|
| 28 | 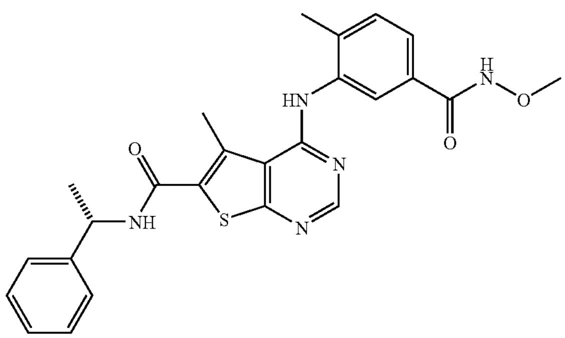 | 3.5 | 476.2 |
| 29 | 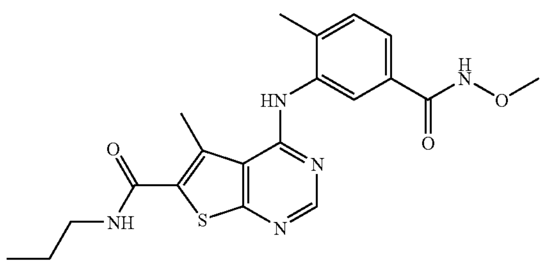 | 3.04 | 414.3 |
| 30 | 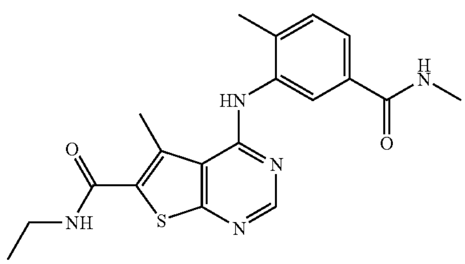 | 2.76 | 384.2 |
| 31 | 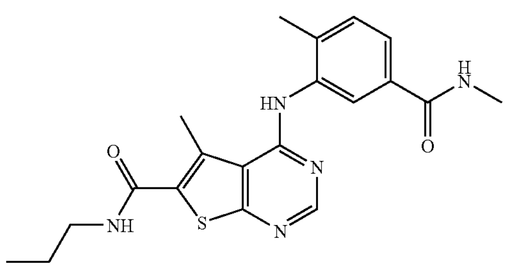 | 3.02 | 398.2 |
| 32 | 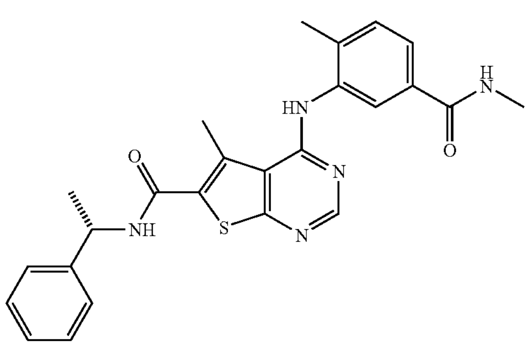 | 3.46 | 460.3 |

TABLE 4-continued

| Ex # | Structure | HPLC RT | MS (M + H) |
|---|---|---|---|
| 33 | 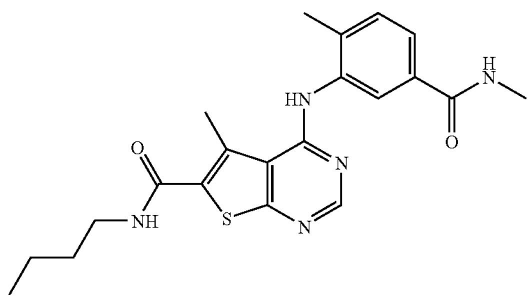 | 3.27 | 412.2 |
| 34 | 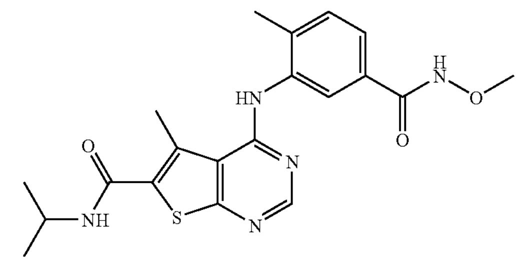 | 2.96 | 414.5 |
| 35 | 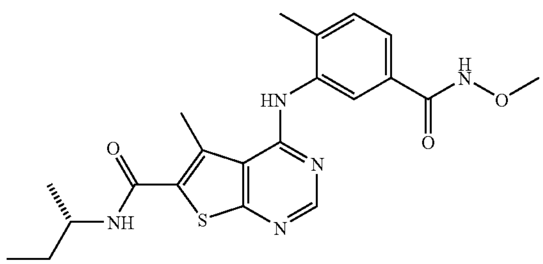 | 3.15 | 428.3 |
| 36 | 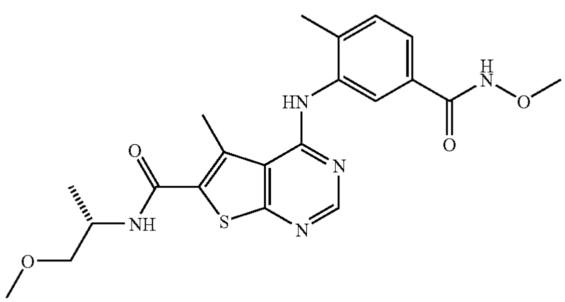 | 2.88 | 444.6 |
| 37 | 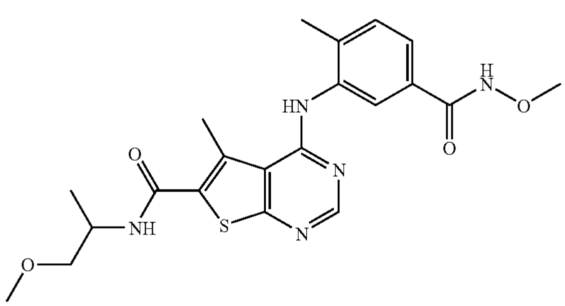 | 2.89 | 444.6 |

TABLE 4-continued

| Ex # | Structure | HPLC RT | MS (M + H) |
|---|---|---|---|
| 38 | 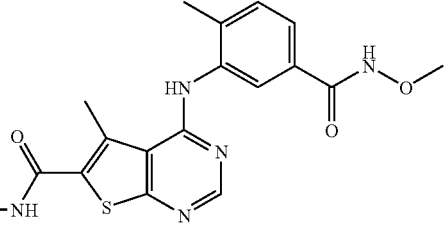 | 3.26 | 440.3 |
| 39 | 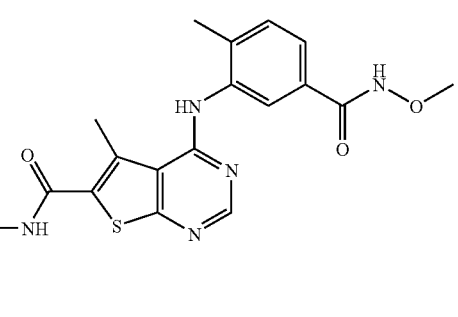 | 2.29 | 463.2 |
| 40 | 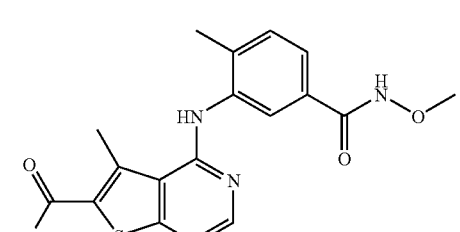 | 2.62 | 457.2 |

Example 41

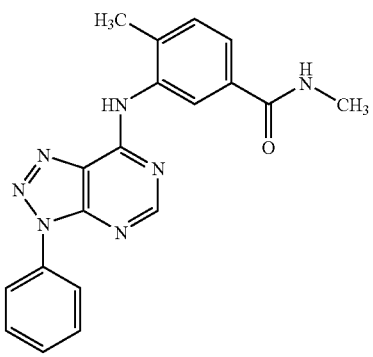

A solution of 4-chloro-1-phenyl-1,2,3,5,7-azaindene (70 mg, 0.3 mmol, J. Chem. Soc. (C), 1856, 1967), and 3-amino-4-methyl-N-methylbenzamide (65 mg, 0.4 mmol) in dry methanol (5 mL) was heated to 120° C. in an open R. B. flask for 30 min. The residue was cooled to rt, diluted with methanol (10 mL), and filtered. The solid was washed with EtOAC (10 mL, 2×), collected, and dried in vacuo to obtain the title compound 41 (80 mg, 74%) as a white solid. HPLC Retention time=2.65 min;

LC/MS (M+H)$^+$=360.27.

Example 42

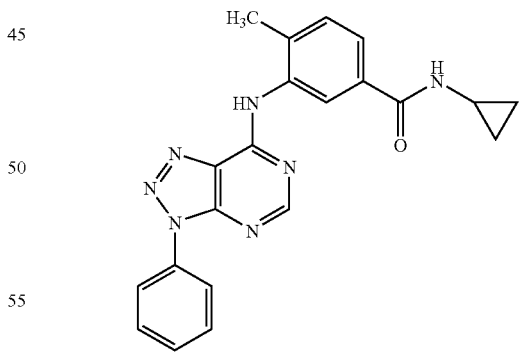

A solution of 4-chloro-1-phenyl-1,2,3,5,7-azaindene (70 mg, 0.3 mmol), and 3-amino-4-methyl-N-cyclopropylbenzamide (76 mg, 0.4 mmol) in dry methanol (5 mL) was heated to 120° C. in an open R. B. flask for 30 min. The residue was cooled to rt, diluted with methanol (5 mL), and filtered. The solid was washed with EtOAC (5 mL, 4×), collected, andried in vacuo to obtain the title compound 42 (70 mg, 55%) as a white solid. HPLC Retention time=2.85 min; LC/MS (M+H)$^+$=386.33. d

Example 43

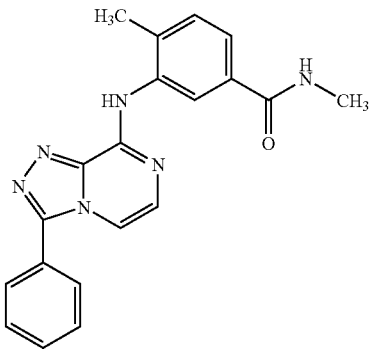

A solution of 4-chloro-1-phenyl-2,3,5,8-azaindene (46 mg, 0.2 mmol, French Patent FR2662163, 1991), and 3-amino-4-methyl-N-methylbenzamide (41 mg, 0.25 mmol) in dry methanol (10 mL) was heated to 130° C. in an open R. B. flask. Additional methanol (10 mL, 4×) was added at intervals and heating was continued for 1 h. The residue was cooled to rt, diluted with methanol (5 mL), and stirred for 1 h. The solid was filtered, washed with methanol (3 mL), EtOAC (5 mL, 2×), collected, and dried in vacuo to obtain the title compound 43 (38 mg, 53%). HPLC Retention time=1.25 min; LC/MS (M+H)$^+$=359.22.

Examples 44-52

The following compounds in Table 5 were synthesized utilizing the procedures described in Example 43 and the appropriate starting materials.

TABLE 5

| Ex. # | Structure | HPLC RT (min) | (M + H)$^+$ |
|---|---|---|---|
| 44 | 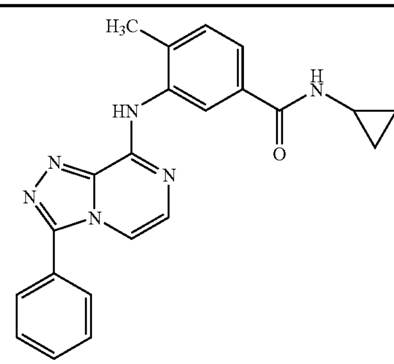 | 1.36$^a$ | 385.19 |
| 45 | 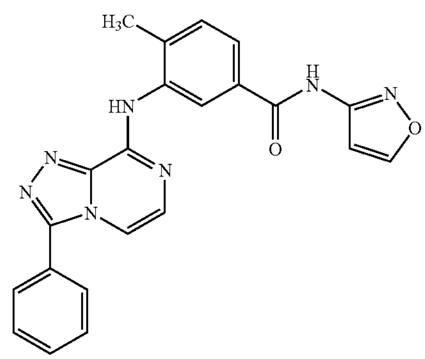 | 1.44$^a$ | 412.13 |
| 46 | 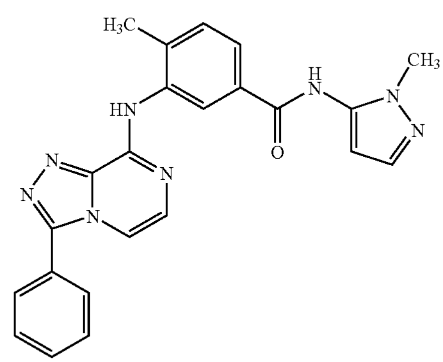 | 1.38$^a$ | 425.18 |

TABLE 5-continued

| Ex. # | Structure | HPLC RT (min) | (M + H)+ |
|---|---|---|---|
| 47 | 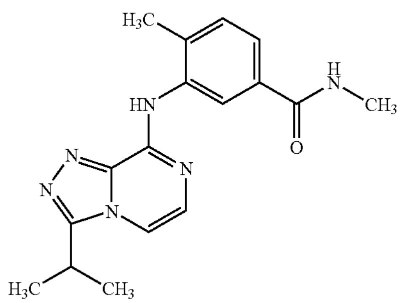 | 0.99[a] | 325.23 |
| 48 | 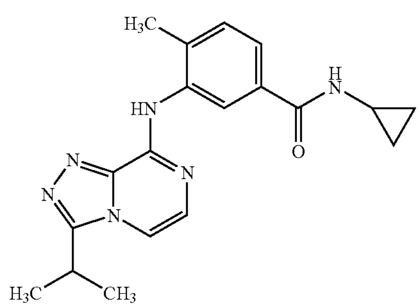 | 1.12[a] | 351.27 |
| 49 | 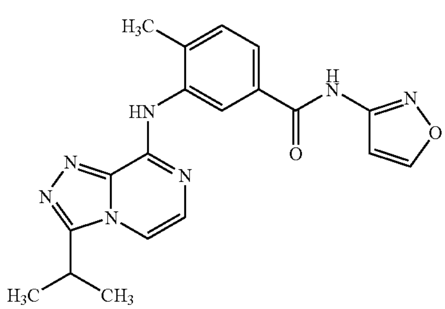 | 1.23[a] | 378.14 |
| 50 | 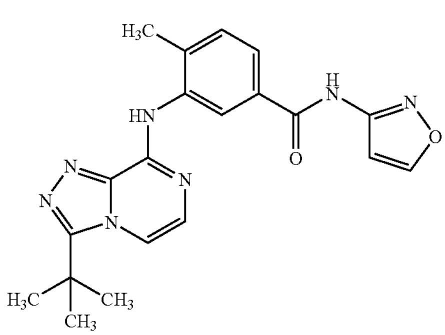 | 1.35[a] | 392.20 |

TABLE 5-continued

| Ex. # | Structure | HPLC RT (min) | (M + H)+ |
|---|---|---|---|
| 51 | 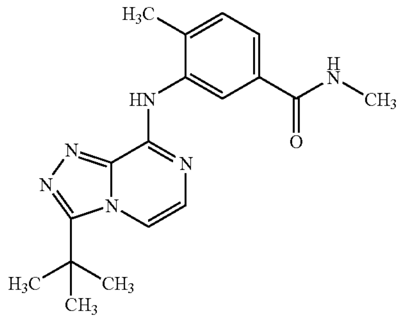 | 1.14[a] | 339.25 |
| 52 | 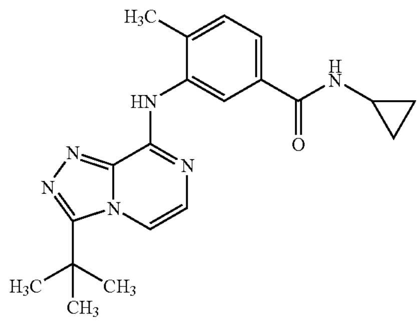 | 1.26[a] | 365.23 |

Example 53

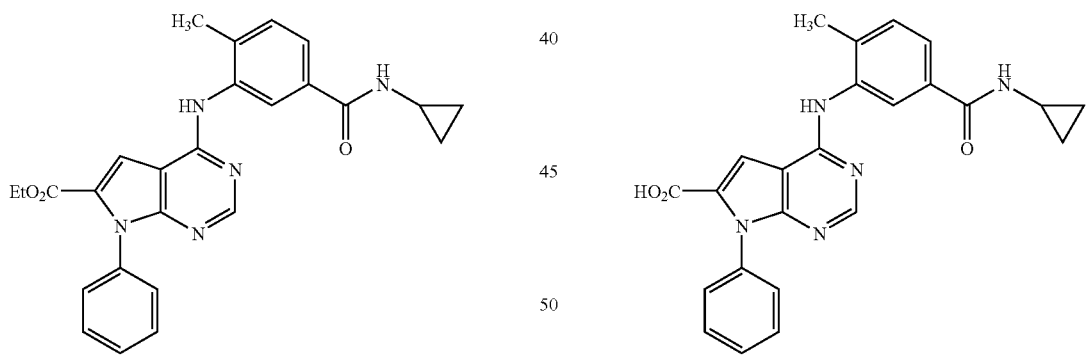

A suspension of ethyl-4-chloro-5-methyl-7-phenyl-7H-pyrrolo[2,3-d]pyrimidine (100 mg, 0.32 mmol), and 3-amino-4-methyl-N-cyclopropylbenzamide (120 mg, 0.65 mmol) in absolute EtOH (0.8 mL) was heated to 140° C. for 2 h, and in DMF (1 mL) for 3 h. DMF was removed and to the residue was added 1N aq. HCl solution (2 mL, 2×). The HCl extracts were combined and neutralized with solid NaHCO₃. The precipitate was collected by filtration, washed with water, hexanes, and dried in vacuo to obtain a solid which was triturated with ether-EtOAc mixture (95:5) to obtain the title compound 53 (59 mg, 36%) as a tan solid. HPLC Retention time=1.55 min; LC/MS (M+H)+=470.42.

Example 54

A solution of compound 53 (118.5 mg, 0.25 mmol) in THF-methanol mixture (2.8 mL, 1:1) and 1 N aq. NaOH solution (1.26 mL) was heated to 57° C. for 6 h and then left at rt for 48 h. The mixture was concentrated, diluted with 1 N aq. HCl solution and evaporated to dryness with toluene. The crude solid was chromatographed on a silica gel column and eluted with 2% methanol in dichloromethane, followed by 5% methanol in dichloromethane, and dichloromethane-methanol-acetic acid mixture (95:3:2) to obtain the title compound 54 (78 mg) as an off-white solid. HPLC Retention time=1.24 min; LC/MS (M+H)+=442.39.

Example 55

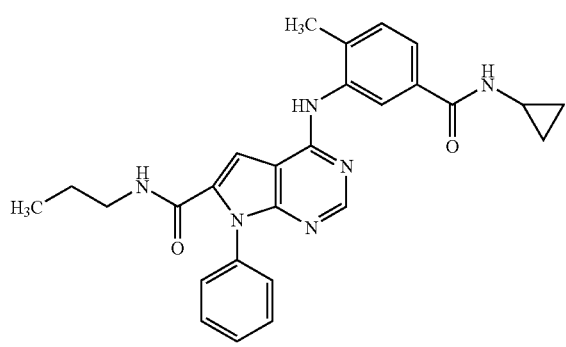

A solution of compound 54 (30 mg, 0.07 mmol), n-propyl amine (22.2 μL, 0.27 mmol), HOBT (12.6 mg, 0.08 mmol), EDC (26.1 mg, 0.14 mmol), and diisopropylethyl amine (47 μL, 0.27 mmol) in THF (1.7 mL) and DMF (0.3 mL) was heated at 60° C. for 2 h. Additional n-propyl amine (11 μL, 0.14 mmol) was added and heating was continued for 3 h. The mixture was concentrated, diluted with aq. NaHCO$_3$ solution (4 mL) and sonicated to obtain a precipitate which was collected by filtration, washed with 0.5 N aq. NaOH solution, water, and dried in vacuo over P$_2$O$_5$ to obtain the title compound 55 (26 mg, 80%) as a tan solid. HPLC Retention time=1.26 min; LC/MS (M+H)$^+$=483.53.

Example 56

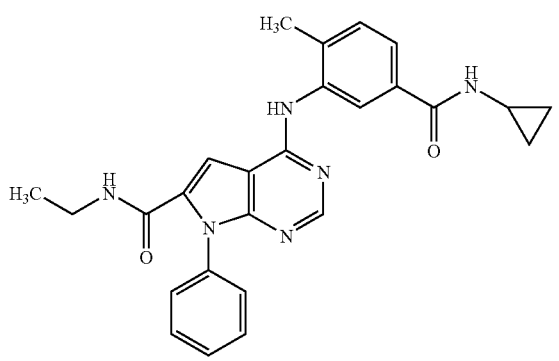

The title compound 56 was prepared following the same procedure as described for Example 55 except using ethyl amine in place of n-propyl amine. HPLC Retention time=1.14 min; LC/MS (M+H)$^+$=469.51.

Example 57

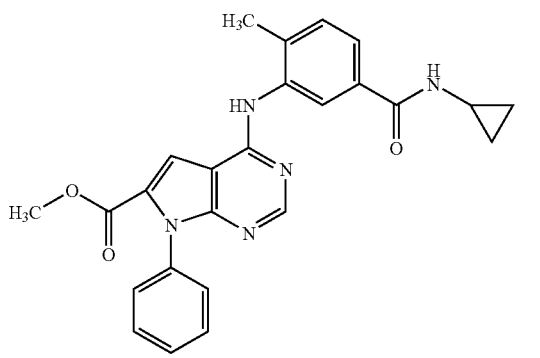

A solution of compound 54 (30 mg, 0.05 mmol), HOAt (7.4 mg, 0.05 mmol), EDC (17.3 mg, 0.09 mmol), and DIPEA (31 μL, 0.18 mmol) in MeOH (2 mL) was heated 60° C. for 16 h. The residue was chromatographed on a preparative reversed phase HPLC column: YMC S5 ODS 20×100 mm, 10 min gradient with 5 min hold, flow rate 20 mL/min, detection wave length 220 nm, starting solvent: 90% solvent A (10% MeOH-90% H$_2$O-0.1% CF$_3$COOH) and 10% solvent B (90% MeOH-10% H$_2$O-0.1% CF$_3$COOH); final solvent: 90% solvent B and 10% solvent A. Fraction containing the product was concentrated in SpeedVac. to obtain the title compound 57 (8.5 mg) as a tan solid. HPLC Retention time=1.44 min.; LC/MS (M+H)$^+$=456.19.

Example 58

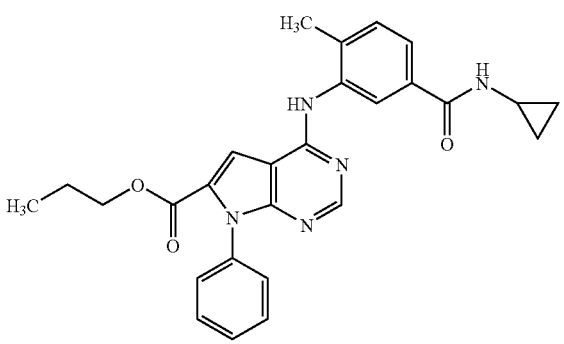

The title compound 58 was prepared following the same procedure as described for Example 57 except using 1-propanol in place of MeOH. HPLC Retention time=1.67 min; LC/MS (M+H)$^+$=484.22.

Example 59

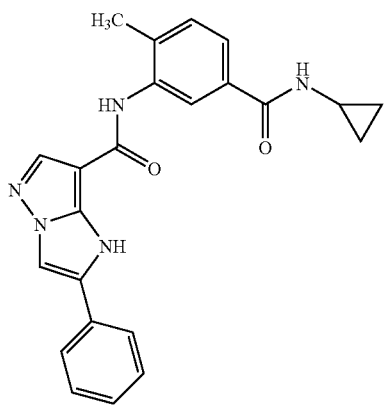

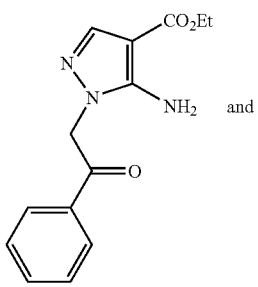

59A and

-continued

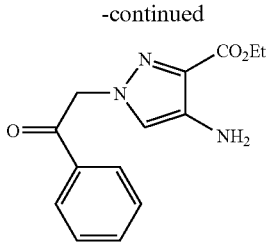

59B

To a rt slurry of ethyl 5-amino-4-pyrazolecarboxylate (1.0 g, 6.4 mmol) and potassium carbonate (1.3 g, 9.7 mmol) in DMF (6 mL) was slowly added bromoacetophenone (1.3 g, 6.4 mmol), and the resulting mixture was heated to 55° C. for 16 h. After cooling to rt, the mixture was diluted with water (30 mL) and extracted with EtOAc (3×40 mL). The combined extracts were diluted with hexanes (30 mL) and washed with water (3×30 mL) and brine (30 mL), then dried over anhydrous sodium sulfate, filtered, and concentrated in vacuo to afford 1.8 g of a 1:1 mixture of compounds 59A and 59B as an orange oil. LCMS [M+H]$^+$=274.

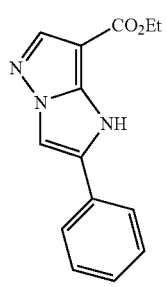

59C

To a rt solution of a 1:1 mixture of compounds 59A and 59B (1.48 g) in EtOH (20 mL) was added concentrated sulfuric acid (3 mL) and the resulting solution was heated at 75° C. for 15 minutes. The mixture was cooled to rt and was poured over crushed ice. After the solution had warmed to rt, the mixture was extracted with EtOAc (3×40 mL), and the combined extracts were washed with brine (20 mL), dried over anhydrous sodium sulfate, filtered, and concentrated in vacuo to afford a yellow semi-solid. This material was dissolved in EtOAc (15 mL), and hexanes slowly added (15 mL). The resulting solid was collected by vacuum filtration and was washed with a 1:1 EtOAc/hexanes mixture (3×20 mL). The resulting material was dried in vacuo to afford 0.2 g of compound 59C as a white solid. HPLC $t_R$=2.95 min. LCMS [M+H]$^+$=256.1.

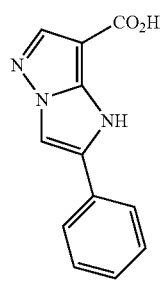

59D

A mixture of compound 59C (0.20 g) and 3 N aq. sodium hydroxide (1 mL) in MeOH (4 mL) was refluxed for 36 h. The mixture was cooled to rt and concentrated to remove the MeOH, then diluted with water (4 mL). The resulting mixture was acidified (pH~1) by addition of 20% aq. HCl. The resulting slurry was stirred for 20 minutes and the solid was collected by vacuum filtration and rinsed with additional water. The material was dried in vacuo to afford 140 mg (79%) of compound 59D as an off-white solid. HPLC $t_R$=2.39 min. LCMS [M+H]$^+$=228.1.

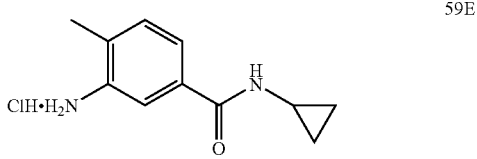

59E

A solution of 4-methyl-3-nitrobenzoyl chloride (69 g, 0.36 mol) in CH$_2$Cl$_2$ (400 mL) was cooled to 0° C., and then TEA (53 mL, 0.38 mol) was slowly added. A solution of cyclopropyl amine (25 g, 0.44 mol) in CH$_2$Cl$_2$ was added over 45 minutes while the internal reaction temperature was maintained below 5° C. The reaction was stirred for 1 h and then transferred to a separatory funnel with an additional 300 mL of CH$_2$Cl$_2$. This was then washed with 5% aq. HCl (500 mL) and brine (250 mL). The organic layer was dried over Na$_2$SO$_4$, filtered and concentrated. The crude solids were dissolved in hot EtOH (ca. 10 mL/g crude). Decolorizing carbon was added, and the reaction mixture was filtered through celite and concentrated again. The crude solid product was used directly in the next step. $^1$H NMR: (CDCl$_3$, 400 mHz) δ 8.23 (d, J=1.7 Hz, 1H), 7.87 (dd, J=1.7, 7.9 Hz, 1H), 7.24 (d, J=8 Hz, 1H), 6.44 (br s, 1H), 2.85 (m, 1H), 2.57 (s, 3H), 0.82 (m, 2H), 0.59 (m, 2H); LCMS [M+H]$^+$=221.1; HPLC $t_R$=2.71 min.

To a suspension of the above solid (90 g, 0.41 mol) in 1/1 EtOH/EtOAc (600 mL) was added an additional 200 mL of warm EtOH to aid with solubilizing the compound. To this solution was added 5% Pd—C (9 g, wet, Degussa type) and the mixture placed under hydrogen (45 psi) on a Parr shaker. Hydrogen was recharged at 10 minutes and 30 minutes. The reaction was shaken for 1 h and then filtered through celite. The filter was rinsed with EtOH (2×200 mL) and concentrated to an oil which solidified on standing. To a solution of the solidified oil (155 g, 0.81 mol) in absolute EtOH (1.55 L) at 0° C. was added HCl (70 mL, 12N) dropwise, while the internal temperature was maintained below 5° C. The solution was stirred at 0° C. for 4 h and filtered. The filter cake was washed with cold EtOH (2×125 mL). The solids were collected and dried under vacuum for 15 h to give 59E (162 g, 87% yield) as a white crystalline solid. $^1$H NMR (DMSO-D$_6$, 400 mHz) δ 9.5 (br s, 2H), 8.27 (s, 1H), 7.53 (s, 1H), 7.40 (d, J=7.6 Hz, 1H), 7.11 (m, 1H), 2.60 (m, 1H), 2.13 (s, 3H), 0.45 (m, 2H), 0.34 (m, 2H); LCMS [M+H]$^+$=191.1 (M+H); HPLC $t_R$=0.58 min.

Step F, Example 59

To a rt solution of compound 59D (30 mg, 0.13 mmol) and 59E (36 mg) in NMP (0.3 mL) were successively added DIPEA (0.028 mL, 0.16 mmol) and HATU (50 mg) and the resulting solution was heated to 60° C. for 15 h. The resulting reaction mixture was purified by reverse-phase preparative HPLC using a gradient elution of solvent A (solvent A=10%

MeOH/90% water/0.2% phosphoric acid) and solvent B (solvent B=90% MeOH/10% water/0.2% phosphoric acid). Fractions containing the product were neutralized by adding aq sodium bicarbonate and concentrated to remove the MeOH. The resulting aqueous slurry was filtered to collect the solid. The solid was dried in vacuo to afford 25 mg of Example 59 as an off-white solid. HPLC $t_R$=2.91 min. LCMS [M+H]$^+$=400.0.

Example 60

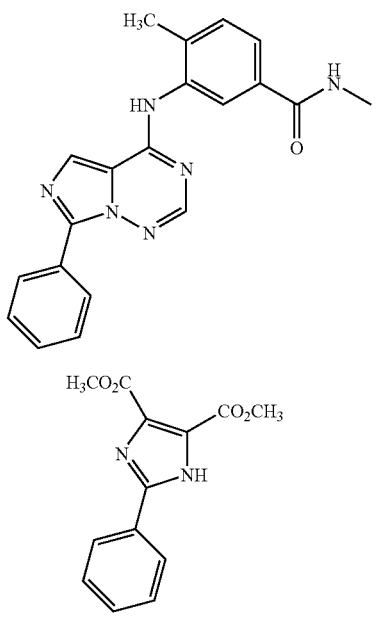

60A

The 2,3-(bis)carboxy-6-phenylimidazole starting material was prepared according to Bayon, J. C.; Net, G. J. Chem. Soc. Dalton Trans. 1987, 3003-3007. To a rt solution of 2,3-(bis) carboxy-6-phenylimidazole (10.8 g, 46.4 mmol) in MeOH (150 mL) was slowly added concentrated sulfuric acid (17 mL), and the resulting solution was refluxed for 20 h then cooled to rt. The mixture was cooled in an ice bath and aq 6N sodium hydroxide was slowly added until the solution was neutral (pH~7). The mixture was concentrated on a rotary evaporator to remove the MeOH, and the resulting aqueous slurry was filtered to collect a tan solid. The solid was washed with water (2×50 mL) and dried in vacuo in the presence of anhyd. phosphorus pentoxide to afford 9.5 g (79%) of 60A as a greyish-tan solid. HPLC $t_R$=2.28 min. LCMS [M+H]$^+$=261.8

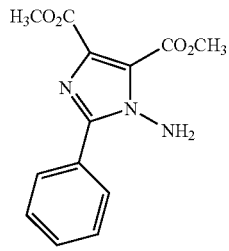

60B

A 60% dispersion of sodium hydride in mineral oil (0.8 g, 20.0 mmol) was washed with hexanes under an argon atmosphere then suspended in anhydrous DMF (28 mL) and cooled to 0° C. Compound 60A (4.0 g, 15.4 mmol) was added as a solid in four portions over 10 min, and the resulting mixture was stirred at 0° C. for 1 h. At this time, 2,4-dinitrophenylhydroxylamine (3.7 g, 18.5 mmol) was added as a solid in one portion, and the resulting mixture was allowed to warm to ambient temperature and stirred for 16 h. The mixture was quenched at 0° C. with water (150 mL), and the mixture was extracted with EtOAc (5×75 mL). The combined extracts were washed with water (3×50 mL) and brine (50 mL), then dried over anhydrous sodium sulfate, filtered, and concentrated in vacuo to afford 4 g of compound 60B as a dark brown oil. This material was used without any additional purification. HPLC $t_R$=2.10 min.

LCMS [M+H]$^+$=276.0.

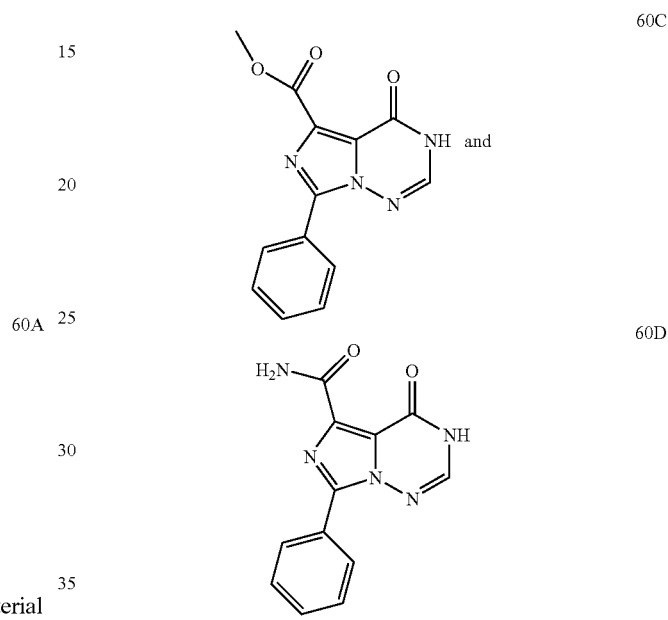

60B (4.0 g) was dissolved in triethyl orthoformate (18 mL) and heated to 150° C. for 4 h. The resulting mixture was cooled and the triethylorthoformate was removed via distillation. The resulting dark brown oil containing some residual triethylorthoformate was dissolved in 2 M ammonia in ethanol solution (28 mL) and was heated at 80° C. in a sealed reaction vessel for 2 h. At this time, the heterogeneous mixture was cooled in an ice-bath and the solid was collected by vacuum filtration and washed with additional ice-cold ethanol (3×20 mL). The resulting material was dried in vacuo to afford 1.9 g of a 3:2 mixture of compounds 60C and 60D as a tan solid. Compound 4: HPLC $t_R$=2.45 min. LCMS [M+H]$^+$=270.9. Compound 5: HPLC $t_R$=1.92 min. LCMS [M+H]$^+$=256.0.

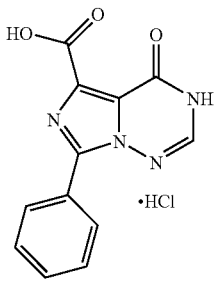

60E

To a 3:2 mixture of compounds 60C and 60D (1.8 g) was added 18 mL of concentrated HCl and the resulting mixture was heated at 80° C. for 16 h. After cooling to ambient temperature, the resulting solid was collected by vacuum filtration and was washed with ice-cold water (2×10 mL). The resulting material was dried in vacuo to afford 1.56 g of compound 60E as a light tan solid. HPLC $t_R$=1.99 min. LCMS [M+H]$^+$=257.1.

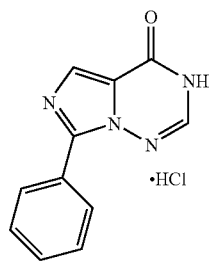

60F

Compound 60E (1.2 g) in 1-methyl-2-pyrrolidinone was heated at 250° C. in a microwave reactor for 30 min then cooled to rt. The mixture was concentrated in vacuo and the resulting residue was triturated with diethyl ether. The resulting solid was dried in vacuo to afford 1.02 g of compound 60F as a tan solid. HPLC $t_R$=1.88 min. LCMS [M+H]$^+$=213.1.

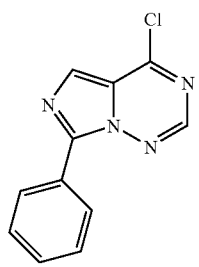

60G

A mixture of 60F (0.2 g), DIPEA (0.17 mL, 0.97 mmol), and phosphorus oxytrichloride (0.23 mL, 2.4 mmol) in toluene (3.5 mL) was heated at 75° C. for 16 h. The mixture was cooled to rt and concentrated in vacuo and the resulting residue was dissolved in dichloromethane (4 mL), and this solution was added to an ice-cold saturated aqueous solution of sodium bicarbonate. The mixture was allowed to warm to rt and stirred for 1 h. At this time, the biphasic mixture was filtered to remove some insoluble particulates and the filtrate was extracted with dichloromethane (3×10 mL). The combined extracts were washed with brine, dried over anhydrous sodium sulfate, and concentrated in vacuo to afford a brown semi-solid. This material was triturated with hexanes and the resulting solid was dried in vacuo to afford 178 mg of 60G as a tan solid. HPLC $t_R$=3.04 min. LCMS [M+H]$^+$=231.0.

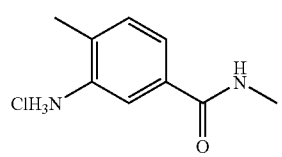

60H 60H was prepared following the same or similar method described for 59E in Example 59.

Step I, Example 60

A solution of 60G (30 mg, 0.13 mmol) and compound 60H (26 mg, 0.16 mmol) was stirred at rt for 16 h. The resulting reaction mixture was purified by reverse-phase preparative HPLC using a gradient elution of solvent A (solvent A=10% MeOH/90% water/0.2% phosphoric acid) and solvent B (solvent B=90% MeOH/10% water/0.2% phosphoric acid). Fractions containing the product were concentrated in vacuo and the resulting residue was treated with 1 equivalent of aqueous HCl and liophilized to afford 22 mg of Example 60 as a light tan solid.

HPLC $t_R$=2.77 min. LCMS [M+H]$^+$=359.1.

Examples 61-64

The following compounds in Table 6 have been synthesized utilizing the procedures described in Example 60 and the appropriate starting materials.

TABLE 6

| Ex. # | Structure | HPLC (RT) min | M + H |
|---|---|---|---|
| 61 | 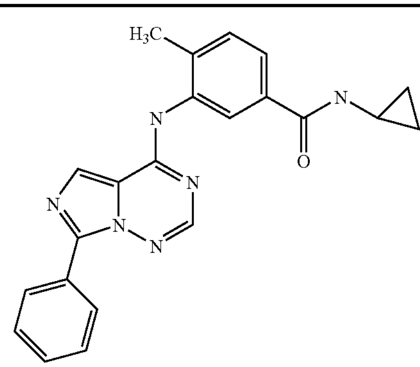 | 2.96 min | 385.1 |

TABLE 6-continued

| Ex. # | Structure | HPLC (RT) min | M + H |
|---|---|---|---|
| 62 | 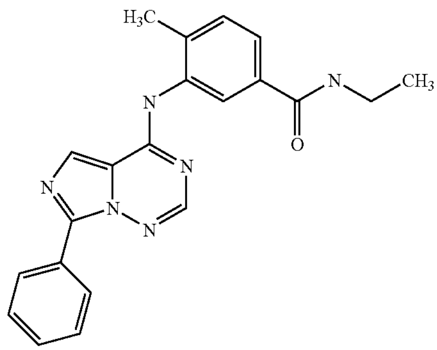 | 2.92 min | 373.1 |
| 63 | 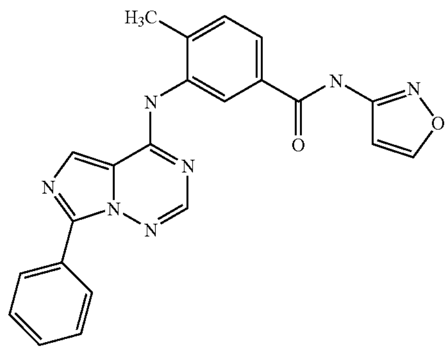 | 2.96 min | 412.0 |
| 64 | 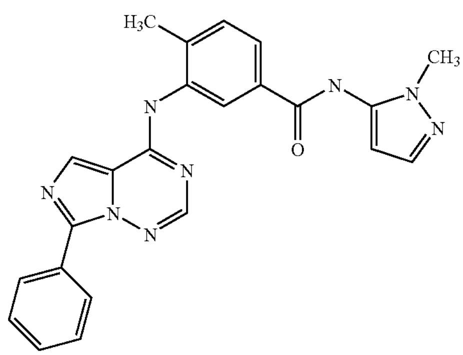 | 2.96 min | 425.0 |

Example 65

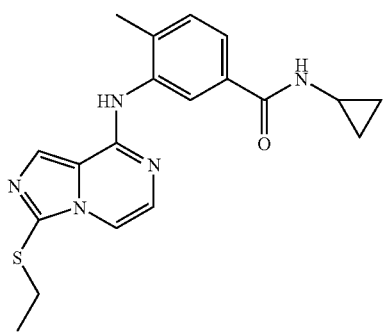

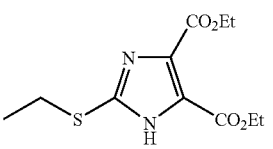

65A

To a solution of sodium ethoxide (1.64 g, 24.2 mmol) in absolute ethanol (120 mL) at rt under argon was added diethyl-2-thioimidazolyl-4,5-dicarboxylate (4.76 g, 22.0 mmol) as a solid in one portion. After stirrring for 15 min, iodoethane (2.11 mL, 26.4 mmol) was added dropwise and the reaction was stirred at rt for 2 h. After removal of ethanol in vacuo, cold water (100 mL) was added and the pH was adjusted to ~7 by addition of aqueous HCl (6N). The mixture was extracted with EtOAc (100 mL×4), and the combined extracts were washed with brine, dried over Na$_2$SO$_4$, filtered, and concentrated in vacuo to provide compound 65A as a light yellow semi-solid (4.88 g, 81.5% yield) which was used directly without any further purification.

HPLC Ret. Time: 2.43 min. MH$^+$ (m/z) 273. $^1$H NMR (500 MHz, CDCl$_3$, ppm): δ 1.36 (t, 9H), 3.20 (q, 2H), 4.40 (q, 4H), 10.04 (br. s, 1H).

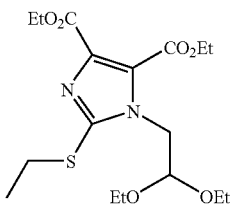

65B

A mixture of compound 65A (1.65 g, 6.06 mmol), cesium carbonate (5.90 g, 18.2 mmol), bromoacetaldehyde diethylacetal (2.80 mL, 18.2 mmol) and sodium iodide in DMF (6 mL) was heated at 100° C. for 20 h. The resulting mixture was cooled to rt and filtered through a pad of Celite and the filter cake was washed with three portions of EtOAc (20 mL). The resulting filtrate was concentrated in vacuo to afford compound 65B (2.48 g) as a light yellow oil. This material was used directly without any further purification. HPLC Ret. Time: 3.26 min. MH$^+$ (m/z) 389.

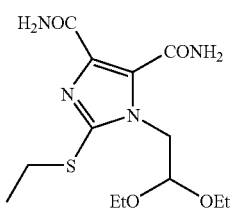

65C

Compound 65B (2.48 g, 6.06 mmol) and ammonium chloride (0.50 g, 9.34 mmol) in concentrated ammonium hydroxide was heated at 100° C. in a pressure bottle for 20 h. The mixture was cooled to rt and concentrated in vacuo to provide compound 65C (2.40 g) as a light yellow solid. This material was used directly without any further purification. HPLC Ret. Time: 2.63 min. MH$^+$ (m/z) 331.

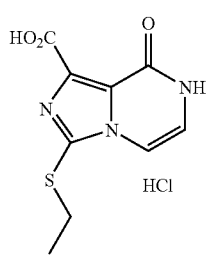

65D

Compound 65C (2.40 g) in concentrated HCl (15 mL) was stirred at rt for 20 h, then heated at 85° C. for 16 h. The resulting mixture was cooled to rt and concentrated in vacuo, and the resulting solid was treated with water and EtOAc. The precipitate was collected and washed with additional water to provide compound 65D as a brown solid (0.59 g, 35% yield over 4 steps) after drying in vacuo. HPLC Ret. Time: 1.59 min. MH$^+$ (m/z) 240. $^1$H NMR (500 MHz, DMSO-d$_6$, ppm): δ 1.28 (t, 3H), 3.20 (q, 2H), 7.00 (dd, 1H), 7.50 (d, 1H), 12.18 (br. s, 1H).

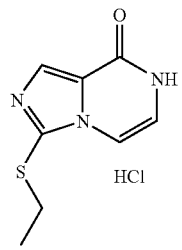

65E

Compound 65D (0.25 g) in 1-methyl-2-pyrrolidinone (3 mL) was heated in a microwave reactor to 230° C. for 10 min. This reaction was repeated three times with additional substrate, and the reaction mixtures were combined and concentrated in vacuo. The resulting residue was triturated with EtOAc and the precipitate was collected and washed with additional EtOAc to provide compound 65E as a black solid (0.79 g, 79% yield). HPLC Ret. Time: 1.25 min. MH$^+$ (m/z) 196. $^1$H NMR (500 MHz, DMSO-d$_6$, ppm): δ 1.22 (t, 3H), 3.07 (q, 2H), 6.68 (dd, 1H), 7.16 (d, 1H), 7.81 (s, 1H), 10.72 (br. s, 1H).

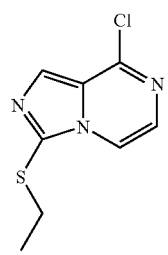

65F

To Compound 65E (0.20 g, 0.86 mmol) in toluene (4 mL) at rt under argon was added phosphorus oxychloride (0.24 mL, 2.59 mmol) followed by Hunig's base (0.18 mL, 1.04 mmol). The reaction was heated at 100° C. for 3 h then cooled to rt and quenched with 40 mL of saturated aqueous sodium bicarbonate and 10 mL of dichloromethane was added. After stirring at 0° C. for 1 h, the mixture was extracted with dichloromethane (50 mL×4). The combined extracts were dried over anhydrous sodium sulfate and concentrated in vacuo to give compound 65F (0.2 g) as a dark brown oil. This material was used directly without any further purification.

HPLC Ret. Time: 2.39 min. MH$^+$ (m/z) 214.

Step G, Example 65

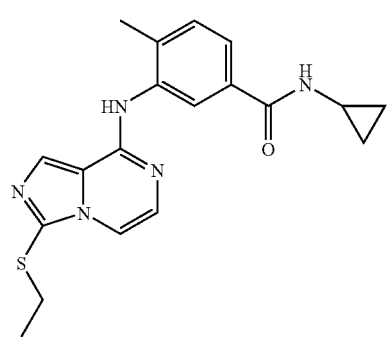

Compound 65F (3.32 g, 12.4 mmol) and compound 59E (0.20 g, 0.86 mmol) in DMF (2 mL) were heated under argon at 60° C. for 20 h. The resulting mixture was cooled to rt and quenched with 10 mL of saturated aqueous sodium bicarbonate and crushed ice. The mixture was stirred at room temperature for 1 h and the resulting solid was collected and washed with water to provide compound 65 as a grey solid (0.30 g, 94% over two steps). Ret. Time: 1.70 min. MH+ (m/z) 368. $^1$H NMR (500 MHz, DMSO-$d_6$, ppm): δ 0.55 (m, 2H), 0.67 (m, 2H), 1.17 (t, 3H), 2.25 (s, 3H), 2.82 (m, 1H), 3.02 (q, 2H), 7.08 (dd, 1H), 7.34 (d, 1H), 7.59 (d, 1H), 7.62 (d, 1H), 7.81 (s, 1H), 7.97 (s, 1H), 8.35 (d, 1H), 9.20 (s, 1H).

Examples 66-67

The following compounds in Table 7 were synthesized utilizing the procedures described in Example 65 by replacing iodoethane with iodomethane in preparation of 65A.

TABLE 7

| Ex # | Structure | HPLC RT (min) | M + H+ (m/z) |
|---|---|---|---|
| 66 | 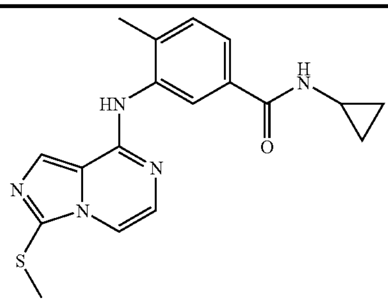 | 1.54 | 354 |
| 67 | 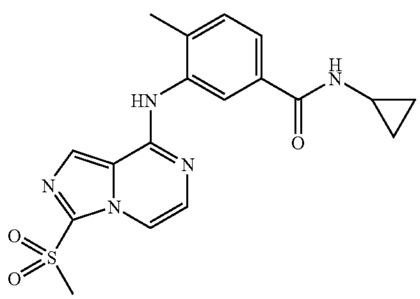 | 1.51 | 386 |

Example 68

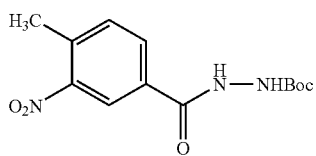
68A

To a rt solution of tert-butyl carbazate (2.6 g, 20 mmol) and triethylamine (3.1 mL, 22 mmol) in DCE (100 mL) was added a solution of 4-methyl-3-nitrobenzoyl chloride in DCE (25 mL) over 30 minutes. After the addition was complete, the resulting cloudy mixture was stirred at rt for 2 h, then the mixture was successively washed with 10% aqueous citric acid (2×75 mL) and brine (100 mL), then dried over anhydrous sodium sulfate. The solution was diluted with EtOAc (100 mL), filtered, and concentrated in vacuo to a volume of approximately 50 mL. The mixture was diluted with hexanes (50 mL) and sonicated for a few minutes and the resulting precipitated solid was collected by vacuum filtration and dried in vacuo to afford 4.7 g (74%) of 68A as a white solid. HPLC $t_R$=2.54 min. $^1$H NMR (400 MHz, $d_6$-DMSO): δ 10.30 (s, 1H), 8.86 (s, 1H), 8.27 (s, 1H), 7.91 (d, 1H), 7.48 (d, 1H), 2.41 (s, 3H), 1.26 (s, 9H).

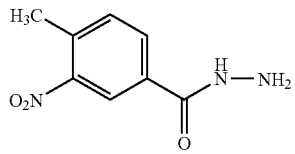
68B

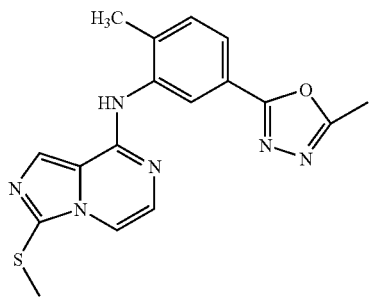

68A (4.4 g, 15 mmol) as a solid was added in portions to trifluoroacetic acid (45 mL) at 0° C., and the mixture was stirred at this temperature for 30 min and at rt for an additional 30 minutes. The mixture was then concentrated in vacuo and the resulting white solid was partitioned between 2N aq sodium carbonate (200 mL) and EtOAc (200 mL). The layers were separated and the aqueous portion was extracted with additional EtOAc (5×100 mL), and the combined extracts were washed with brine (100 mL), dried over anhydrous sodium sulfate, filtered, and concentrated in vacuo to yield 2.96 g (99%) of 68B as a white solid. HPLC $t_R$=1.05 min. $^1$H NMR (500 MHz, d$_6$-DMSO): δ 10.20 (br s, 1H), 8.42 (s, 1H), 8.05 (d, 1H), 7.62 (d, 1H), 5.43 (br s, 2H), 2.56 (s, 3H). LCMS [M+H]$^+$=196.3.

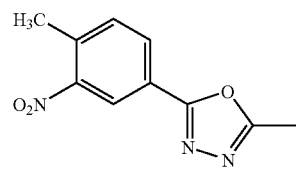

68C

A suspension of 68B (2.9 g, 15 mmol) in triethyl orthoacetate (50 mL) was heated to 100° C. giving a clear solution. After heating at this temperature for 2 h, the mixture was heated to 130° C. for an additional hour then cooled to rt and heterogeneously concentrated in vacuo. The resulting residue was dissolved in EtOAc (250 mL) and washed with water (100 mL) and brine (75 mL) then dried over anhydrous sodium sulfate, filtered, and concentrated in vacuo to afford 3.2 g of 68C as a light yellow solid. HPLC $t_R$=2.45 min. $^1$H NMR (500 MHz, CDCl$_3$): δ 8.57 (s, 1H), 8.16 (d, 1H), 7.49 (d, 1H), 2.66 (s, 3H), 2.63 (s, 3H).

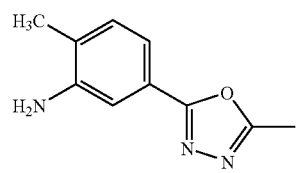

68D

To a suspension of 68C (0.37 g) in ethanol (40 mL) was added 5% palladium on carbon (35 mg) and the mixture was allowed to stir under an atmosphere of hydrogen at rt for 2 h. The mixture was filtered through Celite and the resulting clear filtrate was concentrated in vacuo and the residue was triturated with MeOH. Filtration and drying of the collected solid afforded 220 mg of 68D as an off-white solid. HPLC $t_R$=1.19 min. $^1$H NMR (500 MHz, d$_6$-DMSO): δ 7.23 (s, 1H), 7.08 (d, 1H), 7.05 (d, 1H), 5.22 (s, 2H), 2.53 (s, 3H), 2.10 (s, 3H). LCMS [M+H]$^+$=190.3.

Step E, Example 68

The title compound 68 was prepared following the same procedure as described for Example 65 using compound 68D. HPLC Retention time=1.57 min.

LCMS [M+H]$^+$=353.0.

Example 69

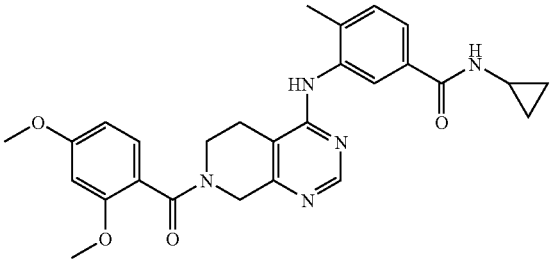

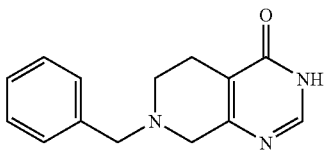

69A

To a slurry of sodium methoxide (10.0 g, 185 mmol) in anhydrous MeOH (60 mL) at room temperature was added formamidine acetate (6.60 g, 63.4 mmole) followed by ethyl-1-benzyl-3-oxo-4-piperidine-carboxylate (15.8 g, 52.9 mmol) in one portion. After stirring at rt for 20 h, the mixture was cooled to 10° C. whereupon 36 mL of water was added followed by 3.8 mL of acetic acid, and the mixture was stirred for an additional hour. The resulting mixture was concentrated and 150 mL of water was added. The solid was collected by filtration and washed with water and air dried. The crude product (9.60 g) was purified by recrystallization from MeOH (~100 mL) to provide 69A as near white needles (7.86 g, 61.8% yield). HPLC Ret. Time: 0.46 min. MH$^+$ (m/z) 253. $^1$H NMR (400 MHz, CDCl$_3$, ppm): δ 2.65 (t, 3H), 2.75 (t, 3H), 3.50 (s, 2H), 3.70 (s, 2H), 7.35 (m, 5H), 7.98 (s, 1H).

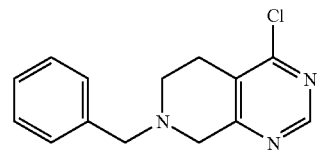

69B

To 69A (3.00 g, 12.4 mmol) in toluene (40 mL) at room temperature was added phosphorus oxychloride (2.28 g, 14.9 mmol) followed by Hunig's base (1.28 g, 9.92 mmol) and the reaction was heated to 100° C. for 30 minutes then cooled to rt. The resulting mixture was quenched with 200 mL of saturated aqueous sodium bicarbonate solution and 200 mL of crushed ice. After stirring at room temperature for 1 h, the mixture was then extracted with dichloromethane (100 mL×4). The combined organic extracts were dried over sodium sulfate and concentrated in vacuo to give 3.32 g of 69B (~100%) as a dark brown oil that was used directly without any further purification. HPLC Ret. Time: 0.95 min. MH$^+$ (m/z) 260.

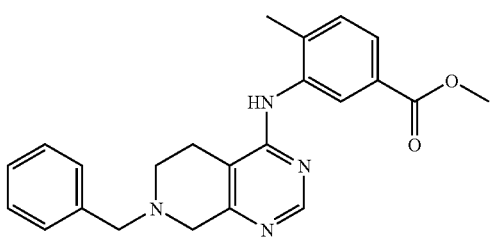

69C

To a rt solution of 69B (3.32 g, 12.4 mmol) and methyl-3-amino-4-methylbenzoate (1.84 g, 11.2 mmol) in NMP (30 mL) was added a 4 N solution of anhydrous HCl in dioxane (10 mL) and the resulting mixture was heated at 80° C. for 20 h. After cooling to rt, the reaction was quenched with 100 mL of saturated aqueous sodium bicarbonate and crushed ice. The mixture was stirred at room temperature for 1 h. The solid was collected by vacuum filtration and washed with water and air dried to afford 69C as a near black solid (4.68 g). This material was used directly without any further purification. Ret. Time: 1.76 min. MH+ (m/z) 389.

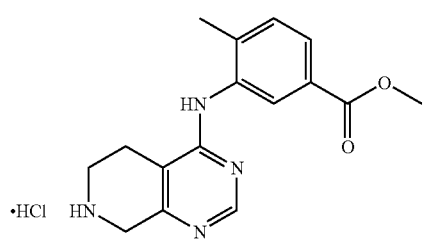

69D

To 69C (4.68 g) in MeOH (100 mL) were added palladium on carbon (500 mg, 10% wt.) and concentrated aqueous hydrogen chloride (4 mL) and the mixture was hydrogenated under hydrogen (50 psi) for 20 h. The solution was filtered through a bed of celite and the solvent was removed in vacuo to give 4.78 g of 69D as a light brown thick oil that was used directly without any further purification. HPLC Ret. Time: 0.99 min. MH+ (m/z) 299. $^1$H NMR (500 MHz, CDCl$_3$, ppm): δ 2.31 (s, 3H), 3.07 (t, 2H), 3.72 (t, 2H), 3.89 (s, 3H), 4.51 (s, 2H), 7.49 (d, 1H), 7.92 (d, 1H), 7.95 (dd, 1H), 8.64 (s, 1H).

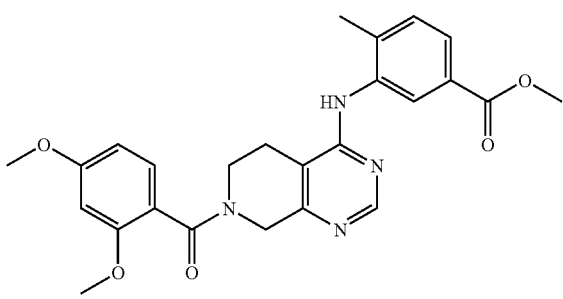

69E

To 2,4-dimethoxybenzoic acid (0.122 g, 0.70 mmol) in DMF (2 mL) were added 1-hydroxybenzotriazole (0.098 g, 0.72 mmol), 1-[3-(dimethylamino)propyl]-3-ethylcarbodiimide hydrochloride (0.138 g, 0.72 mmole), DIPEA (0.22 mL, 1.28 mmol) and 69D (0.18 g, 0.52 mmol) sequentially at room temperature, and the resulting mixture was stirred for 1 h. Water was added and the solid was collected by vacuum filtration to give 69E (0.24 g) as a pale yellow solid. HPLC Ret. Time: 2.2 min. MH+ (m/z) 464.

69F

To 69E (0.24 g, 0.67 mmol) in MeOH (2 mL) at room temperature was added 3N aqueous potassium hydroxide solution (0.7 mL, 2.0 mmol) and the mixture was stirred for 20 h. After the solvent was removed in vacuo, the mixture was brought to pH 1 with 1N HCl and the resulting solid was collected by filtration to give 69F (0.19 g, 82.6%) as a pale yellow solid. HPLC Ret. Time: 1.95 min. MH+ (m/z) 449.

Step G, Example 69

To compound 69F (0.020 g, 0.045 mmol) in DMF (0.3 mL) was added 1-hydroxybenzotriazole (0.007 g, 0.054 mmol), 1-[3-(dimethylamino)propyl]-3-ethylcarbodiimide hydrochloride (0.010 g, 0.054 mmol), DIPEA (0.015 ml, 0.089 mmol) and cyclopropylamine (0.004 g, 0.067 mmol) sequentially at room temperature and the mixture was stirred for 16 h. The resulting mixture was subjected to purification by reverse-phase preparative HPLC and the trifluoroacetic acid salt of Example 69 was isolated as a white solid. HPLC Ret. Time: 1.97 min. MH+ (m/z) 488. $^1$H NMR (400 MHz, CD$_3$OD, rotamers ppm): δ 0.55 (m, 2H), 0.68 (m, 2H), 2.15 (s, 3H), 2.60 (m, 1H), 2.70 (t, 2H), 3.64 (t, 2H), 3.80 (four sets of s, 6H), 4.00 (br. dd, 1H), 4.40 (br. dd., 1H), 6.50 (d, 1H), 6.60 (d, 1H), 7.15 (d, 1H), 7.30 (d, 1H), 7.55 (s, 1H), 7.60 (s, 1H) 8.28 (s, 1H), 8.42 (s, 1H).

Examples 70-76

The compounds in Table 8 having the formula (8*) below, wherein R has the values reported in Table 8, were synthesized utilizing the procedures described in Example 69 from 69F and the appropriate starting materials.

TABLE 8

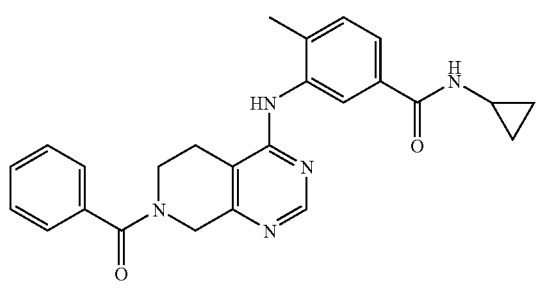

(8*)

| Example # | R | HPLC RT (min) | Mass Spec. M + H+ (m/z) |
|---|---|---|---|
| 70 | —CH₃ | 1.80 | 462 |
| 71 | ethyl | 1.94 | 476 |
| 72 | propyl | 2.11 | 490 |
| 73 | butyl | 2.34 | 504 |
| 74 | cyclobutyl | 2.19 | 502 |
| 75 | CH₂CH₂OH | 1.76 | 492 |
| 76 | CH₂CH₂OMe | 1.91 | 506 |

Example 77

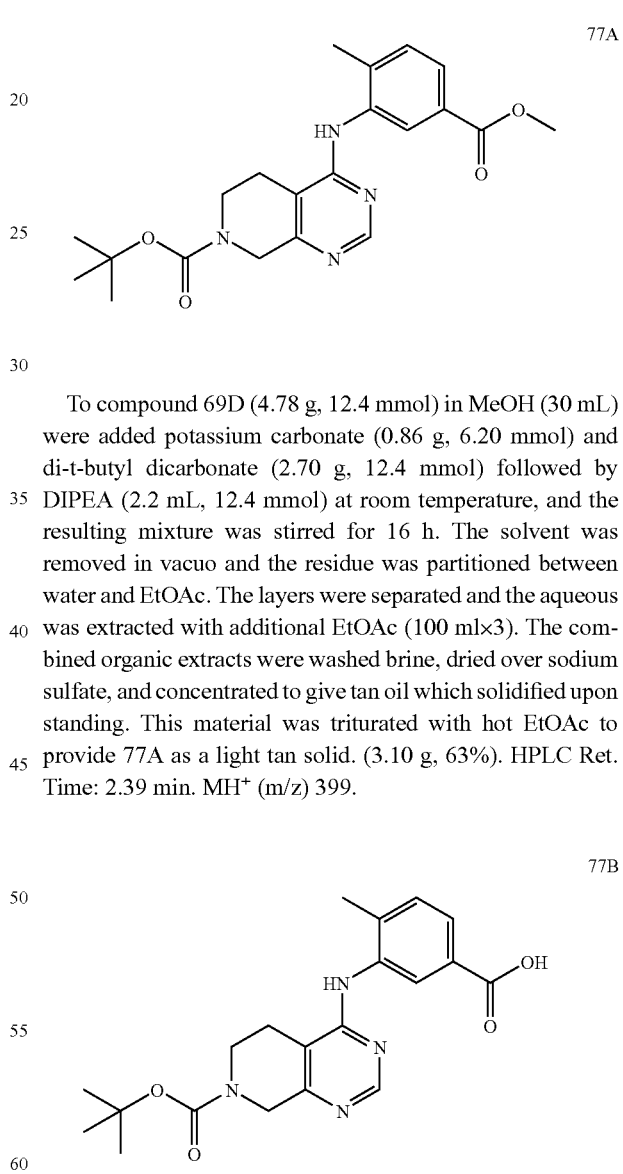

To compound 69D (4.78 g, 12.4 mmol) in MeOH (30 mL) were added potassium carbonate (0.86 g, 6.20 mmol) and di-t-butyl dicarbonate (2.70 g, 12.4 mmol) followed by DIPEA (2.2 mL, 12.4 mmol) at room temperature, and the resulting mixture was stirred for 16 h. The solvent was removed in vacuo and the residue was partitioned between water and EtOAc. The layers were separated and the aqueous was extracted with additional EtOAc (100 ml×3). The combined organic extracts were washed brine, dried over sodium sulfate, and concentrated to give tan oil which solidified upon standing. This material was triturated with hot EtOAc to provide 77A as a light tan solid. (3.10 g, 63%). HPLC Ret. Time: 2.39 min. MH+ (m/z) 399.

77B was prepared following the same procedure as described for 69F. HPLC Ret. Time: 2.16 min. MH+ (m/z) 385.

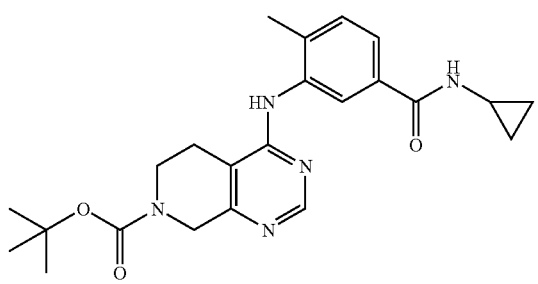

77C

Compound 77C was prepared from 77B following the same procedure as described for Example 69. HPLC Ret. Time: 2.16 min. MH+ (m/z) 424.

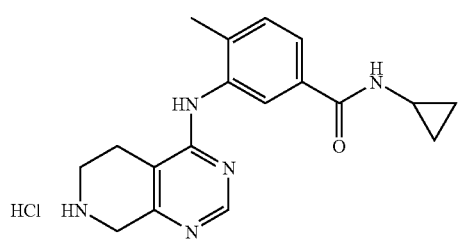

77D

To a slurry of 77C (0.68 g, 1.60 mmol) in 1,4-dioxane (3 mL) at room temperature was added hydrogen chloride solution (4 M in 1,4-dioxane) and the mixture was stirred for 16 h. Ether (25 mL) was added and the solid was collected by filtration and washed with additional ether to give 77D as a near white (0.57 g, 99% yield). HPLC Ret. Time: 0.69 min. MH+ (m/z) 324.

Step E, Example 77

To 77D (0.040 g, 0.11 mmol) in dichloromethane (0.4 mL) was added benzoyl chloride (0.025 g, 0.22 mmol) and DIPEA (0.048 mL, 0.28 mmol) at room temperature, and the mixture was stirred at rt for 14 h. The solvent was removed in vacuo and the resulting mixture was purified by reverse-phase preparative HPLC. The title compound was isolated as its trifluoroacetic acid salt as a white solid. HPLC Ret. Time: 1.82 min. MH+ (m/z) 428. $^1$H NMR (400 MHz, CD$_3$OD, ppm): δ 0.55 (m, 2H), 0.80 (m, 2H), 2.24 (s, 3H), 2.80 (m, 3H), 3.85 (m 1H), 4.15 (m, 1H), 4.86 (m, 2H), 7.40 (d, 1H), 7.55 (m, 5H), 7.60 (d, 1H), 7.65 (s, 1H), 8.45 (br. s, 1H).

Examples 78-97

The following compounds having formula (9*), below, wherein R has the values reported in Table 9, were synthesized utilizing the procedures described in Example 77 from 77D and by substituting benzoyl chloride with dimethylsulfonyl hydrochloride, ethyl isocyanate, benzyl isocyanate, ethyl chloroformate, benzyl chloroformate, 1,2-dimethylimidazol-4-sulphonyl chloride, 4-fluorophenylsulphonyl chloride, 4-cyanophenylsulphonyl chloride, 4-methoxyphenylsulphonyl chloride, benzylsulphonyl chloride, phenyl isocyanate, 3-cyanobenzoyl chloride, 3-fluorobenzoyl chloride, 4-fluorobenzoyl chloride, 3-methoxybenzoyl chloride, 3-fluoro-4-trifluoromethylbenzoyl chloride, and morpholinyl-1-sulfamoyl chloride, respectively.

TABLE 9

(9*)

| Ex # | R | HPLC Ret. Time (min) | Mass Spec. M + H+ (m/z) |
|---|---|---|---|
| 78 | dimethylaminosulfonyl | 1.57 | 431 |
| 79 | ethylaminocarbonyl-dimethyl | 1.46 | 395 |
| 80 | benzylaminocarbonyl-dimethyl | 2.02 | 457 |
| 81 | ethoxycarbonyl-dimethyl | 1.96 | 396 |
| 82 | benzyloxycarbonyl-dimethyl | 2.32 | 458 |
| 83 | 1,2-dimethylimidazol-4-sulfonyl | 1.50 | 482 |
| 84 | 4-fluorophenylsulfonyl | 2.11 | 482 |
| 85 | 4-cyanophenylsulfonyl | 2.01 | 489 |

TABLE 9-continued (9*)

| Ex # | R | HPLC Ret. Time (min) | Mass Spec. M + H+ (m/z) |
|---|---|---|---|
| 86 | 4-methoxyphenyl sulfonyl | 2.08 | 494 |
| 87 | benzyl sulfonyl | 1.96 | 478 |
| 88 | phenyl-NH-C(O)-C(CH3)2- | 1.95 | 443 |
| 89 | 3-cyanophenyl-C(O)-C(CH3)2- | 1.70 | 453 |
| 90 | 3-fluorophenyl-C(O)-C(CH3)2- | 1.88 | 446 |
| 91 | 4-fluorophenyl-C(O)-C(CH3)2- | 1.86 | 446 |
| 92 | 3-methoxyphenyl-C(O)-C(CH3)2- | 1.93 | 458 |
| 93 | 3-fluoro-4-trifluoromethylphenyl-C(O)-C(CH3)2- | 2.45 | 514 |
| 94 | morpholino sulfonyl | 1.62 | 473 |
| 95 | CH3-C(O)-C(CH3)2- | 1.23 | 366 |
| 96 | ethyl sulfonyl | 1.45 | 416 |
| 97 | phenyl sulfonyl | 1.97 | 464 |

Examples 98-100

The following compounds having the formula (10*), wherien R has the values reported in Table 10 were synthesized utilizing the procedures described in Example 69 from 77D and by substituting 2,4-dimethoxybenzoic acid with picolinic acid, nicotinic acid and 4-picolinic acid respectively.

TABLE 10

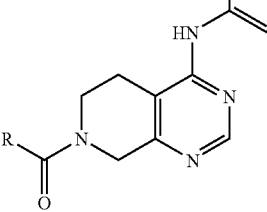

(10*)

| Example # | R | HPLC Ret. Time (min) | Mass Spec. M + H⁺ (m/z) |
|---|---|---|---|
| 98 | 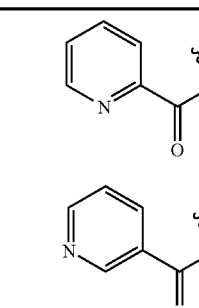 | 1.50 | 429 |
| 99 | 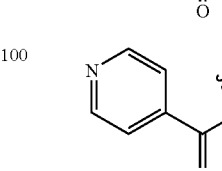 | 1.17 | 429 |
| 100 | 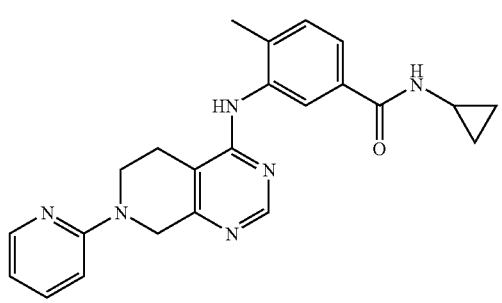 | 1.05 | 429 |

Example 101

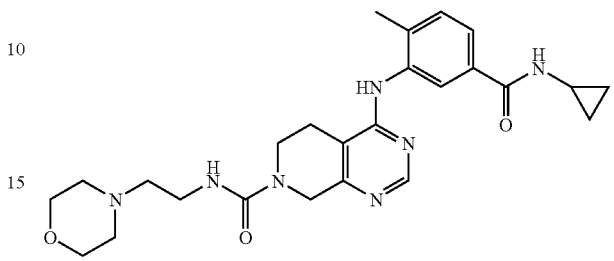

To 77D (0.030 g, 0.083 mmol) in tributylamine (0.4 mL) was added 2-fluoropyridine (0.15 mL, 1.67 mmol) at room temperature and the reaction mixture was heated at 150° C. for 6 h. After cooling to rt, the solvent was removed in vacuo and the resulting mixture was purified by reverse-phase preparative HPLC to afford the mono-trifluoroacetic acid salt of the title compound. HPLC Ret. Time: 1.32 min. MH⁺ (m/z) 401.

Example 102

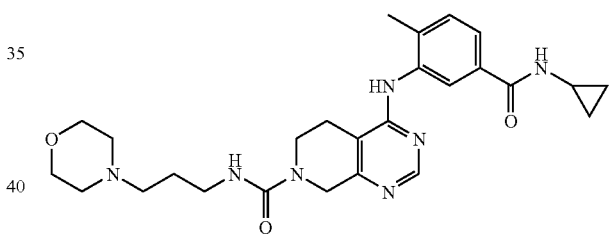

To 77D (0.040 g, 0.11 mmol) in dichloroethane (0.4 mL) was added 1,1'-carbonyldiimidazole (0.036 g, 0.22 mmol) and triethylamine (0.031 mL, 0.22 mmol) at 0° C. After stirring for 2 h, 4-(2-aminoethyl)morpholine (0.029 g, 0.22 mmole) was added and the mixture was stirred at room temperature for 20 h. The solvent was removed in vacuo and the resulting residue was purified by reverse-phase preparative HPLC to afford the mono-trifluoroacetic acid salt of the title compound. HPLC Ret. Time: 0.95 min. MH⁺ (m/z) 480.

Example 103

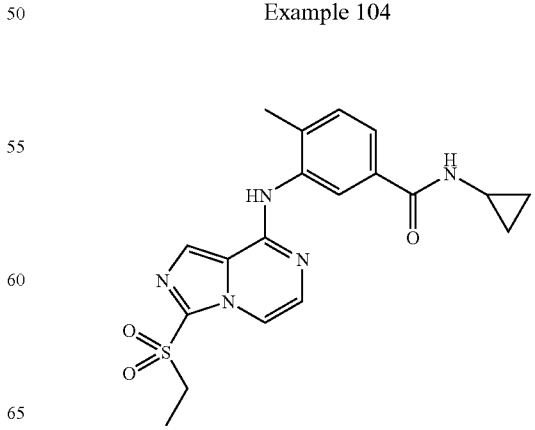

Example 103 was prepared from 77D utilizing a similar procedure used for the preparation of Example 102 and by substituting 4-(2-aminoethyl)morpholine with 4-(3-aminopropyl)morpholine. HPLC Ret. Time: 1.06 min. MH⁺ (m/z) 494.

Example 104

To Example 65 (150 mg, 0.408 mmol) in MeOH (1.5 mL) at 0° C. was added a solution of Oxone® (0.75 g, 1.22 mmol) in 1.5 ml of water. The resulting mixture was stirred at 0° C. for 1 h, then at rt for 3 h. The MeOH was removed in vacuo and the resulting solid was washed with water to give example 104a tan solid (146 mg, 89%).

HPLC Ret. Time: 1.77 min. MH+ (m/z) 400. $^1$H NMR (500 MHz, DMSO-$d_6$, ppm): δ 0.49 (m, 2H), 0.62 (m, 2H), 1.12 (t, 3H), 2.18 (s, 3H), 2.78 (m, 1H), 3.52 (q, 2H), 7.18 (d, 1H), 7.37 (d, 1H), 7.67 (d, 1H), 7.78 (s, 1H), 8.06 (d, 1H), 8.20 (s, 1H), 8.35 (d, 1H).

We claim:

1. A compound having the formula (I)

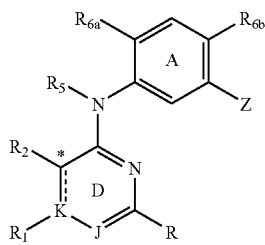

a pharmaceutically-acceptable salt thereof, or an enantiomer or a stereoisomer thereof, wherein:

J is —$CR_8$;

K is nitrogen, wherein the bond between K and carbon atom C* is a single bond;

Z is selected from —$NHR_{11}$, —$C(=O)NR_{11}R_{12}$, —$NR_{11}C(O)_2R_{12}$, —$NR_{11}C(=O)R_{13}$, —$NR_{11}C(=O)NR_{12}R_{13}$, —$NR_{11}SO_2R_{14}$, —$SO_2NR_{12}$, —$C(=O)R_{12}$, —$OC(=O)R_{15}$, —$C(=O)NR_{11}C(=O)R_{13}$, —$C(=O)NR_{11}C(=O)NR_{12}R_{13}$, and optionally-substituted heteroaryl;

$R_5$ is hydrogen or $C_{1-4}$alkyl;

$R_{6a}$ and $R_{6b}$ are independently selected from hydrogen, $C_{1-4}$alkyl, hydroxy, methoxy, halogen, cyano, amino, —$NH(C_{1-4}alkyl)$, —$N(C_{1-4}alkyl)_2$, —$CF_3$, —$OCF_3$, and $C_{1-4}$alkyl substituted with one or two of hydroxy, methoxy, halogen, cyano, amino, —$NH(C_{1-4}alkyl)$, —$N(C_{1-4}alkyl)_2$—$CF_3$, and/or —$OCF_3$;

R is selected from hydrogen, alkyl, substituted alkyl, hydroxy, alkoxy, halogen, cyano, amino, alkylamino, haloalkoxy, cycloalkyl, aryl, heterocyclo, and heteroaryl;

$R_1$ and $R_2$ are taken together to form a ring fused to ring D via bond K┄┄* , wherein $R_1$ and $R_2$ (considered together with K, the C* atom, and the bond joining K and C*), form a fused ring selected from one of:

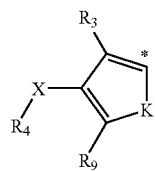

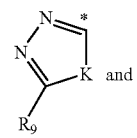

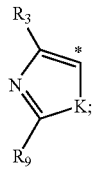

X is selected from —O—, —OC(=O)—, —S—, —S(=O)—, —$SO_2$, —C(=O)—, —$CO_2$—, —$NR_{15}$—, —$NR_{15}C(=O)$—, —$NR_{15}C(=O)NR_{15a}$—, —$NR_{15}CO_2$—, —$NR_{15}SO_2$—, —$NR_{15}SO_2NR_{15a}$—, —$SO_2NR_{15}$—, —C(=O) $NR_{15}$—, halogen, nitro, and cyano, or X is absent;

$R_3$ is hydrogen, methyl, perfluoromethyl, methoxy, halogen, cyano, $NH_2$, or $NH(CH_3)$;

$R_4$ is selected from:

(a) hydrogen, provided that $R_4$ is not hydrogen if either X is —S(=O)—, —$SO_2$—, —$NR_{15}CO_2$—, or —$NR_{15}SO_2$—, or $X_1$ is —$NR_{15}CO_2$—, or —$NR_{15}SO_2$—;

(b) alkyl, alkenyl, and alkynyl optionally independently substituted with keto and/or one to four $R_{17}$;

(c) aryl and heteroaryl either of which may be optionally independently substituted with one to three $R_{16}$; and (d) heterocyclo and cycloalkyl either of which may be optionally independently substituted with keto and/or one to three $R_{16}$; or (e) $R_4$ is absent if X is halogen, nitro, or cyano or if $X_1$ is nitro;

$R_9$ is selected from hydrogen, alkyl, substituted alkyl, halogen, cyano, aryl, heteroaryl, —$SR_{10}$, and —$S(O)_2R_{10}$, wherein $R_{10}$ is alkyl or substituted alkyl;

$R_{11}$ is hydrogen, alkyl, or substituted alkyl;

$R_{12}$, $R_{13}$ and $R_{14}$ are independently selected from hydrogen, alkyl, substituted alkyl, alkenyl, substituted alkenyl, hydroxy, alkoxy, aryl, cycloalkyl, heteroaryl, and heterocyclo, except $R_{14}$ is not hydrogen;

$R_{15}$ and $R_{15a}$ are independently selected from hydrogen, alkyl, substituted alkyl, aryl, cycloalkyl, heterocyclo, and heteroaryl;

$R_{16}$ is selected from alkyl, $R_{17}$, and $C_{1-4}$alkyl substituted with keto (=O) and/or one to three $R_{17}$;

$R_{17}$ is selected from (a) halogen, haloalkyl, haloalkoxy, nitro, cyano, —$SR_{23}$, —$OR_{23}$, —$NR_{23}R_{24}$, —$NR_{23}SO_2R_{25}$, —$SO_2R_{25}$, —$SO_2NR_{23}R_{24}$, —$CO_2R_{23}$, —C(=O) $R_{23}$, —C(=O)$NR_{23}R_{24}$, —OC(=O)$R_{23}$, —OC (=O)$NR_{23}R_{24}$, —$NR_{23}C(=O)R_{24}$, —$NR_{23}CO_2R_{24}$;

(b) aryl or heteroaryl either of which may be optionally substituted with one to three $R_{26}$; or (c) cycloalkyl or heterocyclo optionally substituted with keto(=O) and/or one to three $R_{26}$;

$R_{23}$, $R_{24}$ and $R_{25}$ are each independently selected from hydrogen, alkyl, alkenyl, substituted alkyl, substituted alkenyl, aryl, cycloalkyl, heteroaryl, and heterocyclo, except $R_{25}$ is not hydrogen;

$R_{26}$ is at each occurrence independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, $C_{1-4}$alkoxy, $C_{1-4}$alkylthio, phenyl, five to six membered heterocyclo, (phenyl)$C_{1-4}$alkyl, phenoxy, and (phenyl)$C_{1-4}$alkoxy; and p is 0, 1, 2 or 3.

2. A compound according to claim 1, or a pharmaceutically-acceptable salt thereof, wherein:

J, K, $R_1$ and $R_2$ are selected such that ring D and the ring fused thereto as defined by $R_1$ and $R_2$ form a bicyclic group selected from one of:

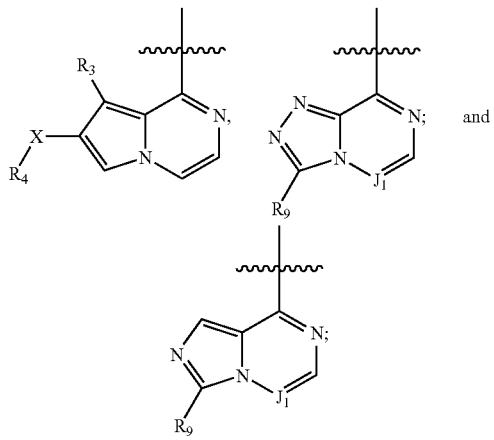

J is CH;

$R_3$ is methyl;

X is selected from —C(=O)—, —C(=O)—O—, —S(O)$_2$—, —S(O)$_2$NR$_{14}$—, and —C(=O)NR$_{14}$—, wherein $R_{14}$ is hydrogen or alkyl;

$R_4$ is selected from hydrogen; alkyl optionally independently substituted with keto and/or one to three $R_{17}$; aryl and heteroaryl either of which may be optionally independently substituted with one to three $R_{16}$; and heterocyclo and cycloalkyl either of which may be optionally independently substituted with keto and/or one to three $R_{16}$;

$R_9$ is selected from $C_{1-6}$alkyl, halogen, cyano, phenyl, —SR$_{10}$, and —S(O)$_2$R$_{10}$, wherein $R_{10}$ is $C_{1-4}$alkyl;

$R_{16}$ is selected from $C_{1-4}$alkyl, $R_{17}$, and $C_{1-4}$alkyl substituted with keto (=O) and/or one to three $R_{17}$;

$R_{17}$ is selected from halogen, haloalkyl, haloalkoxy, cyano, aryl or heteroaryl either of which may be optionally substituted with one to three $R_{26}$; and cycloalkyl or heterocyclo optionally substituted with keto(=O) and/or one to three $R_{26}$; and $R_{26}$ is selected from $C_{1-4}$alkyl, halogen, cyano, $C_{1-4}$alkoxy, —CF$_3$, and —OCF$_3$.

3. A compound according to claim 1, or a pharmaceutically-acceptable salt thereof, wherein $R_1$ and $R_2$ taken together (with K, the C* atom, and the bond joining K and C*), form $T_1$ or $T_2$, and J is CH.

4. A compound according to claim 1, or a pharmaceutically-acceptable salt thereof, wherein, $R_5$ is hydrogen;

$R_{6a}$ is methyl; and $R_{6b}$ is hydrogen.

5. A compound according to claim 1, or a pharmaceutically-acceptable salt thereof, wherein, Z is selected from —C(=O)NR$_{11}$R$_{12}$, —NR$_{11}$C(O)$_2$R$_{12}$, —NR$_{11}$(C=O)NHR$_{12}$, and five membered heteroaryl optionally substituted with $C_{1-4}$alkyl;

$R_{11}$ is hydrogen or $C_{1-4}$alkyl;

$R_{12}$ is $C_{1-4}$alkyl, $C_{1-4}$alkoxy, cyclopropyl, halo($C_{1-4}$alkyl), or a heteroaryl selected from pyrazolyl, oxazolyl, and isoxazolyl in turn optionally substituted with $C_{1-4}$alkyl; and $R_{13}$ is selected from phenyl and pyridyl in turn optionally substituted by one to three $R_{26}$, wherein $R_{26}$ is selected from halogen, cyano, and morpholinyl.

6. A compound according to claim 5, or a pharmaceutically-acceptable salt thereof, wherein, Z is —C(=O)NR$_{11}$R$_{12}$, wherein $R_{11}$ is hydrogen or $C_{1-4}$alkyl, and $R_{12}$ is selected from $C_{1-4}$alkyl, $C_{1-4}$alkoxy, and cyclopropyl.

7. A compound according to claim 1, having the formula I(T1):

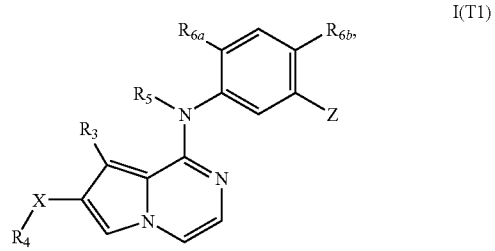

or a pharmaceutically-acceptable salt thereof.

8. A compound according to claim 7, having the formula I(T1*):

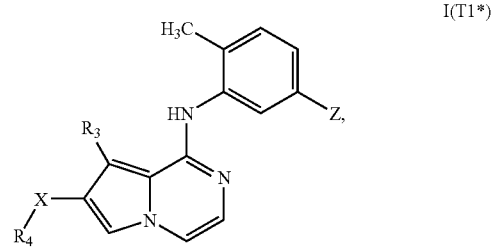

or a pharmaceutically-acceptable salt thereof, wherein

X is —C(=O)NR$_{14}$— (attached to the pyrrolyl group via the carbonyl), wherein $R_{14}$ is hydrogen or $C_{1-4}$alkyl;

$R_4$ is selected from $C_{1-6}$alkyl, benzyl, $C_{1-6}$alkoxy, $C_{3-7}$cycloalkyl, and N-morpholinyl; and Z is selected from NHR$_{11}$, —C(=O)NR$_{11}$R$_{12}$, —NR$_{11}$C(O)$_2$R$_{12}$, —NR$_{11}$(C=O)R$_{13}$, and —NR$_{11}$(C=O)NR$_{12}$, wherein $R_{11}$ is hydrogen or $C_{1-4}$alkyl; $R_{12}$ is $C_{1-4}$alkyl, $C_{1-4}$alkoxy, cyclopropyl, or halo($C_{1-4}$alkyl); and $R_{13}$ is selected from phenyl and pyridyl in turn optionally substituted by one to three $R_{26}$, wherein $R_{26}$ is selected from halogen, cyano, and morpholinyl.

9. A compound according to claim 1, having the formula I(T2):

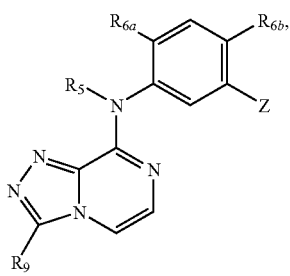

I(T2)

or a pharmaceutically-acceptable salt thereof.

10. A compound according to claim 9, having the formula I(T2*):

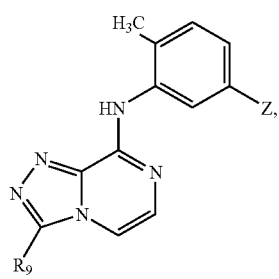

I(T2*)

or a pharmaceutically-acceptable salt thereof, wherein $R_9$ is $C_{1-6}$alkyl or phenyl; and Z is —C(O)NR$_{11}$R$_{12}$, wherein R$_{11}$ is hydrogen or C$_{1-4}$alkyl and R$_{12}$ is C$_{1-4}$alkyl, cyclopropyl, or a heteroaryl selected from pyrazolyl, oxazolyl, and isoxazolyl in turn optionally substituted with C$_{1-4}$alkyl.

11. A compound according to claim 1, having the formula I (T3):

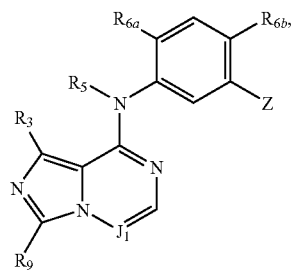

I(T3)

or a pharmaceutically-acceptable salt thereof, wherein $J_1$ is CH.

12. A pharmaceutical composition comprising at least one compound according to claim 1 or a pharmaceutically acceptable salt thereof and a pharmaceutically-acceptable carrier or diluent.

13. A method of treating rheumatoid arthritis comprising administering to a patient in need of such treatment an effective amount of a compound according to claim 1 in an amount of from about 0.05 to 100 mg/kg of body weight per day.

* * * * *

UNITED STATES PATENT AND TRADEMARK OFFICE
CERTIFICATE OF CORRECTION

PATENT NO.         : 7,642,257 B2
APPLICATION NO.    : 12/047550
DATED              : January 5, 2010
INVENTOR(S)        : Jagabandhu Das et al.

Page 1 of 2

It is certified that error appears in the above-identified patent and that said Letters Patent is hereby corrected as shown below:

On the Title Page:

Item (56), References Cited, under OTHER PUBLICATIONS:

Column 2, Brown, D.J. et al. reference, change "Isomerisationss" to -- Isomerisations -- and "Equillbria" to -- Equilibria --.

The reference should read:

-- Brown, D.J. et al., "Isomerisations Akin to the Dimroth Rearrangement. Part II. The Equilibria of 4-Mercapto-1,2,3,5,7-penta-azaindenes with 4-Amino-1-thia-2,3,5,7-tetra-azaindenes", J. Chem. Soc. (C), pp. 1856-1860 (1967). --.

In the Claims:

Claim 2:

Column 95, lines 15 to 23, change

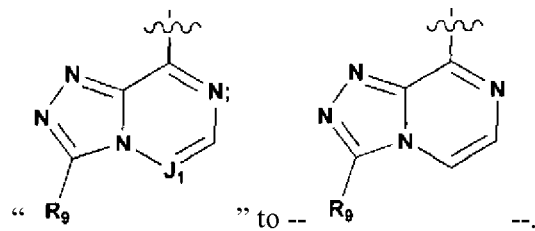

Signed and Sealed this
Fourth Day of December, 2012

David J. Kappos
*Director of the United States Patent and Trademark Office*

Column 95, line 34, change "J" to -- $J_1$ --.

Claim 8:

Column 96, line 64, change "halo($C_{14}$alkyl)" to -- halo($C_{1-4}$alkyl) --.